(12) United States Patent
Komiya et al.

(10) Patent No.: US 7,871,371 B2
(45) Date of Patent: Jan. 18, 2011

(54) ENDOSCOPE SYSTEM EQUIPPED WITH MANIPULATING UNIT FOR COMMANDING MEDICAL THERAPY TO ENDOSCOPE AND MEDICAL INSTRUMENT ATTACHED THERETO

(75) Inventors: Takaaki Komiya, Tokyo (JP); Yoshio Onuki, Tokyo (JP); Yasuhito Kura, Tokyo (JP); Takehiro Nishiie, Tokyo (JP)

(73) Assignee: Olympus Medical Systems Corporation, Tokyo (JP)

( * ) Notice: Subject to any disclaimer, the term of this patent is extended or adjusted under 35 U.S.C. 154(b) by 998 days.

(21) Appl. No.: 11/592,094

(22) Filed: Nov. 2, 2006

(65) Prior Publication Data

US 2007/0100201 A1    May 3, 2007

(30) Foreign Application Priority Data

Nov. 2, 2005  (JP)  ............................. 2005-320040

(51) Int. Cl.
*A61B 1/00* (2006.01)

(52) U.S. Cl. .................. 600/131; 600/104; 600/114

(58) Field of Classification Search ................ 600/106, 600/114, 131, 147, 152, 159, 104, 137, 146; 345/156
See application file for complete search history.

(56) References Cited

U.S. PATENT DOCUMENTS

| | | | |
|---|---|---|---|
| 4,854,301 A | 8/1989 | Nakajima | |
| 5,159,446 A | 10/1992 | Hibino et al. | |
| 5,306,272 A | 4/1994 | Cohen et al. | |
| 5,454,378 A | 10/1995 | Palmer et al. | |
| 6,033,414 A | 3/2000 | Tockman et al. | |
| 6,554,766 B2 | 4/2003 | Maeda et al. | |
| 2003/0212308 A1* | 11/2003 | Bendall | 600/131 |
| 2003/0225395 A1 | 12/2003 | Griffis et al. | |
| 2004/0220449 A1* | 11/2004 | Zirps et al. | 600/104 |
| 2005/0119522 A1* | 6/2005 | Okada | 600/106 |
| 2005/0187538 A1 | 8/2005 | Boese et al. | |
| 2005/0192475 A1* | 9/2005 | Okada | 600/106 |
| 2005/0222587 A1* | 10/2005 | Jinno et al. | 606/130 |
| 2005/0234434 A1* | 10/2005 | Sunaoshi | 606/1 |
| 2008/0103358 A1* | 5/2008 | Suzuki | 600/106 |

FOREIGN PATENT DOCUMENTS

| | | |
|---|---|---|
| EP | 0 776 739 A2 | 6/1997 |
| JP | 57-190541 | 11/1982 |
| JP | 61-37938 | 8/1986 |
| JP | 2000-207 | 1/2000 |
| JP | 2005270171 A * | 10/2005 |
| WO | WO 03100717 A1 * | 12/2003 |

\* cited by examiner

*Primary Examiner*—Thomas J Sweet
*Assistant Examiner*—Ryan Henderson
(74) *Attorney, Agent, or Firm*—Scully, Scott, Murphy & Presser, P.C.

(57) ABSTRACT

An endoscope system comprises an endoscope, manipulating unit, and controlling unit. The endoscope is equipped with an elongated and flexible insertion tube being inserted into an object being examined and formed to be used in combination with a therapeutic instrument. The insertion tube has a distal section accommodating therein at least an optical system for imaging and presenting a longitudinal direction. The manipulating unit is manually manipulated for commanding operations of at least the therapeutic instrument and formed to be loaded to the insertion tube and slidable along the insertion tube in the longitudinal direction thereof. The controlling unit controls at least the therapeutic instrument based on a command from the manipulating unit.

12 Claims, 37 Drawing Sheets

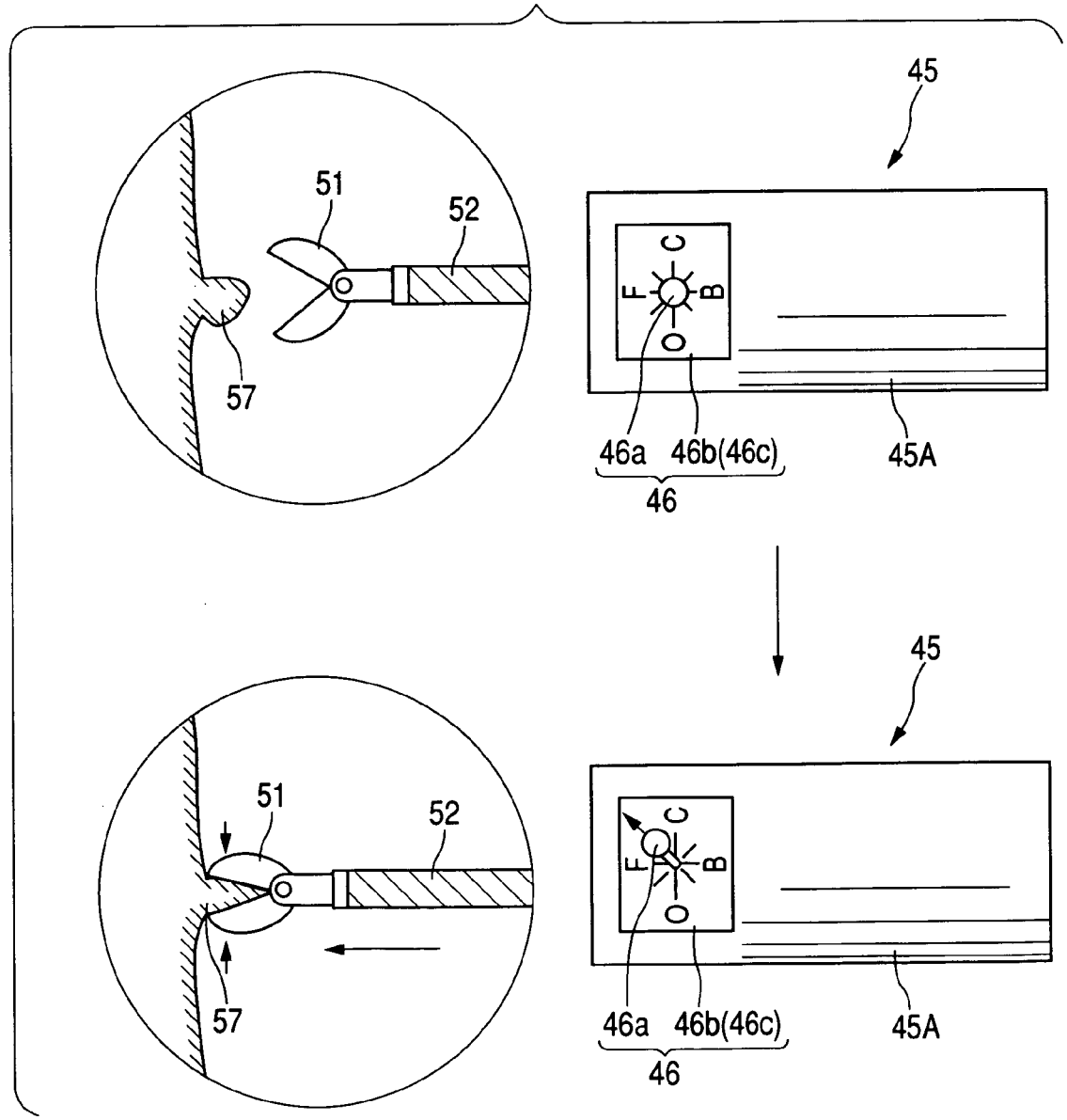

ENDOSCOPE SYSTEM EQUIPPED WITH MANIPULATING UNIT FOR COMMANDING MEDICAL THERAPY TO ENDOSCOPE AND MEDICAL INSTRUMENT ATTACHED THERETO

CROSS REFERENCE TO RELATED APPLICATION

The present application relates to and incorporates by reference Japanese Patent application No. 2005-320040 filed on Nov. 2, 2005.

BACKGROUND OF THE INVENTION

1. The Field of the Invention

The present invention relates to an endoscope system provided with an endoscope which can be combined with a therapeutic instrument, and in particular, to the endoscope system provided with a manipulating unit commanding operations needed by at least the medical instrument.

2. Related Art

In recent years, endoscopes have been used widely in the medical therapeutic filed. A typical endoscope is provided with a thin and elongated insertion tube equipped with a bendable section positioned at the end thereof and an operating unit with such members as knobs and switches being operated. Such operating members are used by operators to issue commands for various operations to obtain endoscopic operations.

Examples of endoscopic treatments in the medical field include a treatment for lesions in the digestive system and pancreatic duct system. As currently known therapy for the pancreatic duct system conducted with the use of an endoscope, there are diagnostic treatments contrast-imaging the bile duct and pancreatic duct by using the endoscope and therapeutic treatments for removing calculus in the bile duct using a balloon and a gripping therapeutic instrument.

In these treatments, the insertion tube of an endoscope is inserted in a body cavity of an object being treated, so that an imaging optical system embedded in the distal section of the insertion tube provides images of organs in the body cavity and/or a balloon and a gripping therapeutic instrument delivered through a therapeutic-instrument channel provide necessary medical treatments.

In cases where the therapeutic instrument is inserted into the therapeutic-instrument channel of a conventional endoscope, it is necessary for an operator, with holding the sheath of the instrument by hand, to insert the therapeutic instrument into the channel by a hand-feed manner. However, this inserting work takes much labor, because therapeutic instruments have a length of as long as 2 meters. In addition, much attention should be paid for the insertion. Accordingly, as a whole, work for the insertion and the various operations of therapeutic instruments have been very hard.

Some conventional techniques are provided to try to solve this problem. One conventional technique is proposed by Japanese Patent Laid-open Publication No. 57-190541, in which there is provided an instrument inserting/pulling-back apparatus combined with an endoscope. The endoscope is provided with a therapeutic-instrument channel through which a therapeutic member is mechanically inserted and pulled back into and from a body cavity of a patient being examined by the instrument inserting/pulling-back apparatus. In this system, when the distal end of the therapeutic instrument reaches a tube position near the distal end of the insertion tube, the mechanical insertion operation is released and then the operation is switched to manual work for subtle inserting operations.

Additionally, another Japanese Patent Laid-open Publication No. 2000-207 proposes another system, in which, besides the foregoing inserting/pulling-back function to therapeutic instruments, an endoscope system is provided with an instrument inserting/pulling-back apparatus for driving a therapeutic member attached to the distal end of a therapeutic instrument. The various functions of this inserting/pulling-back apparatus are instructed by foot switches.

By the way, operators such as doctors should grip the insertion tube part of which including its distal section is inserted in a body cavity of a patient so that the distal section is surely located to track a lesion in the body cavity. In other words, operators should observe a lesion by images obtained by imaging means arranged at the distal end of the insertion tube and operate the therapeutic member within a filed of view of imaging tracked by the distal section. Hence the therapeutic member, which appears from the distal end of the insertion tube, has to always be kept within the file of view for treatments of the lesion. For this reason, an operator is required to hold the insertion tube so as not to move it.

In particular, in the apparatus disclosed by Japanese Patent Laid-open Publication No. 57-190541, when a therapeutic instrument is inserted into a body cavity, which requires sensitive manual motions, an operator is obliged to hold the operating base portion of an endoscope in one hand and to insert the therapeutic instrument with the other hand. In addition, the operator should release the other hand from the endoscope when it is required to handle a therapeutic to handle a therapeutic member of the therapeutic instrument.

Thus the operator has frequently been confronted with a difficulty in that the tip of the insertion tube is not fixed easily and not always held next to a lesion, due to the affection of the peristaltic motion of a body cavity on the flexible insertion tube. It has also been frequent that the operator loses the lesion in endoscopic images, giving rise to a difficulty in a smooth treatment on the therapeutic instruments. In other words, in such a case, the operator should repeat many times an approach of the tip of the insertion tube to a lesion, resulting in troublesome work.

Meanwhile in the system disclosed by Japanese Patent Laid-open Publication No. 2000-207, an operator is allowed to handle the foot switches(s) to command the insertion of a therapeutic instrument and the necessary motions of a therapeutic member of the instrument, with operator's both hands holding and gripping the endoscope. However, the operator is engaged in treating and inspecting a lesion with looking at endoscopic images coming from the endoscope, so that the operator is required to handle a foot switch with the operator's foot after visually checking the position of the foot. In cases where there are arranged a plurality of foot switches, an operator should select a desired foot switch or handle plural foot switches at the same time. This kind of handling work becomes difficult for operators and in particular, the foot-operation makes it difficult to perform sensitive work to insert the therapeutic instrument and move the instrument member.

Further, the therapy on the endoscope frequently involves other medical tools such as therapeutic instruments operative on high-frequency power. In some cases, such kinds of therapeutic instruments adopt foot switches, which makes the situation even worse by handing the plurality of foot switches including foot switches for inserting/pulling the insertion tube of the endoscope and switches for various medical instruments and therapeutic instruments.

SUMMARY OF THE INVENTION

The present invention has been made in consideration of the foregoing conventional difficulties, and has an object to provide an endoscope system capable of facilitating at least part of the operations necessary for at least a therapeutic instrument used in combination with an endoscope, while still allowing an operator to hold the tip of the insertion tube of the endoscope at a desired position in a body cavity of an object being examined.

In order to realize the above object, the present invention provides an endoscope system comprising: an endoscope equipped with an elongated and flexible insertion tube being inserted into an object being examined and formed to be used in combination with a therapeutic instrument, the insertion tube having a distal section accommodating therein at least an optical system for imaging and presenting a longitudinal direction; a manipulating unit manually manipulated for commanding operations of, of the endoscope and the therapeutic instrument, at least the therapeutic instrument and formed to be loaded to the insertion tube and slidable along the insertion tube in the longitudinal direction thereof; and a controlling apparatus controlling at least the therapeutic instrument based on a command from the manipulating unit.

BRIEF DESCRIPTION OF THE DRAWINGS

In the accompanying drawings:

FIG. 11 exemplifies how to operate the manipulating unit;

DETAILED DESCRIPTION OF THE PREFERRED EMBODIMENTS

Embodiments of the present invention will be described hereafter with reference to the figures.

First Embodiment

With reference to FIGS. 1-11 and 54-56, a first embodiment of an endoscope system according to the present invention will now be described.

Figure 1:
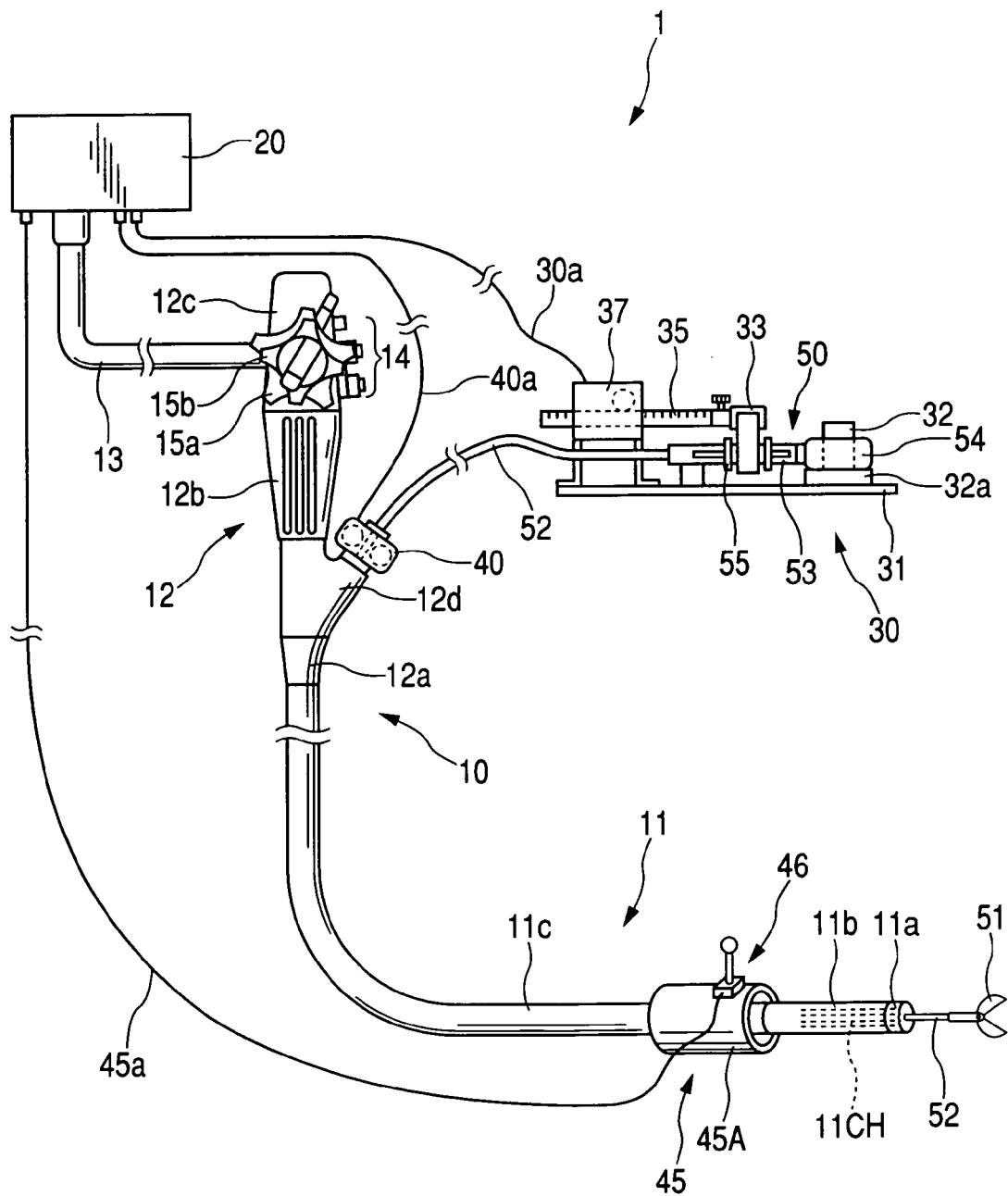
FIG. 1 is a schematic view showing the configuration of a main part of an endoscope system according to a first embodiment of the present invention.

As shown in FIG. 1, an endoscope system 1 according to the present embodiment is provided with, as essential components thereof, an endoscope 10, controller 20, instrument operating unit 30 serving as a first drive unit, instrument conveying unit 40 serving as a second drive unit, and manipulating unit 45. The controller 20, which functions as a controller, is equipped with an endoscope processor described later, a light source unit (not shown), and a video processor (not shown). In the present embodiment, the instrument operating unit 30 is a unit to operate a therapeutic member 51 of a therapeutic instrument 50 used in combination with the endoscope and the instrument conveying unit 40 is a unit to convey (specifically, insert and pull out) via a dedicated channel formed through an insertion tube of the endoscope.

In the present embodiment, the controller 20, both units 30 and 40, and manipulating unit 45 compose an apparatus for assisting endoscopic operations for the endoscope 10. Though not shown, the controller 20 is electrically and communicably connected to display means, such as monitors, for displaying images acquired by the endoscope.

The endoscope 10 is provided with a thin and elongated insertion tube 11, an operating base holder 12 rigidly connected to a base end of the insertion tube 11, and a universal code 13 connecting the operating base holder 12 and the controller 20.

The insertion tube 11 is a soft tubular member composed of a distal section 11a, a flexibly bendable section 11b, and a flexible tubular section 11c, which are positioned and mutually rigidly connected in this order from the distal end thereof, but are flexible and bendable as a whole.

In the present embodiment and succeeding modifications, the term "distal" means the distal of the insertion tube 11, while the "base" means the base of the insertion tube it, which is rigidly connected with the operating base holder 12.

Further, the operating base holder 12 is composed of a bend protection portion 12a to which a base end of the flexible tubular section 11c is rigidly connected, a grasping portion 12b provided with an instrument inlet structure 12d, and a main operation portion 12c connected to the base portion 12a via the grasping portion 12b. All the portions 12a to 12d are rigidly combined to form a single body that is the operating base holder 12. Of these, the main operation portion 12c is provided with bending levers 15a and 15b as well as plural switches 14 used for commanding air supply, water supply, suction, and various optical operations for imaging means and illuminating means disposed to the distal section 11a. The bending lever 15 is used to command a bend at the bendable section 11b.

In this endoscope 10, a therapeutic-instrument channel 11CH (thin and elongated tubular bore, through which various therapeutic instruments are inserted and pulled out (that is, conveyed), is formed to range from the instrument inlet structure 12d to the distal section 11a through the insertion tube 11, which will be detailed later. The universal code 13 has a base end at which a connector 13a is disposed for connection with the controller 20.

The instrument operating unit 30 is electrically and communicably connected to the controller 20 via an electric cable 30a. Provided on the instrument operating unit 30 is a handle 53 of the therapeutic instrument 50 which is for example a biopsy forceps.

Further, the instrument conveying unit 40 is electrically connected to the controller 20 via another electric cable 40a and secured at the instrument inlet structure 12d of the endoscope 10. The therapeutic instrument 50 has a tubular sheath 52 and an operating wire 52a passing through the sheath 52. The sheath 52 and the operating wire 52a compose a tubular portion of the instrument 50 and this tubular portion, that is, the sheath 52 (together with the operating wire 52a), inserted in the therapeutic-instrument channel 11 CH.

The manipulating unit 45 is electrically and communicably connected to the controller 20 via a signal cable 45a and is detachably loaded onto the outer surface of the insertion tube 11 of the endoscope 10.

The therapeutic instrument 50 comprises the therapeutic member 51 located at the distal end thereof, the operating wire 52a of which one end is coupled with the therapeutic member 51 for operations, the tubular sheath 52 containing therein the operating wire 52a such that the wire 52a passes through the sheath 52 and is rotatable about a longitudinal axis of the wire 52a, and the foregoing handle 53 coupled with the other end of the operating wire 52a. For use of the therapeutic instrument 50, this instrument 50 is subjected to its inserting and pulling-out operations (conveying operations) into a body cavity of an object being examined. Such inserting and pulling-out operations are carried out by inserting and pulling out the sheath 52, as will be described later. Thus inserting and pulling out the sheath 52 means that the operating wire 52a contained in the sheath 52 and the therapeutic member 51 located at the distal end are inserted and pulled out together with the sheath 52.

Through the instrument conveying unit 40, the sheath 52 (together with the operating wire 52a) of the therapeutic instrument 50 is driven to be guided into the therapeutic-instrument channel 11CH.

In the present embodiment, the therapeutic instrument 50 is exemplified as the biopsy forceps, as stated above, so that the therapeutic member 51 is composed by the grip portion of the biopsy forceps. The sheath 52 of this therapeutic instrument 50 is inserted into the channel 11 CH in such a manner that the sheath 52 is made to freely advance and go back, thus making it possible for the therapeutic member 51 to appear from and disappear into the opening of the channel 11 CH in the front of the distal section 11a of the insertion tube 11.

Figure 2:
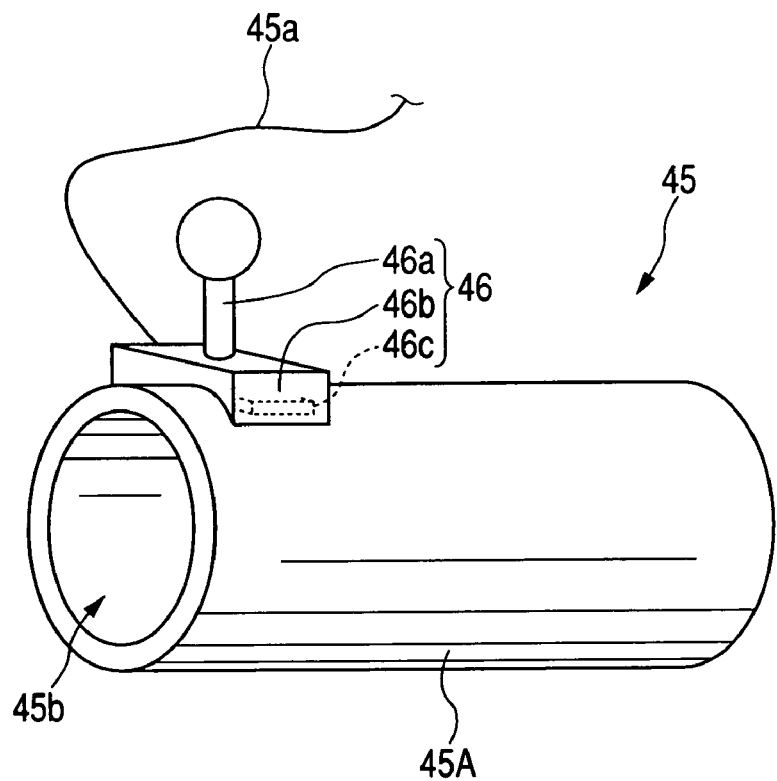
FIG. 2 is a perspective view showing a manipulating unit employed by the endoscope system.
Figure 3:
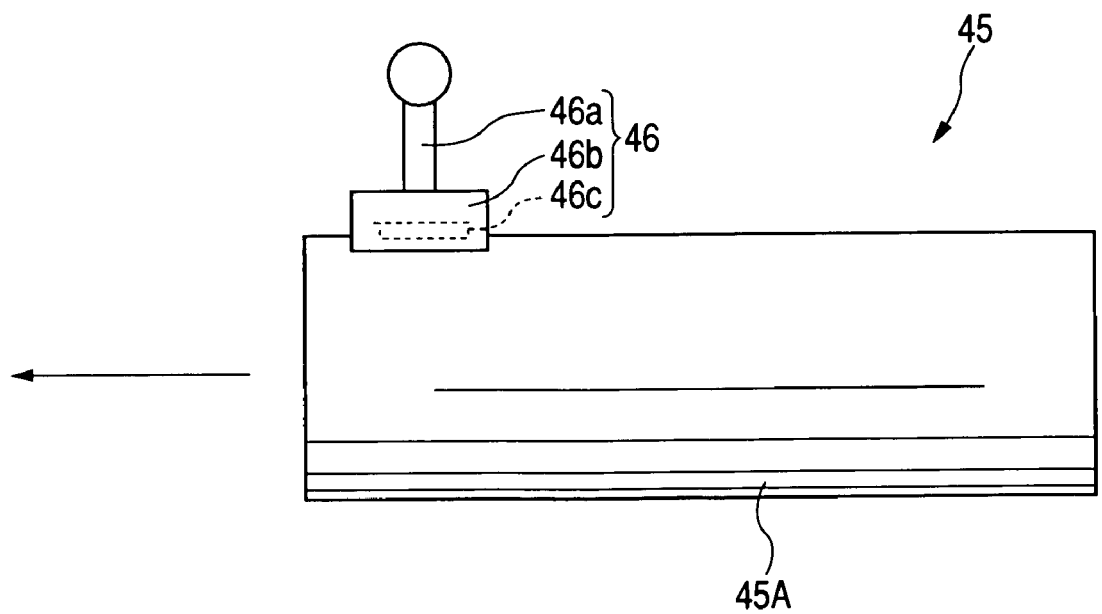
FIG. 3 is a side view showing the manipulating unit.
Figure 4:
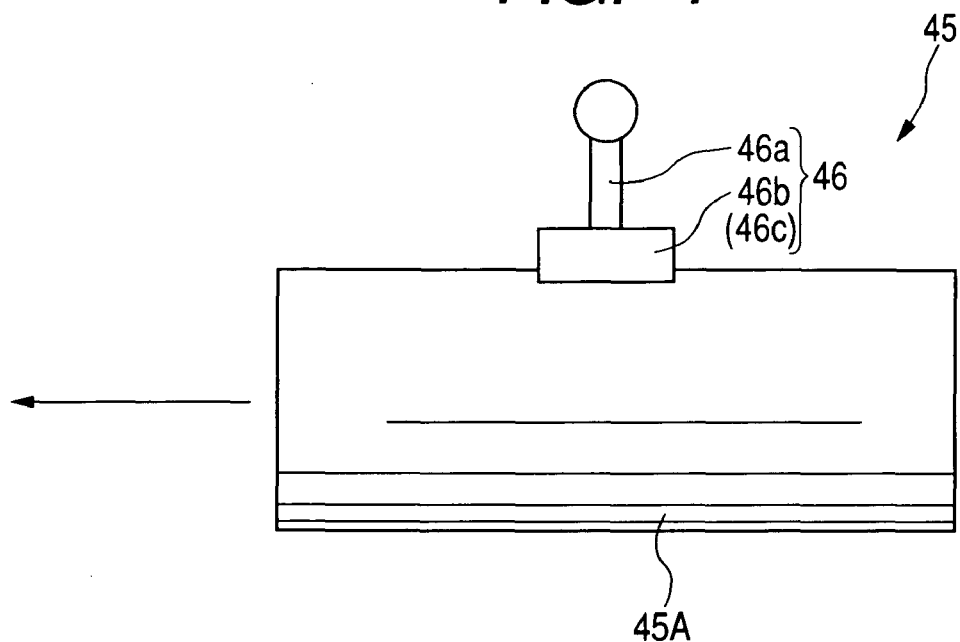
FIGS. 4 and 5 are side views each showing a modification of the manipulating unit.
Figure 5:
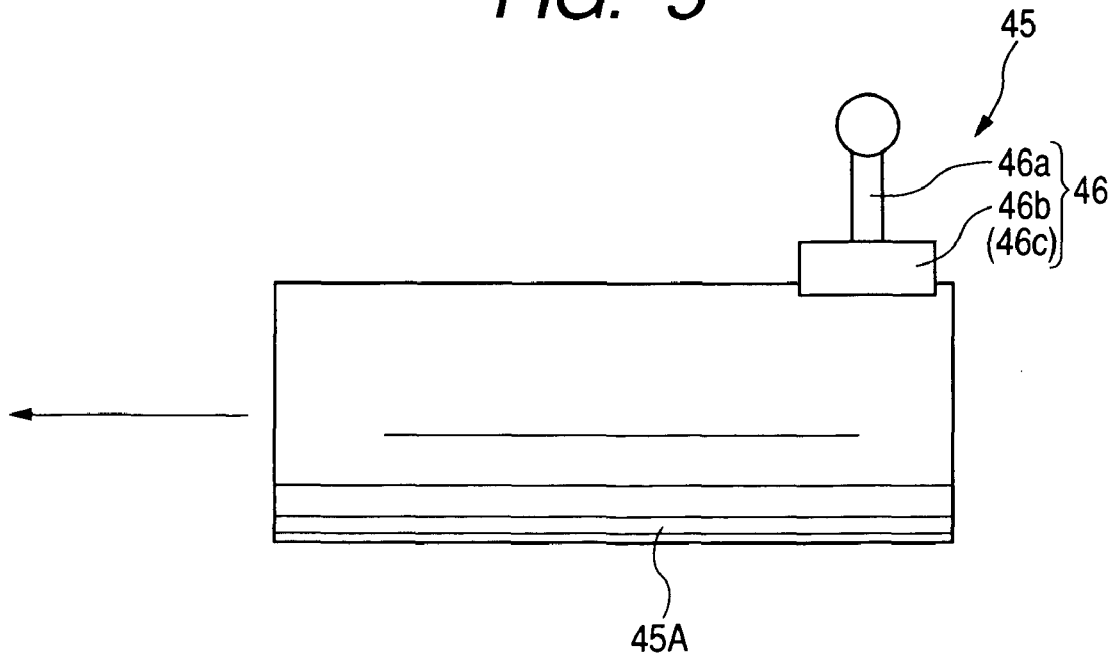

Referring to FIGS. 2 and 3, the manipulating unit 45 will now be detailed.

As shown in FIG. 2, the manipulating unit 45 comprises an approximately-cylindrical external loading tube 45A through which an inserting through-hole 45b is formed. This external loading tube 45A functions as a member through which the insertion tube is inserted. At a distal-side position on the outer surface of the external loading tube 45A, an input device 46 which comprises an operation lever 46a and a lever supporter 46b is arranged. A signal cable 45a extends outward from the lever supporter 46b for transmitting an operation command signal coming from the operation lever 46b.

The distal end of the outward loading tube 45A is directed toward the distal section 11a of the insertion tube 11 of the endoscope 10 when the insertion tube 11 is inserted from the base-side opening of the inserting through-hole 45b of the tube 45A. For this purpose, the inserting through-hole 45b has a diameter not only being larger than an outer diameter of the insertion tube 11 but also allowing the manipulating unit 45 to be slidable along the insertion tube 11 when being loaded to the insertion tube 11 (that is, the insertion tube 11 is inserted through the tube 45A).

The position of the manipulating unit 46 is not limited at the distal-side one on the external loading tube 45A, as described above. Alternatively, as exemplified in FIG. 4, the manipulating unit 46 may be positioned substantially midmost on the outer surface of the external loading tube 45A in the axial direction thereof. Still alternatively, as exemplified in FIG. 5, the manipulating unit 46 may be positioned near the base side on the external loading tube 45A.

Figure 54:
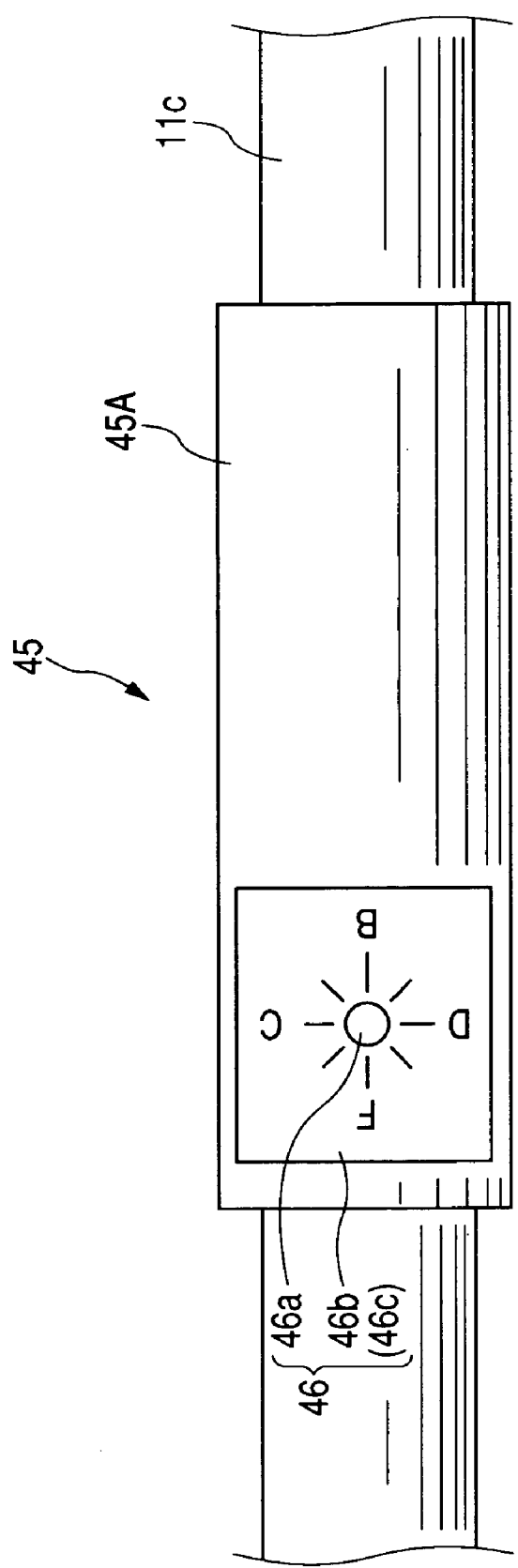
FIG. 54 is a plan view of the manipulating unit employed in the first embodiment.

As shown in FIG. 54, the operation lever 46a is a four-way switch which is tiltable in four directions F, B, O and C (upward, downward, leftward, and rightward). The input switch 46 still has a detecting circuit 46c including two trimmer resistors, as shown in FIGS. 2 and 3. The two trimmer resistors are placed as sensors to detect tilted angles of the operation lever 46a in each of the F-B and O-C directions respectively based on changes in the resistance and output electrical operation command signals in which the tilted angles are reflected in both directions, respectively. The detected operation command signals are sent via the signal cable 45a to the controller 20, wherein the signals are fed to an A/D converter 123a belonging to a motor processor 123 (refer to FIG. 55).

Figure 6:
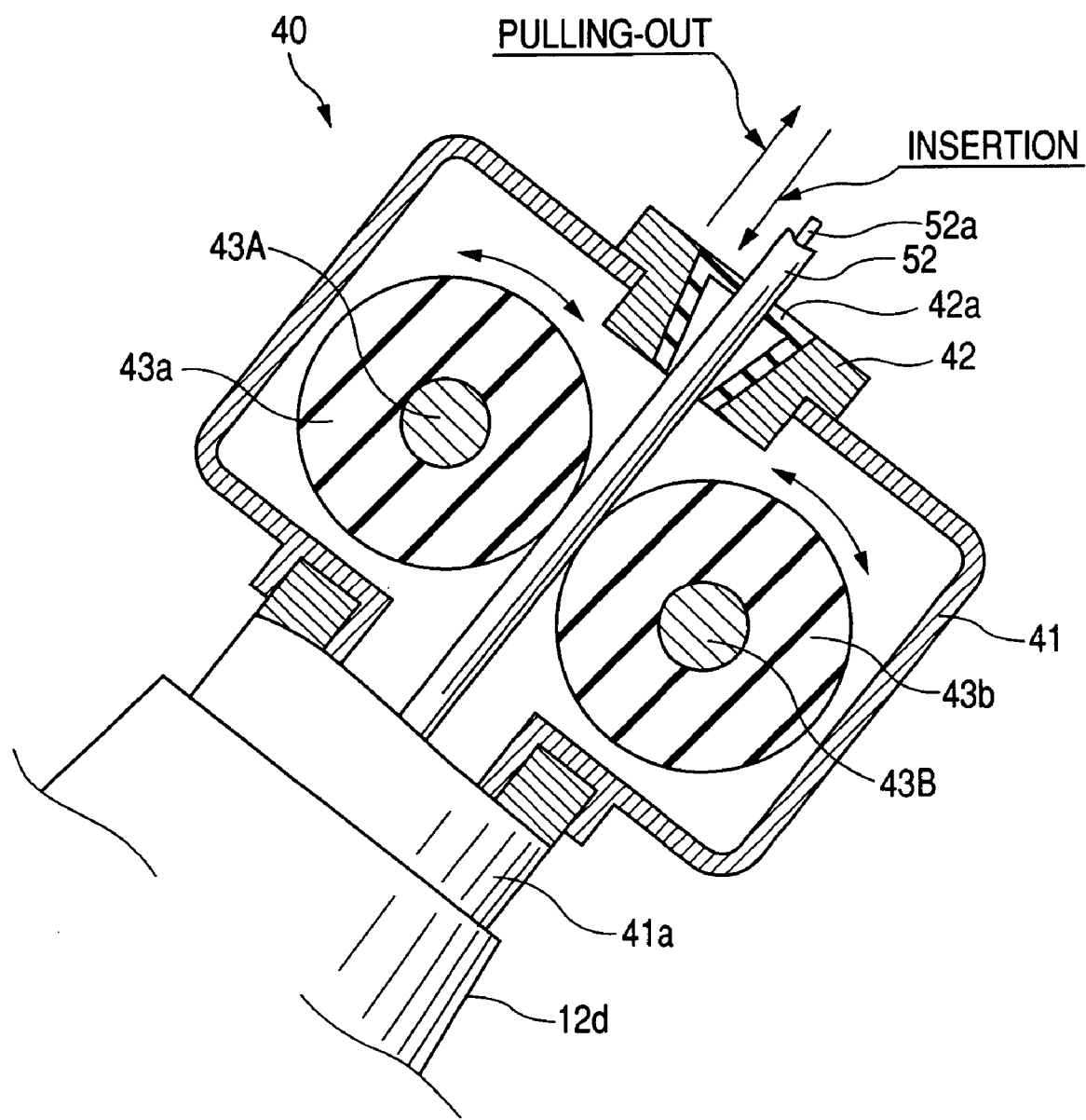
FIG. 6 is a longitudinal sectional view of an instrument conveying unit employed in the endoscope system, which shows the internal structure thereof.
Figure 7:
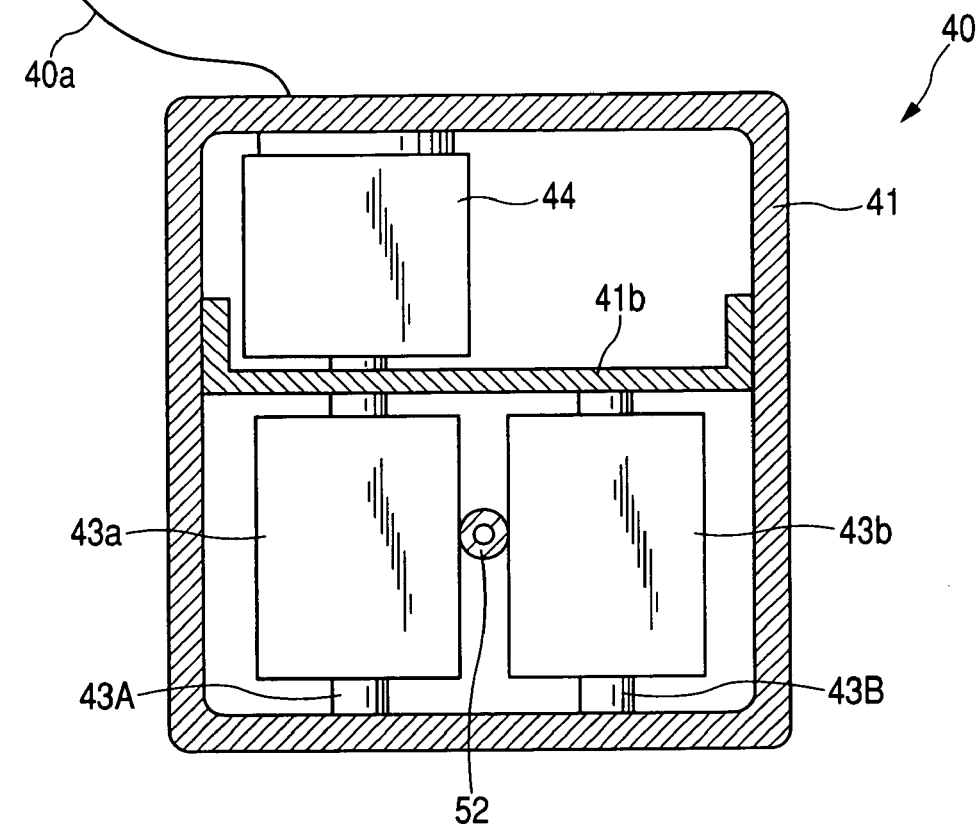
FIG. 7 is a lateral sectional view of the instrument conveying unit, which also shows the internal structure thereof.

Referring to FIGS. 6 and 7, the instrument conveying unit 40 will now be detailed.

As shown in FIG. 6, the instrument conveying unit 40 is provided with a box-shaped member 41 and two rollers 43a and 43b rotatably arranged within the box-shaped member 41. In one of the walls forming the box-shaped member 41, formed is an insertion hole portion 42 through which the sheath 52 of the therapeutic instrument 50 is inserted, while in the opposite wall to the wall with the insertion hole portion 42 formed, formed is a scope fixing member 41a. This scope fixing member 41a guides the sheath 52 into the therapeutic-instrument channel 11CH of the endoscope 10 and is used as a connection to the instrument inlet structure 12d of the endoscope 10. The insertion hole portion 42 also serves as a guide guiding the sheath 52 into the channel 11CH.

The insertion hole portion 42 is filled with a clamp plug 42a made from elastic material, in which the clamp plug 42a still has an insertion hole through which the sheath 52 is slidably inserted and pulled out. Meanwhile the scope fixing member 41a is linked with the opening of the therapeutic-instrument channel at the instrument inlet structure 12d in an airtight manner.

As a result, when the sheath 52 of the therapeutic instrument 50 is inserted or pulled out in a case where the body cavity is expanded by air supply or water supply via the endoscope 10 in order to facilitate an easy observation therein, the clamp plug 42a and scope fixing member 41a keep the air tightness of the therapeutic-instrument channel so as to prevent a drop in the pressure within the body cavity.

The two rollers 43a and 43b in the box-shaped member 41 are made from, for example, elastic material and rotatable in response to rotation of shafts 43A and 43B, respectively. Both rollers 43a and 43b press, by their rotations, the outer surface of the sheath 52 of the therapeutic instrument 50, placed in a gap formed between the rollers 43a and 43b, so as to allow the sheath 50 to go forward and go back (that is, inserted and pulled out) through the therapeutic-instrument channel 11CH.

Of both rollers, one roller 43a is a driving roller and its rotation shaft 43A is driven by an electric motor 44 placed in the box-shaped member 41 (refer to FIGS. 6 and 7). Meanwhile the other roller 43b is a driven roller of which rotation helps the sheath 52 move smoothly which go forward and backward in to the rotation of the driving roller 43a.

The rollers 43a and 43b are rotatably supported from the side walls and a supporting plate 41b in the box-shaped member 41 such that the rollers 43a and 43b are spaced apart from each other to form the respective roller surfaces a gap of predetermined length therebetween and the rotation shafts 43A and 43B are in parallel to each other.

Figure 8:
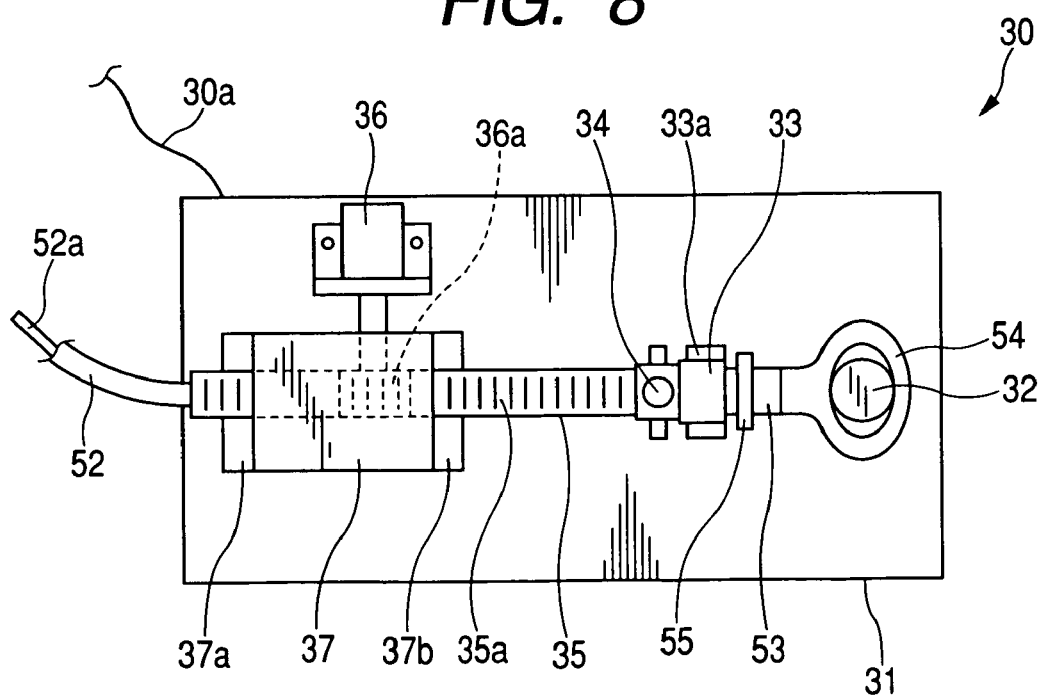
FIG. 8 is a plan view of an instrument operating unit employed in the endoscope system.
Figure 9:
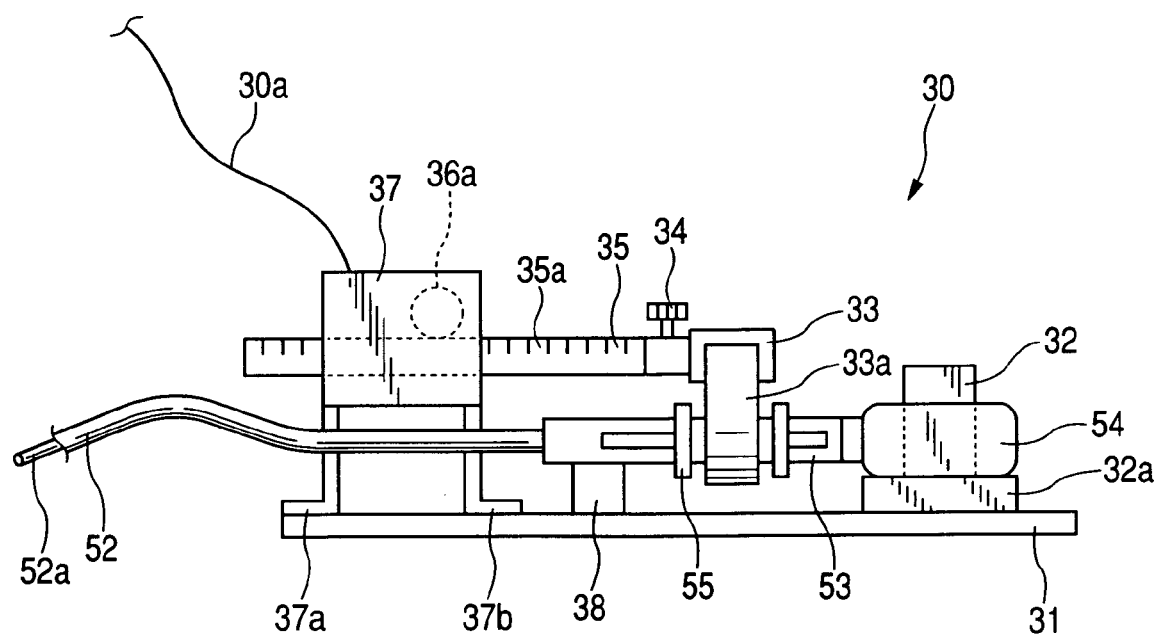
FIG. 9 is a side view of the instrument operating unit.

Referring to FIGS. 8 and 9, the instrument operating unit 30 will now be detailed.

As shown, the instrument operating unit 30 is provided with a plate-like base 31, a ring holding member 32 protruded from a surface of the base 31, a slider holding member 33 pinching a slider 55 of the therapeutic instrument 50, and other some components including a rack 35, a motor 36, a holding box 37, a mounting portion 38. Of these, the rack 35 is linked with the slider holding member 33 by a screw 34. The motor 36 has a rotation shaft on which a pinion gear 36a is secured so as to engage with a liner gear portion 35a of the rack 35. The holding box 37 is secured on the base 31 by securing members 37a and 37b and accommodates therein the pinion gear 36a, and holds the rack 35 to allow its linear motions for inserting and pulling-back operations. The mounting portion 38 is placed on the base 31 and supports the handle 53 of the therapeutic instrument 50.

The ring holding member 32 is mounted on an annular ring base 32a to be built thereon and arranged so as to be inserted into a finger-engaging ring 54 of the therapeutic instrument 50, so that the handle 53 is held at the instrument operating unit 30. The ring base 32a is fixedly mounted on the base at a position near to one end of the base 31.

The ring holding member 32 is shaped into a column having an outer diameter substantially equal to an inner diameter of the finger-engaging ring 54, thus securely holding the handle 53, that is, the therapeutic instrument 50. Incidentally the outer diameter of the ring holding member 32 may be formed to have a dimension slightly smaller than the inner diameter of the finger-engaging ring 54, if the ring holding member 32 is used with an elastic tube member mounted on the outer surface of the member 32. Employing this manner allows the handle 53 to be securely held by the instrument operating unit 30.

The ring base 32a has a predetermined height, whereby the handle 53 of the therapeutic instrument 50 is separated from the base 31 by a predetermined distance.

As shown in FIGS. 8 and 9, the slider holding member 33 is formed to have two holding plates 33a extending in an up-and-down direction perpendicular to the base 31, in which the holding members 33a hold the slider 55 of the therapeutic instrument 50 by pinching the slider 55 by the sides. Specifically, the slider 55 is formed into a drum-like shape having a flange on each of both axial end sides thereof, so the two holding members 33a are placed to pinch a body portion existing between the flanges. The slider holding member 33 is linked with one end of the rack 35 by a setscrew 34, as described before.

The pinion gear 36, which can be rotated together with the rotation of the motor 30, is engaged with the linear gear portion 35a. Thus the rotation of the pinion gear 36 will cause the rack 35 to selectively move forward and backward in the axial (longitudinal) direction of the handle 53. This movement becomes relative motions to the holding box 37. Thus the slider holding member 33 allows the slider 55 to move along the handle 53 for inserting and pulling-out operations of the therapeutic instrument 50.

As described, the therapeutic instrument 50 has an operating wire 52a that passes through the bore of the sheath 52, and a distal end of the operating wire 52a is linked to the therapeutic member 51 and the other base end is linked to the slider 55. The sheath 52 and the operating wire 52a compose the tubular portion of the instrument 50. Conveying the sheath 52 results in conveying the operating wire 52a, together with the therapeutic member 51 disposed at the distal end thereof.

Thus, in response to the forward and backward motions of the sliders 55 in the axial direction of the handle 53, the operating wire 52a is pulled or relaxed so that these pulling and relaxation motions are converted to given operations of the therapeutic operations. In the present embodiment, the therapeutic member 50 is a biopsy forceps, so that the given motions are open and close operations of a gator-grip-shaped gripping portion thereof.

Figure 55:
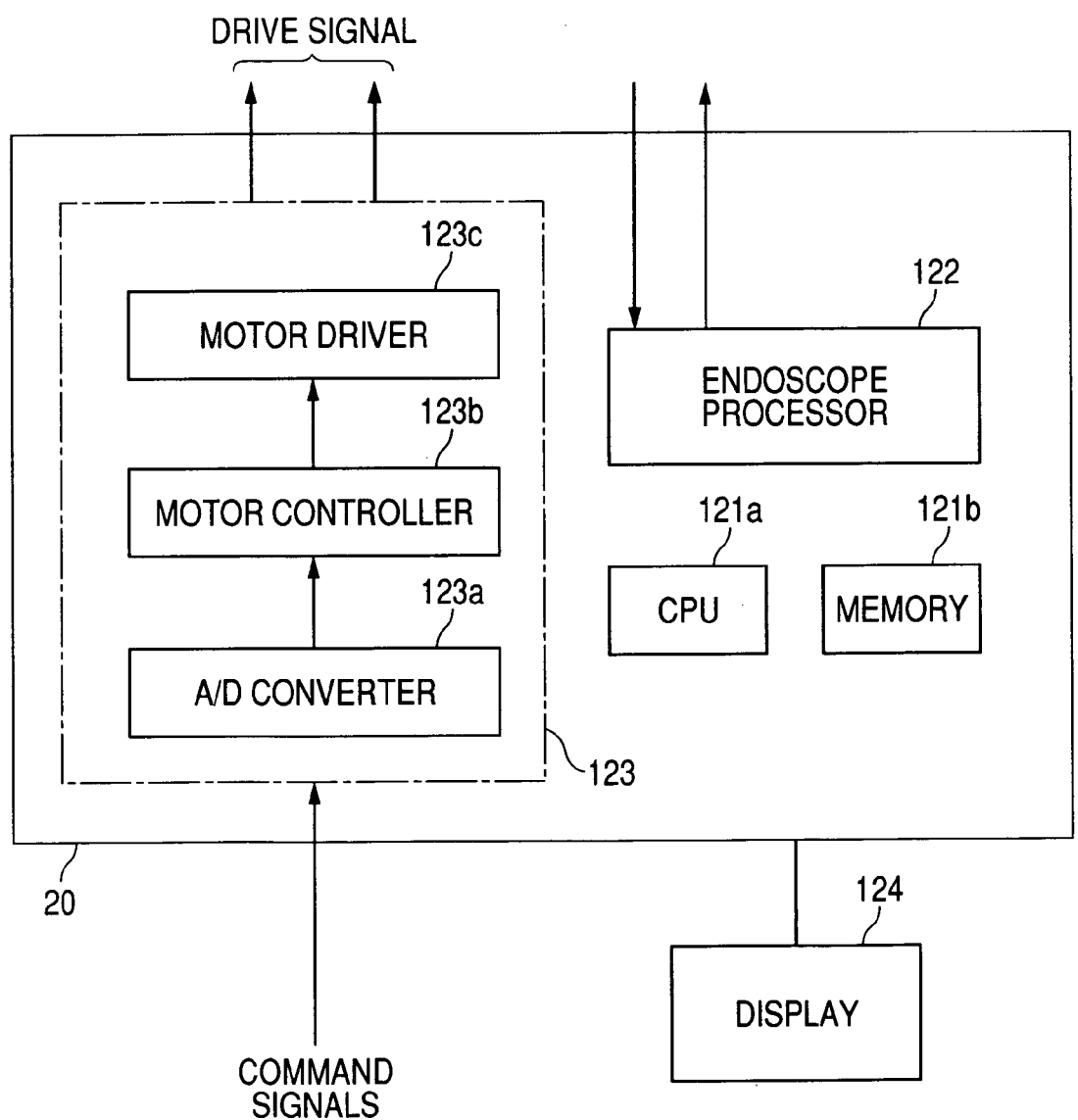
FIG. 55 is a functional block diagram of a controller in the first embodiment.

Referring to FIG. 55, the configuration of the controller 20 will now be exemplified. In the present embodiment, the controller 20 is formed using circuitry for performing software processing carried out by a CPU (central processing unit) as well as circuitry for controlling the motors, but may be formed based on other known configuration systems.

As shown in FIG. 55, the controller 20 comprises a CPU 121a, memory 121b, endoscope processor 122 for controlling the operations of the endoscope 10, and motor processor 123 controlling the motors necessary for manipulating the therapeutic member 50. The endoscope processor 122 operates as an endoscope processor in cooperation with the CPU 121a and memory 121b. The motor processor 123 operates as a motor controlling unit in combination with the CPU 121a and memory 121b.

The motor processor 123 comprises, as stated, the A/D converter 123a, motor processor 123b, and a motor driver 123c. To the controller are connected a display 124 with LCDs and/or CRT.

As is known, the endoscope processor 122 is configured to perform processing necessary by the endoscope 10 Itself. The processing includes processes for air supply, water supply, suction, illuminating, and imaging.

The A/D converter 123a receives an analog-format operation command signal coming from the manipulating unit 45 via the signal cable 45a, and coverts the signal into a corresponding digital-format signal which can be processed by the motor processor 123b. In response to reception of the digital command signal, the motor processor 123b computes drive signals necessary for driving the motors depending on the command signal. By receiving the drive signals, the motor driver 123c drives the motors.

Meanwhile, the endoscope 10 has imaging means such as a CCD camera (not shown) in the distal section 11a of the insertion tube 11. Image information acquired by the imaging means is transmitted to a camera control unit (not shown) in the endoscope processor 122, whereby image signals are generated by the endoscope processor 122. Such Image signals are fed to the display 124 for presenting endoscopic images.

The operations and advantages of the endoscope system 1 according to the present embodiment will now be described.

An operator (doctor) examines a body cavity of an object being examined with monitoring acquired endoscope images, during which time, when a lesion is found in the cavity, the operator is able to treat the lesion by performing various therapeutic operations such as ablation. In the present embodiment, the use of the biopsy forceps will now be exemplified.

Figure 10A:
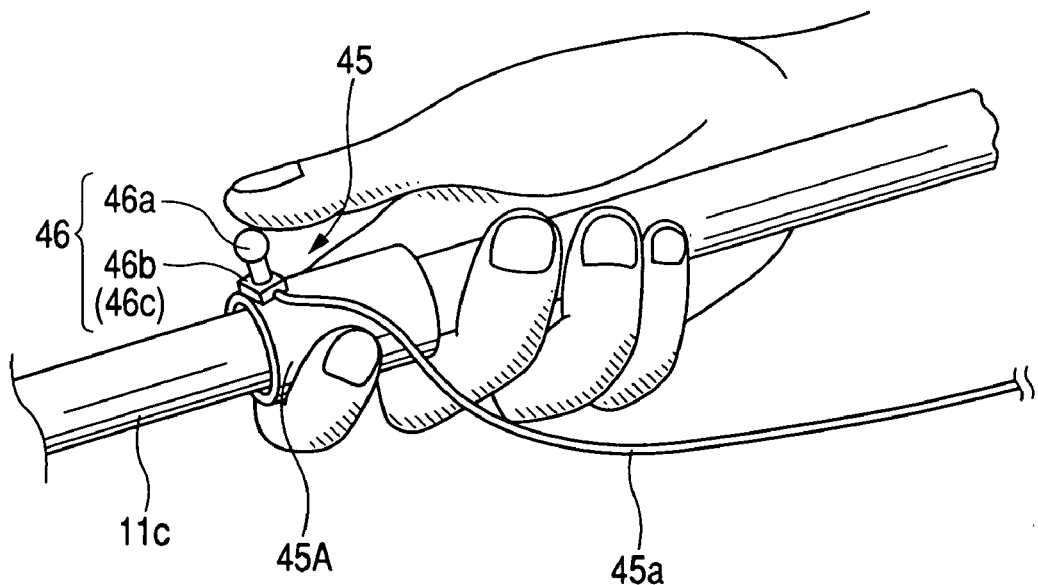
FIGS. 10A and 10B are perspective views each explaining a state in which the manipulating unit is loaded to the insertion tube of an endoscope of the endoscope system.
Figure 10B:
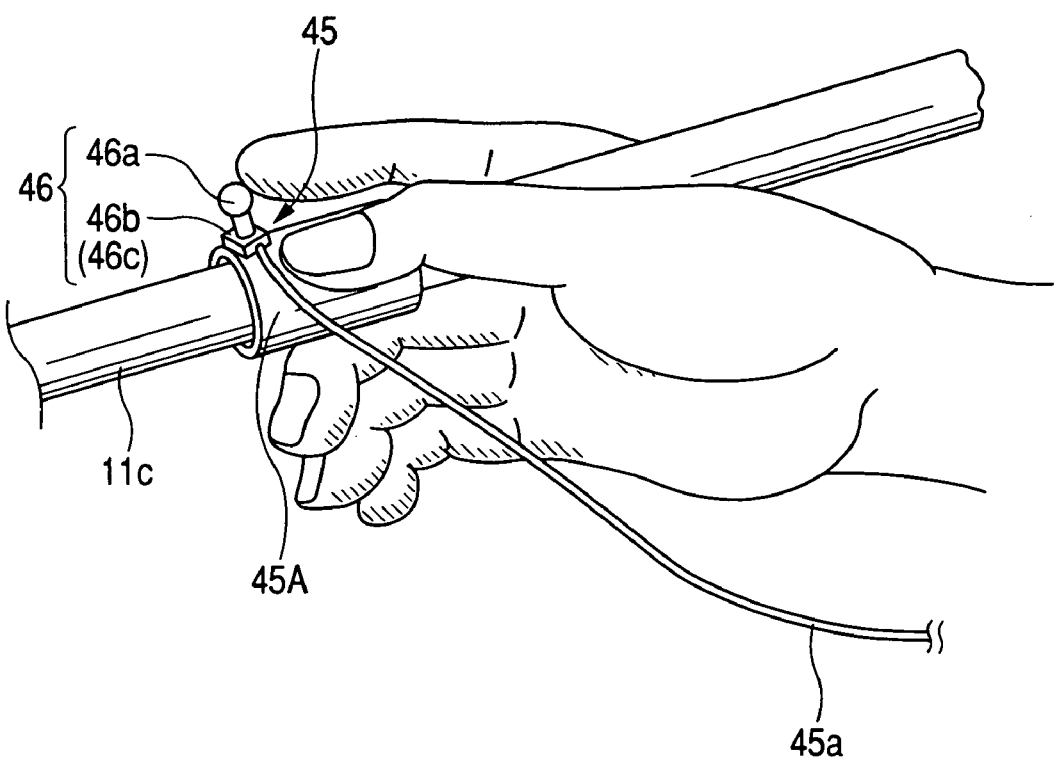

In this case, as illustrated in FIGS. 10A and 10B, the operator loads the manipulating unit 45 to the insertion tube 11 of the endoscope 10 such that the insertion tube 11 passes through the external loading tube 45A, and inserts the insertion tube 11 into a body cavity of an object being treated.

Then the operator fixes the handle 53 of the therapeutic instrument 50, which is placed to pass through the therapeutic-instrument channel 11CH, at the instrument operating unit 30. Concretely, the slider holding member 33 with the rack 35 removed is loaded on the slider 55 so as to put the ring holding member 32 in the finger-engaging ring 54 of the handle 53.

In this operation, the operator inserts the ring holding member 32 into the finger-engaging ring 54 until the handle 53 of the therapeutic instrument 50 partly touches the mounting portion 38 on the base 31. Further, as shown in FIGS. 10A and 10B, the operator uses the setscrew 34 to connect the slider holding member 33 and the rack 35 with each other.

The operator then proceeds to loading the instrument conveying unit 40 to the instrument inlet structure 12d of the endoscope 10. Through the unit 40, the sheath 52 of the therapeutic instrument 50 is inserted into the therapeutic-instrument channel 11CH of the endoscope 10 so that the therapeutic member 51 advances therein at the head. In this work, the operator continues the insertion until the therapeutic member 51 passes the two rollers 43a and 43b in the instrument conveying unit 40 to allow the sheath 52 to begin being pressed between the two rollers 43a and 43b. Alternatively, the operator may manually carry out an initial insertion, in which the sheath 52 is continued to be inserted into the therapeutic-instrument channel until the therapeutic member 51 reaches the distal end of the insertion tube 11 (i.e., the therapeutic-instrument channel).

With observing endoscopic images on the display 124, the operator then inserts the insertion tube 11 into a body cavity of an object so that the distal section 11a is inserted at the head in the cavity. In this operation, according to need, the operator further inserts the insertion tube 11 and bends the bendable section 11b such that the distal section 11a positions near a lesion being interested and adjusts its positions to allow the endoscopic view to catch the lesion. Then the operator performs therapeutic operations toward the lesion with the help of the endoscopic Images on the display 124.

To be specific, it is required for the operator to hold the distal section 11a of the insertion tube 11 so that a lesion is always and surely within a field of view displayed in endoscopic images, when the region is found in the body cavity. For realizing such a situation, the operator not only grips the insertion tube 11 but also holds the manipulating unit 45 in one hand.

In this grip and hold operation, for example, as shown in FIG. 10A, the first finger is used to hold the manipulating unit 45 so as to firmly wrap around the outer surface of the unit 45 and the thumb is used to hold the operation lever 46a of the unit 45, with the insertion tube 11 gripped by the remaining three fingers. An alternative holding way is shown in FIG. 10B, the operator holds the insertion tube 11 between the thumb and the second joint of the first finger and manipulates the operation lever 46a by the first finger, like holding a pen.

Then the operator applies a treatment to the lesion, such as polyp, with observing endoscopic images on the display 124.

That is, an operator's one-handed grip of the manipulating unit 45 allows both the manipulating unit 45 and the insertion tube 11 to be held at the same time, during which the operator manipulates the operation lever 46a. As shown in FIG. 11, when the operator tilts the operation lever 46a toward a desired way, the therapeutic member 51 of the therapeutic instrument 50 can be opened or closed selectively and the sheath 52 can be inserted or pulled back together the operation wire 52a in a selective manner.

In the present embodiment, for markings "F", "B", "O" and "C" for tilt operations are printed on the upper surface of the lever supporter 46b of the input device 46. Thus, the operation lever 46a is tilted toward the marking "F", that is, toward the distal end of the input device 46, in the longitudinal direction of the insertion tube 11 (refer to FIG. 54), the sheath 52 can be made to advance together with the operation wire 52 (that is, inserted).

In contrast, the operation lever 46a is tilted toward the marking "B", that is, toward the distal end of the input device 46 (refer to FIG. 54), the sheath 52 can be made to return together with the operation wire 52 (that is, pulled back).

In this way, when the operation lever 46a is operated to tilt in either the frontward or backward direction (toward the marking "F" or "B") of the input device 46, an amount of the trimmer resistance in the detecting circuit 46c is changed depending on the tiled angle. An analog-format detection signal, in which the changes in the resistance are reflected, is thus sent to the controller 20 via the signal cable 45a. In the controller 20, the A/D converter 123a of the motor controller 123 receives the detection signal to convert it to a corresponding digital-format signal. This signal is processed by the motor processor 123b so as to compute a drive signal in compliance with the lever operated state. The resultant drive signal is fed to the motor driver 123c to drive the rotation of the motor 44 of the instrument conveying unit 40.

As a result, the instrument conveying unit 40 is powered so the motor 44 is forced to rotate in a predetermined rotational direction at a predetermined speed of rotation. Responsively to the rotation of the motor 44, the driving roller 43a in the instrument conveying unit 40 is rotated in a specified rotational direction, which causes the sheath 52 (pressed between the tow rollers 43a and 43b) to selectively move forward or backward through the therapeutic-instrument channel 11CH of the endoscope 10.

Hence, by selectively making the operation lever 46a tilt in the forward or backward direction, the therapeutic member 51 can be moved forward or backward, that is, can emerge or submerge from or in the distal section 11a of the insertion tube 11 of the endoscope 10. This operation can be done by, as one mode of operations, one operator.

In addition, when the operation lever 46a is tilted toward the left side specified by the marking "O" in FIG. 11 in the direction perpendicular to the longitudinal direction of the insertion tube 11 (that is, the input device 46), the therapeutic member 51 can be opened. In contract, when the operation lever 46a is tilted toward the right side specified by the marking "C" in FIG. 11, which is opposite to the above, the therapeutic member 51 can be closed.

Like the foregoing, the tilt of the operation lever 46a in the right and left directions (in either the "O" or "C" marking side) is reflected in the detection signal from the detecting circuit 46c, thanks to changes in amounts of the trimmer resistance. Since the detection signal is supplied to the controller 20, the drive signal depending on the present operated state of the lever 46a is provided to the instrument operating unit 30 via the signal cable 30a in the same way as the foregoing. The motor mounted in the operating unit 30 is rotated at a predetermined rotational direction and a predetermined speed of rotation.

Responsively to the rotation of the motor 36, the pinion gear 36a is rotated, which causes the linear gear portion 35a to move the rack 37 linearly relative to the holding box 37. The slider holding member 33, which is linked with the rack 35, moves the slider 55 of the therapeutic instrument 50 forward or backward along the axial direction of the handle 53 in a selectively manner, whereby the instrument 50 is subjected to traction or relaxation in a controlled manner.

Hence, by selectively making the operation lever 46a tilt in the rightward or leftward, the therapeutic member 51 can be opened or closed.

In addition, as shown in the lower column in FIG. 11, when the operator tilts the operation lever 46a toward any of four regions sectioned among the four markings "F," "B," "O," and "C," the inserting or pulling-out operation can be done in parallel with the open or close operation in any combination.

Hence, it is possible to make the member 51 gather the tissue 57. The operator is able to grip the insertion tube 11 and, concurrently with this grip, to handle the operation lever 46a of the input device 45 in the one-handed manner.

That is, the operation lever 46a is tilted in any specified direction and, depending on the tilted angle, the speed at which the sheath 52 is selectively inserted or pulled back and the speed of the therapeutic member 51 is selectively opened or closed can be changed on a controlled basis. The deeper the tilted angle of the operation lever 46a from the perpendicular position thereof, the faster the speeds of both inserting/pulling back the sheath 52 and opening/closing the therapeutic member 51.

As described, in the endoscope system 1 of the present embodiment, in order to a lesion 57 is displayed in endoscopic images on the display 124, an operator can handle the main operation portion 12c and switches 14 of the endoscope 10 in one hand, and, in parallel with this handling, in the other one hand, to not only grip the insertion tube 11 of the endoscope 10 but also manipulate the therapeutic member 51 by handling the input device 46 of the manipulating unit 45 hand-held together with the tube 11. Hence the distal section 11a of the insertion tube 11, which is placed in a body cavity of an object being examine, can surely be located near the lesion 57. And various combined operations such as an advancing and closing operations of the therapeutic member 51 can be conducted with ease. Though the flexible insertion tube 11 is subjected to peristaltic motions of body cavities, it is not necessary for an operator to release the insertion tube 11, with the therapeutic instrument 50 subjected to the various operations. Accordingly, with the lesion 57 always kept by the therapeutic images on the display 124, treatments can be done in a steadier and easier manner by using the therapeutic instrument 50. Such treatments include twisted motions characteristic of the insertion tube 11 of the medical endoscope 10. As a whole, using the endoscope system 1, time for the treatments can be reduced largely.

The present endoscope system 1 can work in combination with other types of medical therapeutic instruments including one which uses high-frequency power, like a third embodiment which will be detailed later. In such cases, operators are allowed to manipulate the therapeutic instrument 50 remotely from the manipulating unit 45 which is on hand. Hence it is possible to improve the operationally of the various switches, which have been regarded as being troublesome. More concretely, all necessary operations for holding the operating base holder 12, handling the knobs 15a and 15b, and handling the switches 14 for air supply, water supply and suction, and for various optical systems such as imaging and illuminating can be done in parallel with each other in one hand, different from the other band gripping the insertion tube together with the manipulating unit 45. This provides operational improvement in gaining use of various functions of the endoscope 10.

In consequence, according to the endoscope system 1 in the present embodiment, the insertion tube 11 can be gripped, together with the manipulating unit 45, to locate the desired distal section 11a in a body cavity, during which time the various functions of both the endoscope 10 and the therapeutic instrument 50 can be gained in an easier manner.

Second Embodiment

Referring to FIGS. 12-15 and 57, an endoscope system according to a second embodiment of the present invention will now be described. In this second embodiment, the identical or similar components in structures and/or functions to those in the first embodiment, the same reference numerals will be given for the sake of a simplified explanation. This way of explanation will also be applied to a third embodiment and subsequent embodiments and modifications.

Figure 12:
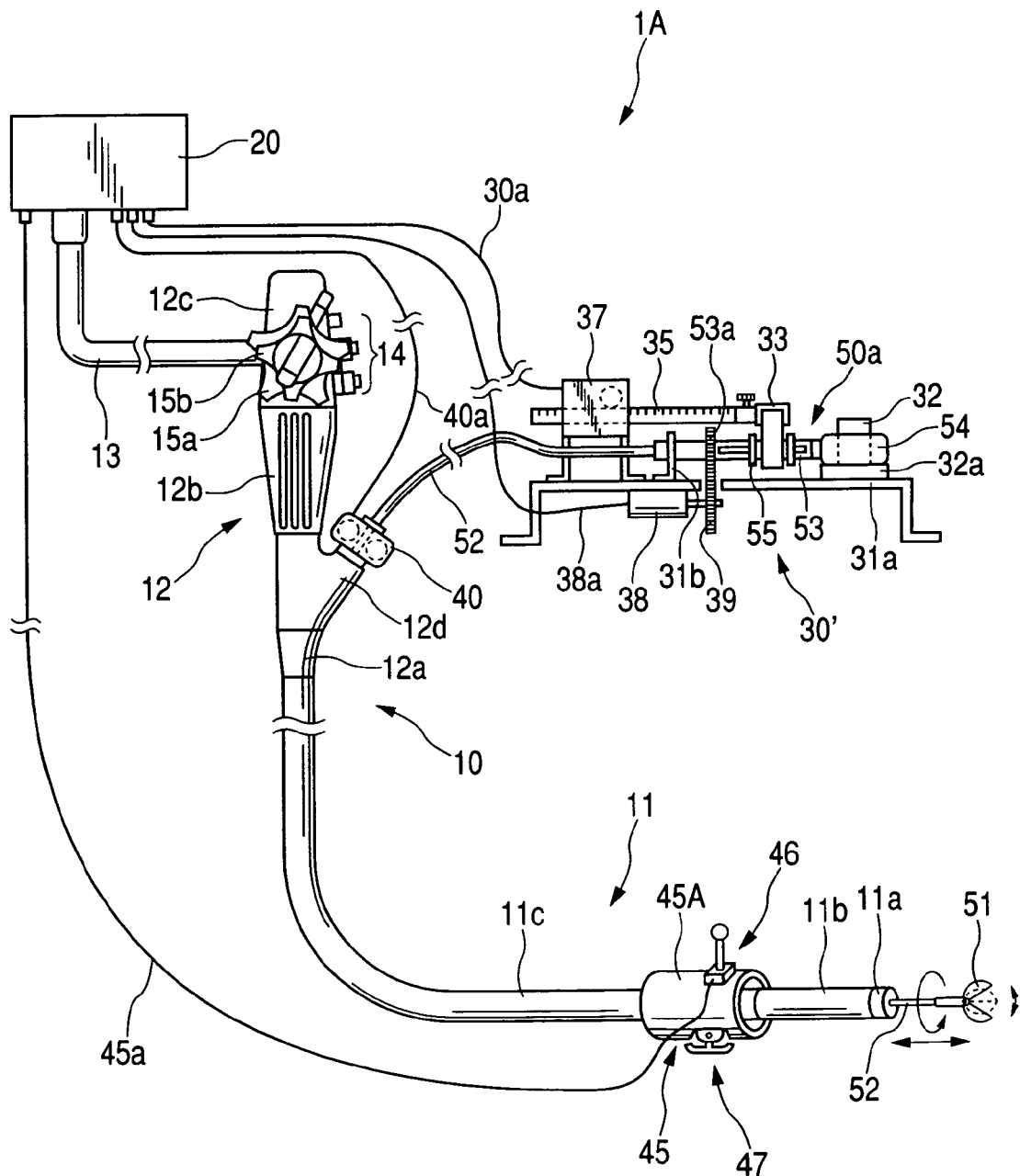
FIG. 12 is a schematic view showing the configuration of a main part of an endoscope system according to a second embodiment of the present invention.

As shown in FIG. 12, like the first embodiment, the endoscope system 1A according to the present embodiment is provided with an endoscope 10, a controller 20, an instrument operating unit 30', an instrument conveying unit 40, and a manipulating unit 45. The present embodiment is characteristic of having a therapeutic instrument 50a of which therapeutic member 51 is rotatable about the longitudinal axis of the sheath 52, together with the sheath 52. Such therapeutic instruments include a biopsy forceps.

In the present embodiment, the first drive unit according to the present invention is realized by the instrument operating unit 30', which operates the therapeutic instrument 50a in combination with the endoscope 10 and rotates both the sheath 52 and the therapeutic member 51 of the therapeutic instrument 50a. The instrument operating unit 30' is provided with a rotational motor 38 for rotating the sheath 52 and the member 51 about the longitudinal axis of the sheath 52. The second drive unit of the present invention is composed by the instrument conveying unit 40, like the first embodiment.

Figure 13:
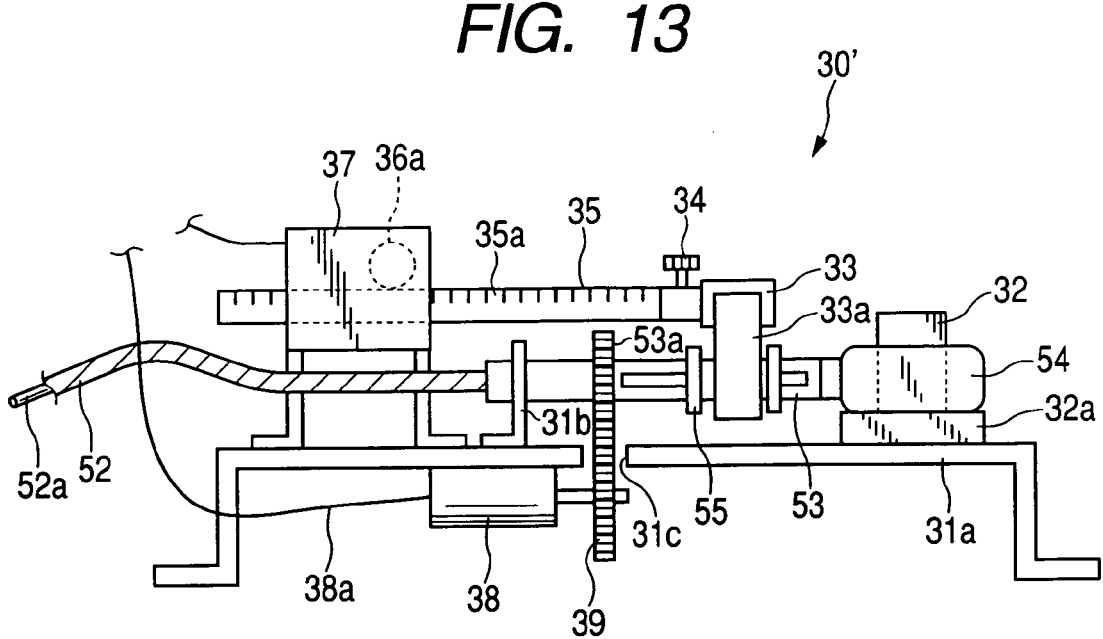
FIG. 13 is a side view showing an instrument operating unit employed by the endoscope system of the second embodiment.

Referring to FIG. 13, the instrument operating unit 30' will now be detailed.

The instrument operating unit 30', which functions as the first drive unit, is provided with an electric motor 38 which gives the rotary force to the part of the sheath 52. This electric motor 38 is provided with a rotation transferring gear (simply referred to as a gear) 39, and is electrically connected to the controller 20 via an electric cable 38a. This motor 38 is, as shown in FIG. 13, mounted on the rear side of the base body 31a of the instrument operating unit 30' which is shaped roughly similar to a hat.

In the base body 31a is formed a hole 31c so as to be enable a direct view toward the gear 39 of the electric motor 38 from the upper side of the base body on which the handling portion 53 of the instrument 50 is placed. Furthermore, the base body 31 is equipped with the supporting portion 31b for rotatably supporting the handling portion 53.

On the end of the handling portion 53 of the instrument 50, a passive gear (simply referred to as a gear) 53a is placed, and is engaged with the gear 39 which is come out from the surface of the base body 31a through the hole 31c.

Figure 14:
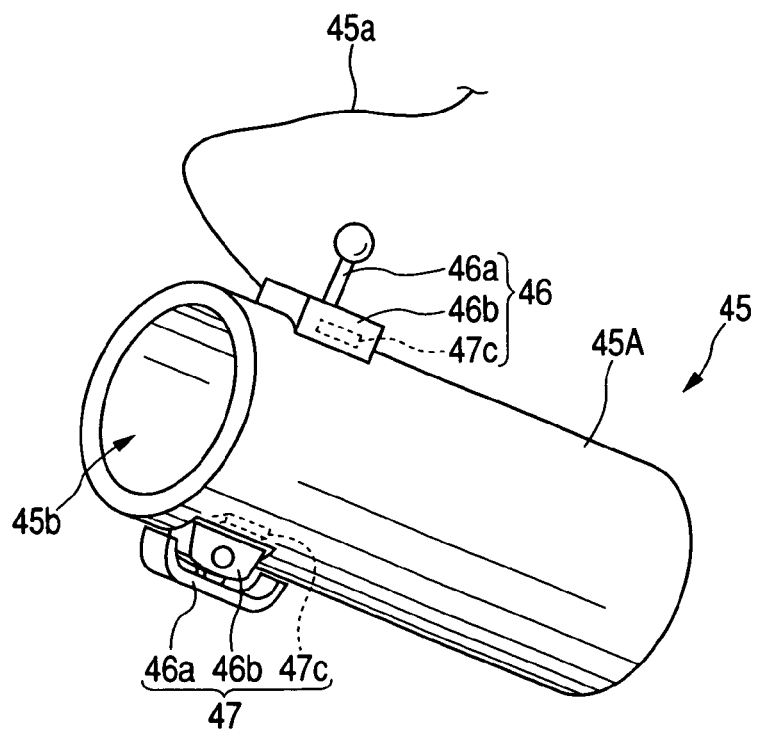
FIG. 14 is a perspective view showing a manipulating unit according to the second embodiment.

Referring to FIG. 14, the manipulating unit 45 will now be described.

According to the present embodiment, as shown in FIG. 14, the manipulating unit 45 is also provided with a rotation commanding device 47, which serves as one of the input devices. This rotation commanding device 47 is mounted on a side of the outer surface of the external loading tube 45A different from the side on which the input device 46 is mounted. That is, the input device 46 and the rotation commanding device 47 are mounted on and jutted from the outer surface of the external loading tube 45A in the mutually opposite directions.

This rotation commanding device 47 has a rotation commanding lever 47a, a lever supporter 47b which supports the rotation commanding lever 47a, and a detecting circuit 47c. Of these, the rotation commanding lever 47a is configured such that the lever 47a can be rotated about an axis perpendicular to the longitudinal axis of the manipulating unit 45. The detecting circuit 47c is formed to have trimmer resistors for electrically detecting a tilted state of the lever 47a and outputs an electric analog signal as a command signal.

The detecting circuit 47c is communicably connected to the controller 20 via the signal cable 45a, whereby the command signal is sent to the A/D converter 123a of the motor processor 123.

Figure 15:
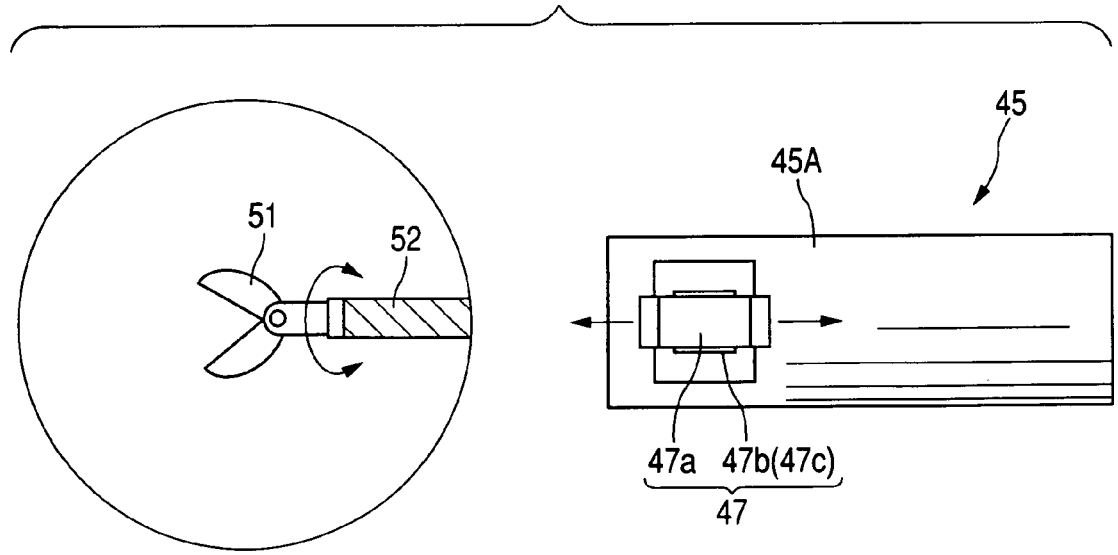
FIG. 15 exemplifies how to operate the manipulating unit.

To be more specific, as shown in FIG. 15, in the rotation commanding device 47, the rotation commanding lever 47a is tiled in the back and forth direction along the longitudinal axis of the manipulating unit 45. That is, the lever 47a is operated to rotate relatively to the lever supporter 47b. This operation results in the issuance of command signals to rotate the sheath 52 together with the therapeutic member 51. In the present embodiment, when the rotation commanding lever 47a is tiled forward, the detecting circuit 47c issues a command signal to rotate the sheath 52 (together with the therapeutic member 51) in a counterclockwise direction defined using the direction directing from the base end of the unit 45 to the distal end thereof. In contrast, when the rotation commanding lever 47a is tiled backward, the detecting circuit 47c issues a command signal to rotate the sheath 52 (together with the therapeutic member 51) in the clockwise direction.

Like the foregoing, the controller 20 is formed to process information indicative of two tilted states of the operation lever 46a in both the back and forth direction and the lateral direction and one tilted state of the rotation commanding lever 47a in the back and forth direction.

Accordingly, an operator inspects a body cavity with viewing endoscopic images, during which time, if a lesion is found, the operator treats the lesion by cutting out the lesion, for instance. A detailed explanation will now be given on the assumption that the therapeutic instrument 50a is a biopsy forceps.

Like the first embodiment, an operator can use, for example, the thumb to handle the input device 46 of the manipulating unit 45, which is gripped by the operator together with the insertion tube 11. By this handling, the sheath 52 of the therapeutic instrument 50a can be inserted and pulled back and the therapeutic member 51 can be opened on closed on demand. Additionally, the operator can use, for example, the first finger to handle the rotation commanding device 47, thus making it possible to rotate the sheath 52 about the longitudinal axis thereof.

Specifically, in response to a tilt of the rotation commanding lever 47a in either the forward direction or the backward direction, a drive signal in compliance with a tilted angle of the lever 47a is fed to the motor 38 mounted in the instrument operating unit 30'. In other words, via the signal cable 30a, the motor 38 is powered to rotate in a specified rotational direction at a specified rotational speed. The rotation of the motor 38 allows the gear 39 to rotate in a specified direction. The rotation of this gear 39 is transmitted, via the gear 53a, to the sheath 52 of the therapeutic instrument 50a which is inserted in the therapeutic-instrument channel 11CH. Hence the sheath 52 is forced to rotate about its longitudinal axis.

The rotational force given to the sheath 52 is transmitted to the therapeutic member 51 located at the distal end of sheath 52, rotating this member 51 in the specified rotational direction. That is, in the present example, a forward tilt of the rotation commanding lever 47a enables the sheath 52 to rotate in a counterclockwise direction defined by observing the unit 45 from its base end to the distal end. By contrast, a backward tilt of the rotation commanding lever 47a enables the sheath 52 to rotate in the clockwise direction. How to assign the tilt directions to the rotation commanding lever 47a and the rotational directions to the sheath 52 and therapeutic member 51 may be changed to the opposite one to the above.

As a result, an operator is able to tilt the operation lever 46a in the forward, backward, rightward, or leftward direction to perform the open or close motion of the therapeutic member 51 or the inserting or pulling back motion of the sheath 52, and concurrently with or in parallel with such an operation, the operator is also allowed to tilt the rotation commanding lever 47a in the forward or backward direction to rotate the therapeutic member 51.

Figure 56:
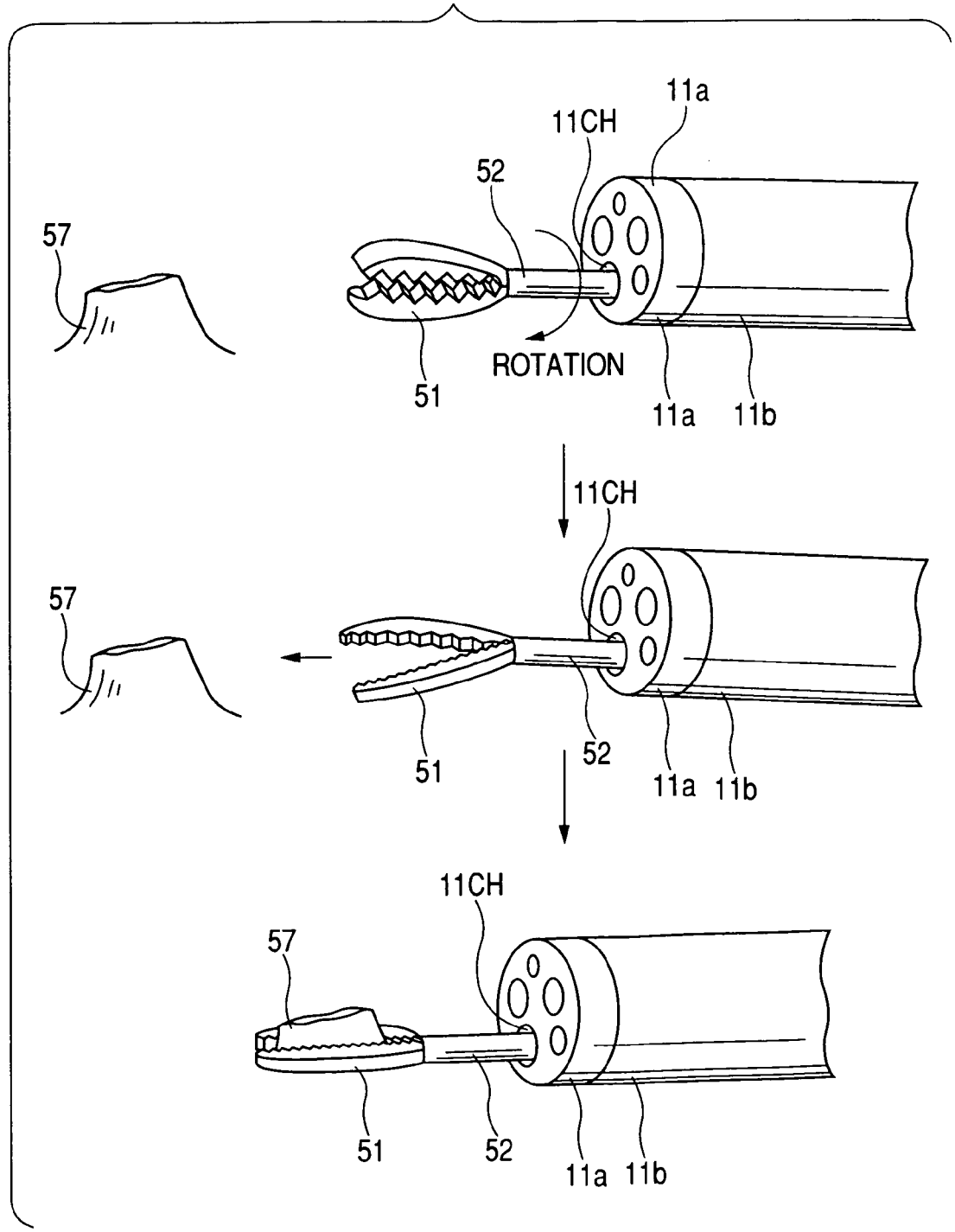
FIG. 56 explains the functions of a therapeutic instrument employed in the second embodiment.

Thus, as shown in FIG. 56, even if the lesion 57 is located such that the direction of the therapeutic member 51 (i.e., the biopsy forceps) toward the lesion 57 is shifted from the initial one, this shifted direction can be compensated. Namely, the operator makes not only the rotation commanding lever 47a tilt backward but also the operation lever 46a tilt forward, so that the therapeutic member 51 can be made to advance toward the lesion 57 as the member 51 rotates during the advancement.

Further, in the present embodiment, depending on a tilted angle of the rotation commanding lever 47a, the speed of rotation of both the sheath 52 and the therapeutic member 51 can be adjusted as well. As the tilted angle of the lever 47a from its initial standing position becomes larger, the speed of the rotation increases.

Therefore, as described, the endoscope system 1A according to the present embodiment provides the identical advantages to those obtained in the first embodiment and, besides those, provides an advantage that the therapeutic member 50a that needs the rotational motions can be used, in addition, the rotation commanding device 47 is located to be opposed to the input device 46 in a symmetrical form with the external loading tube 45A therebetween, which permits operators to handle both devices 46 and 47 in one hand at the same time, while still gripping the insertion tube 11 as well by the same one hand.

In addition, an operator can make full use of both hands in such a manner that, for example, the input device 46 is handled by the right hand and the rotation commanding device 47 and the various buttons and switches (for bending, air supply, water supply, and others) of the endoscope 10 are handled by the left hand. This is because the operations to convey the sheath 52 and open/close the therapeutic member 51 is relatively frequently needed, but the rotation of the therapeutic member 51 is relatively lower in frequency of use. Of course, the operational setting to both hands may be opposite to each other.

Third Embodiment

Figure 16:
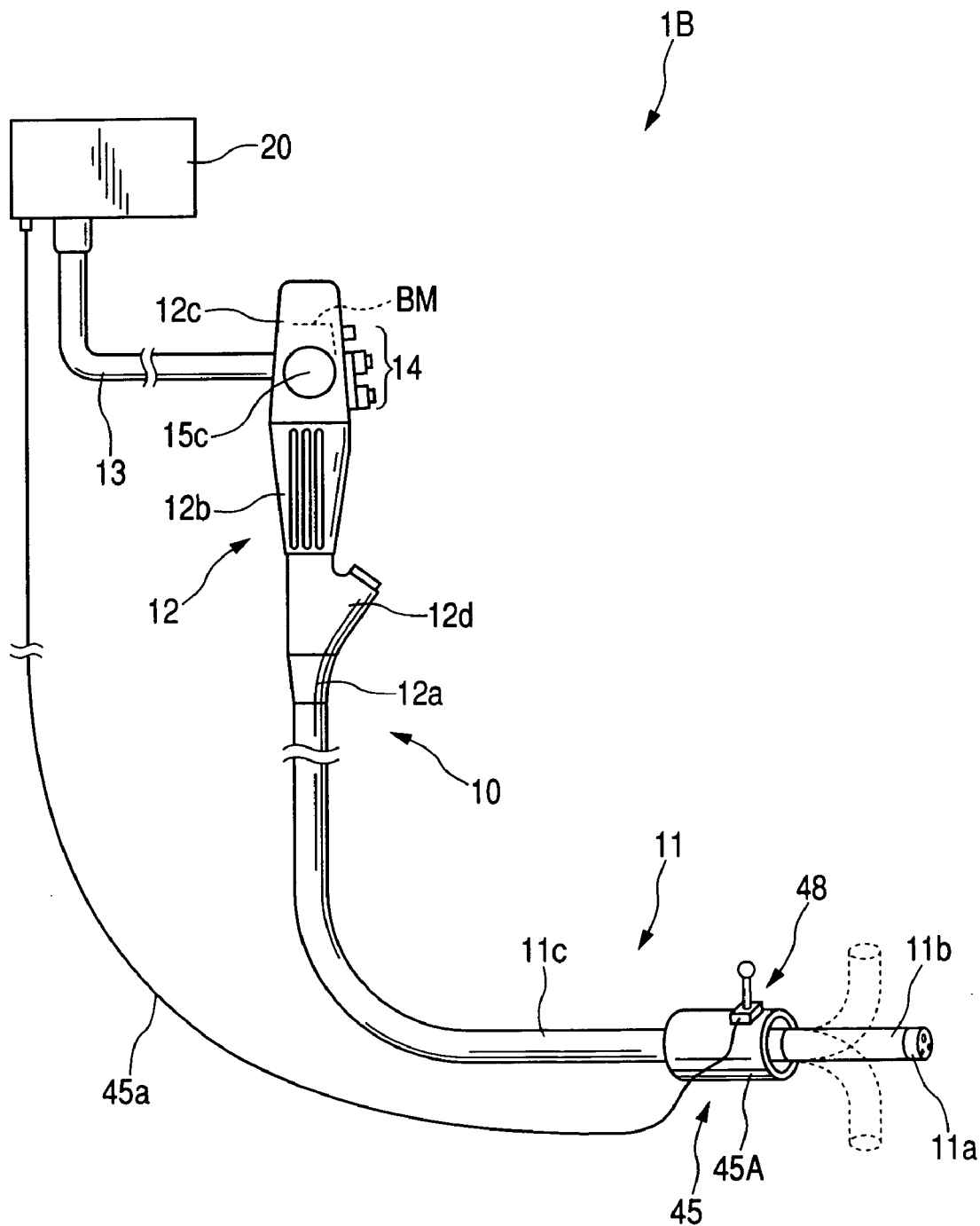
FIG. 16 is a schematic view showing the configuration of a main part of an endoscope system according to a third embodiment of the present invention.
Figure 17:
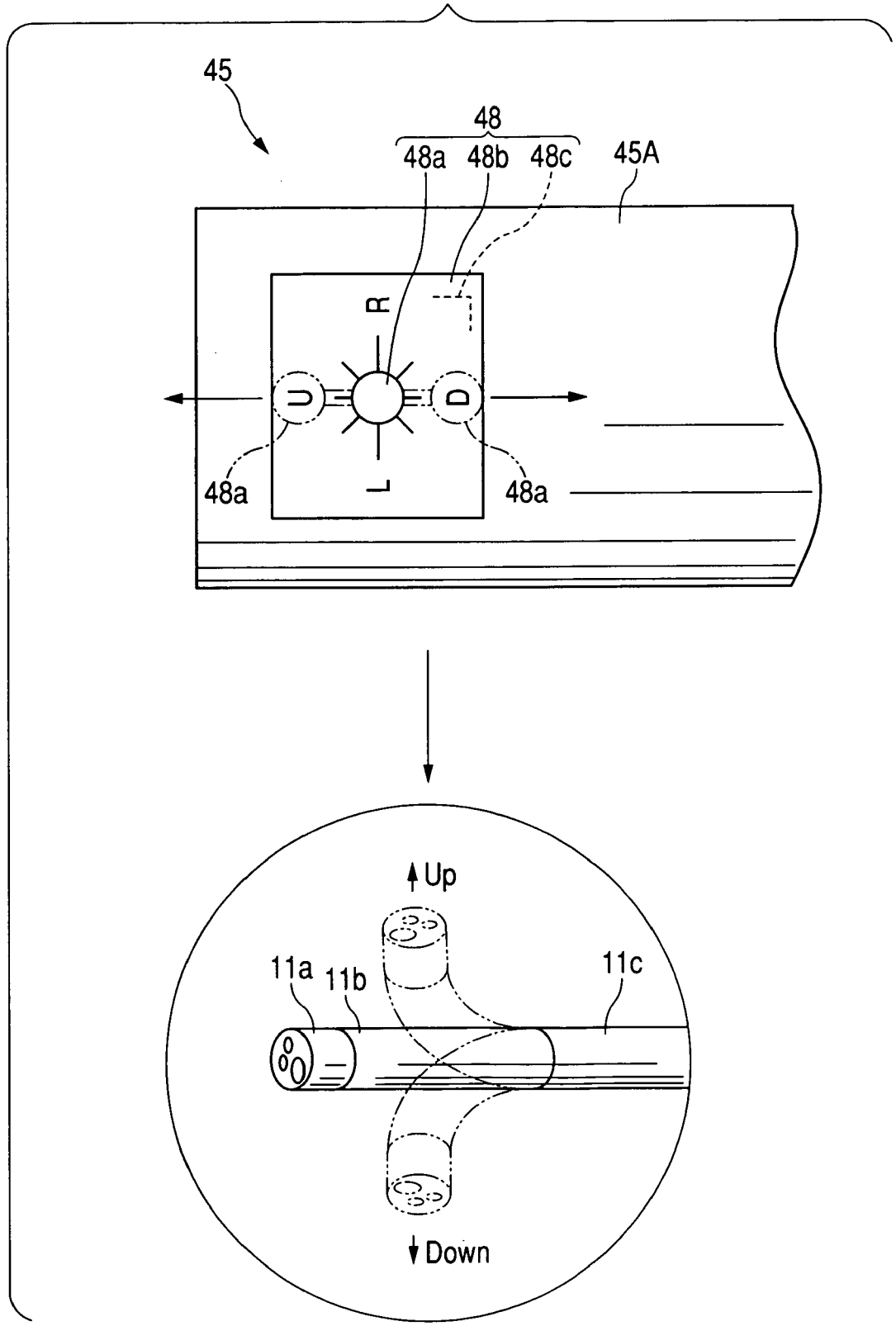
FIG. 17 explains how to bend a bendable section of an insertion tube of an endoscope using a manipulating unit in the third embodiment.

Referring to FIGS. 16 and 17, a third embodiment of the endoscope system according to the present invention will now be so described.

As shown in FIG. 16, an endoscope system 1B in the present embodiment is provided with an endoscope 10, a manipulating unit 45, and a controller 20. The endoscope 10 is formed as an endoscope that comprises the main operation portion 12c with an electrically driven bending mechanism BM (not shown in detail) for bending the bendable section 11b in an electrically powered manner and a trackball 12c for commanding the operations of the mechanism BM.

Further, the endoscope 10 is provided with the instrument inserting portion 12d that is a guide for the therapeutic-instrument channel 11CH. Thus a desired type of therapeutic member can still be used by inserting the therapeutic member through the channel 11CH.

The manipulating unit 45 is equipped with a bending command device 48 functions as an input device, instead of the input device 46 described in the first embodiment, and the bending command device 48 is communicably linked with the controller 20 via the signal cable 45a. The manipulating unit 45 and the controller 20 compose an apparatus for assisting endoscopic operations in the present endoscope system 1B.

As shown in FIG. 17, the bending command device 48 is equipped with a bending operation lever 48a, a lever supporter 48b, and a detecting circuit 48c and mounted at a position near the distal end of the manipulating unit 45. On the lever supporter 48b, there are printed directional markings indicative of bending command directions of the bendable section 11b. The directional markings show four bending ways defined relatively to the inserted direction of the insertion tube, which consist of a bending upward direction UP, a bending downward direction DOWN, a bending rightward direction RIGHT and a bending leftward direction LEFT. Capital letters U, D, R and L are put on the lever supporter 48b such that the letter U is on the distal end side, D on the base end side, R on the right end side, and L on the left end side when looking down on the lever supporter 48b.

Setting is made such that, as shown in FIG. 17, when the bending operation lever 48a is tilted by an operator toward the marking U on the lever supporter 48b, the bendable section 11b of the endoscope 10 is bent upward (UP), that is, is bent upward in currently acquired endoscopic images. In contrast, when the bending operation lever 48a is tilted by an operator toward the marking D, the bendable section 11b is bent downward (DOWN), that is, is bent downward in currently acquired endoscopic images. Though not shown in FIG. 17, when the bending operation lever 48a is tilted by an operator toward the marking R or L, the bendable section 11b is also bent rightward or leftward, that is, is bent rightward or leftward in currently acquired endoscopic Images, respectively.

Setting about the bending command device 48 is also made such that the device 48 has four intermediate directional ranges sectioned by the four markings U, D, R and L, respectively, on the lever supporter 48b and tilting toward the respective intermediate directional ranges makes it possible that the bendable sections 11b is subjected to bending operations upward or leftward and rightward or leftward simultaneously. In these operations, depending on a tilted angle of the bending operation lever 48a, it is configured that the bending angle of the bendable section 11b can be adjusted. The deeper the tilted angle from its initial position, the larger the bending angle of the bendable section 11b.

The detecting circuit 48c detects the tilted angle of the lever 48a and outputs an electric signal as a bending command signal depending on the tilted angle. The detecting circuit 48c is connected to the controller 20 via the signal cable 45a to provide the bending command signal. On the similar manner to the foregoing embodiments, the controller 20 responds to the bending command signal to supply a drive signal to the bending mechanism BM of the endoscope 10 via the universal code 13. Hence the bending mechanism BM is driven on the bending command signal, so that the bendable section 11b can be bent in either specified direction.

As described, the endoscope system 1B according to the present embodiment, an operator, such as a doctor, is able to grip the manipulating unit 45, which is on hand, together with the insertion tube 11 and handle the unit 45 by the same hand gripping both the unit 45 and the insertion tube 11. In this gripping state, it is possible to operate the bending operations of the bendable section 11b, which belong to the functions 6f the endoscope 10. In the present embodiment, the endoscopic functions to be assigned to the manipulating unit 45 will not be limited to the foregoing bending operations, but may be assigned to other endoscopic functions, such as optical systems, air supply, water supply, and suction. Switches and buttons for such endoscopic functions may be mounted to the manipulating unit 45.

Alternatively, it is possible that the bendable section 11b responds to only the manual operations at the manipulating unit 45, with no response to the operations at the trackball 15c of the main operation portion 12c. Still alternatively, it is also possible that the bendable section 11b responds to the manual operations at both the manipulating unit 45 and the trackball 15c. It is also possible that the bendable section 11b responds to only the bending upward and downward operations at the manipulating unit 45, because such operations are needed frequently. Further, the controller 20 may be configured to cope with a separate commanding way that commands for the upward and downward bending motions and commands for the rightward and leftward bending motions are issued mutually separately from the manipulating unit 45 and the trackball 15c.

Fourth Embodiment

Figure 18:
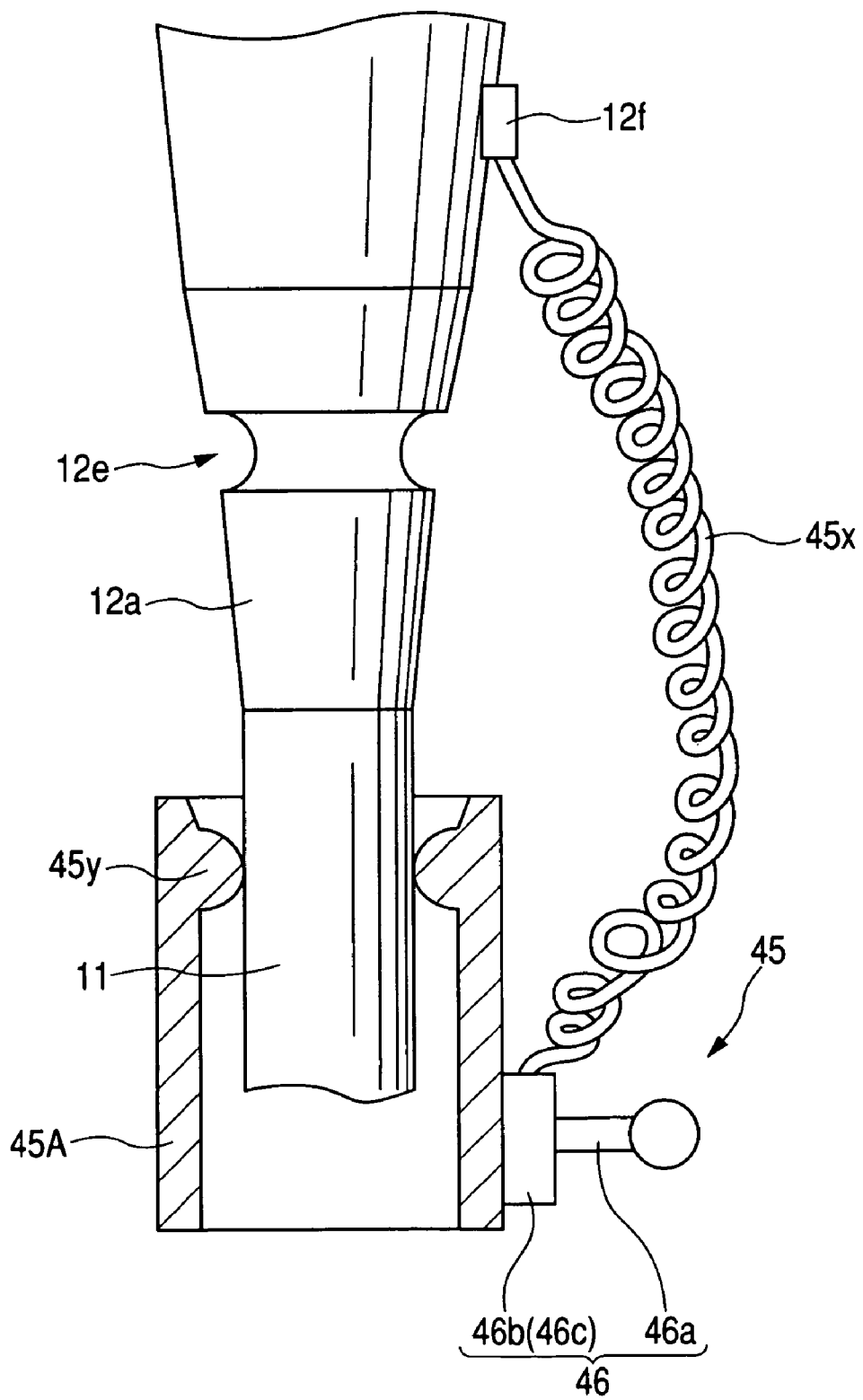
FIGS. 18 and 19 is partial side views each explaining the insertion tube in the forth embodiment.
Figure 19:
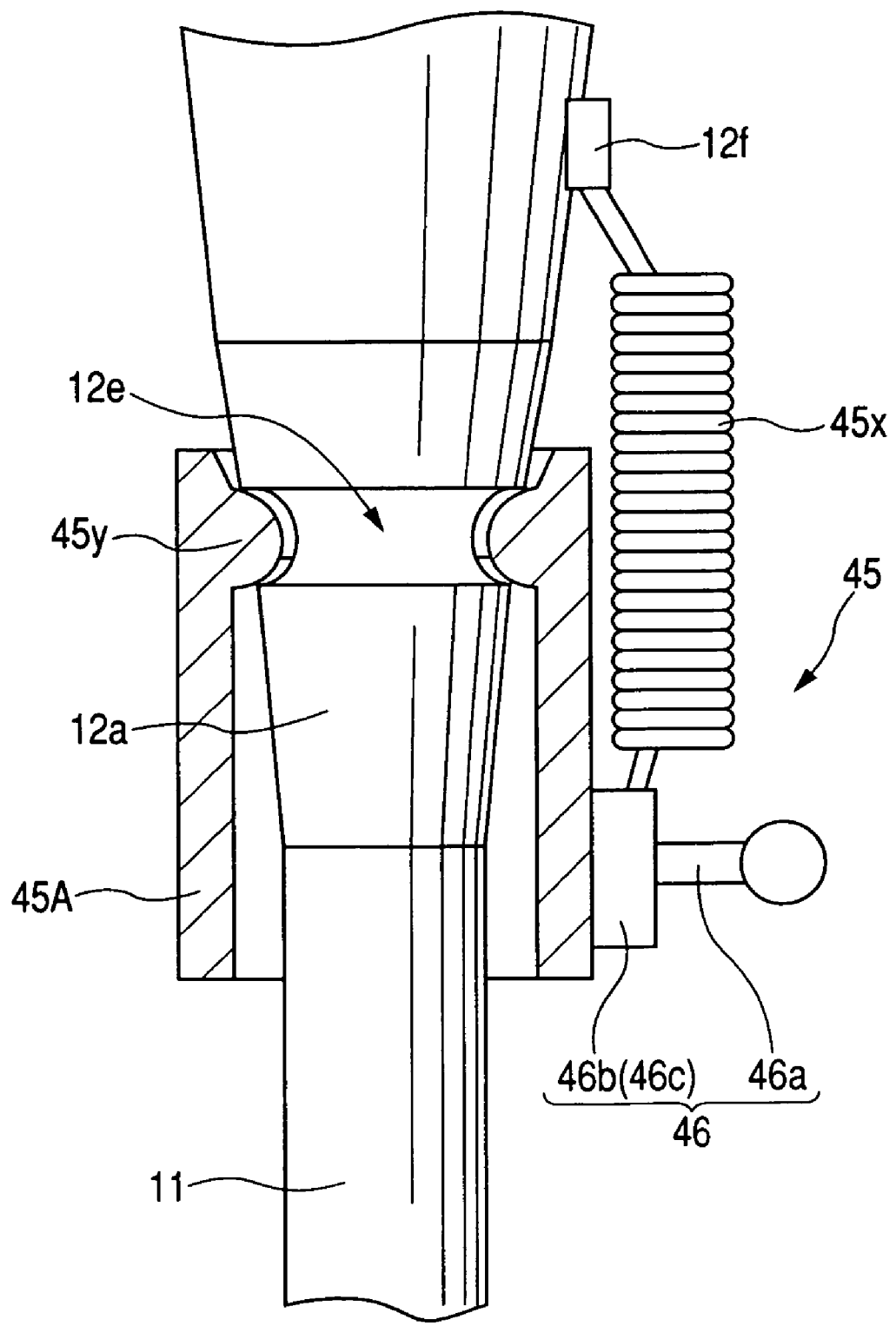

Referring to FIGS. 18 and 19, a fourth embodiment of the endoscope system according to the present invention will now be described.

The present embodiment relates to holding means for holding the manipulating unit 45 at the base end of the insertion tube 11 of the endoscope 10. In the following, the manipulating unit 45 adopts the same configuration as that descried in the first embodiment, but may adopt those described in the second and third embodiments.

As shown in FIGS. 18 and 19, on the inner surface of the external loading tube 45A of the manipulating unit 45, an engaging protrusion 45y serving as engaging means is formed to protrude therefrom at a position near the base-side end of the tube 45A. In this manipulating unit 45, an electric cable 45x extended from the lever supporter 46b is made up of a coil type of signal cable.

The signal cable 45x has a cable end detachable to a connecting terminal 12f secured on the operating base holder 12 of the endoscope 10. The connecting terminal 12f is electrically connected to an electric cable (not shown) passing in the holder 12, and the not-shown electric cable is handed to the universal code 13 (refer to FIG. 1), before being routed to the controller 20 for an electric connection.

Thus, the command signals from the manipulating unit 45 is transmitted from the detecting circuit 46c in the lever supporter 46b to the controller 20 via the coil type of cable 45x, connecting terminal 12f, not-shown electric cable in the holder 12, and universal code 13.

Further, on the bending-block base portion 12a coupled with the base end of the insertion tube 11, an engaging recess 12e formed into a groove in the circumferential direction of the portion 12a. This engaging recess 12e is along the circumferential direction and functions as engaging means. As shown in FIG. 19, the engaging protrusion 45y is fit in this engaging recess 12e, whereby the endoscope 10 and the manipulating unit 45 are linked together using engaging means composed of the engaging protrusion 45y and the engaging recess 12e.

Therefore, an operator is able to detachably attach the manipulating unit 45 to the bending-block base portion 12a, so that the manipulating unit 45 can be held at the bending-block portion 12a if the unit 45 is not used. It is therefore unnecessary for the operator to grip the manipulating unit 45 in inserting/pulling back the insertion tube 11 into or from a body cavity of an object. That is, the manipulating unit 45 does not become an obstacle to the operations, making it easier to operate the insertion tube 11. Whenever necessary, the operator detaches the manipulating unit 45 from the bending-block base portion 12a and shifts the manipulating unit 45 at a desired position for gripping it together with the insertion tube 11.

In addition, the manipulating unit 45 is subjected to a pulling force exerted in a direction toward the base end of the insertion tube 11, so that the unit 45 is moved toward the base end if an operator releases the manipulating unit 45. Thus, in cases where the operator releases the manipulating unit 45, this unit 45 is obliged to position on the base end side of the insertion tube 11, farther than the position of the hand gripping the insertion tube 11. Operational performance for making the insertion tube 11 re-approach the body cavity can be improved. Further, using the cable 45x making it possible that the manipulating unit 45 is prevented from dropping off from the insertion tube 11, when this insertion tube 11 is pulled out from the body cavity.

Fifth Embodiment

Figure 20:
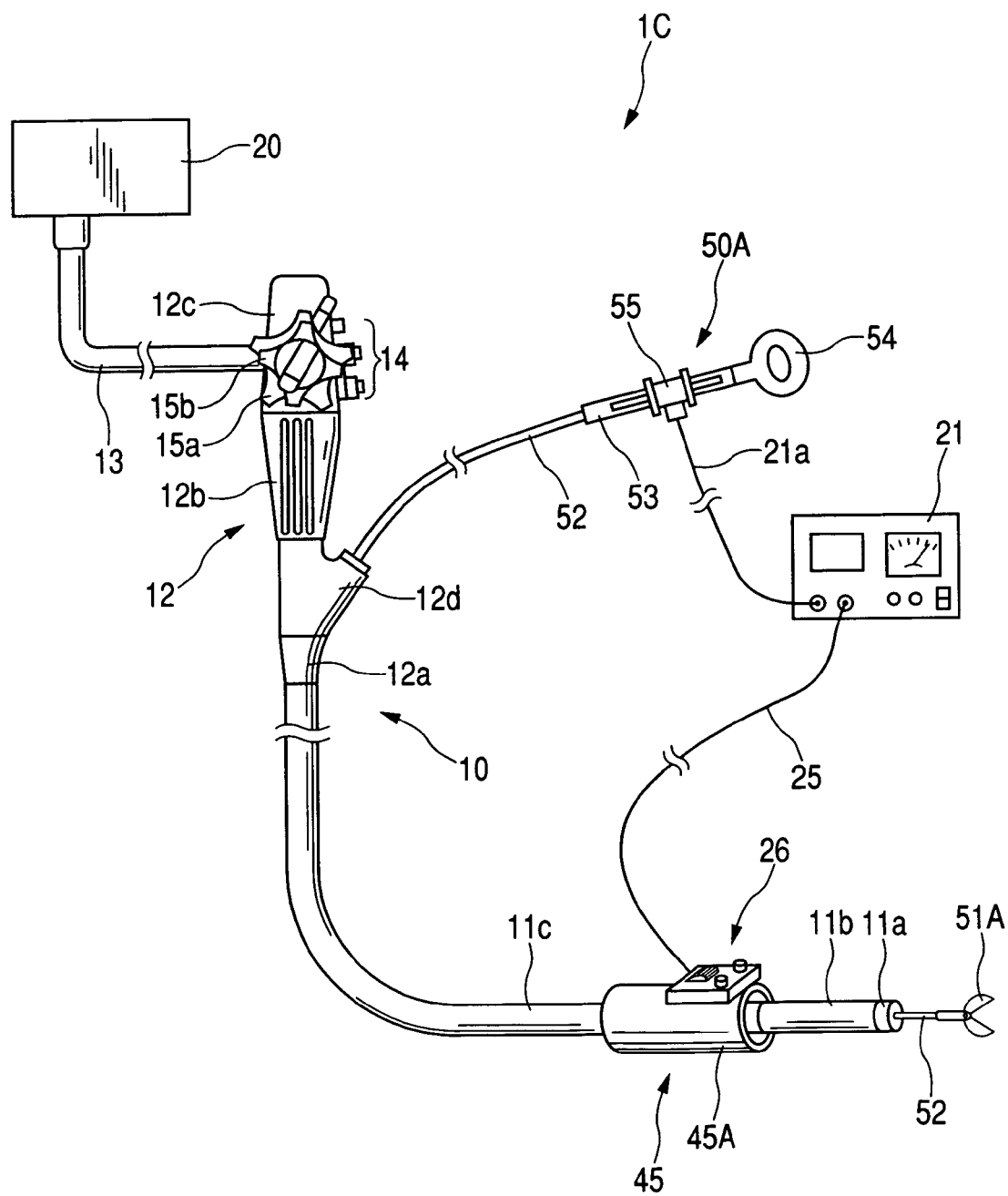
FIG. 20 is a schematic view showing the configuration of a main part of an endoscope system according to a fifth embodiment of the present invention.
Figure 21:
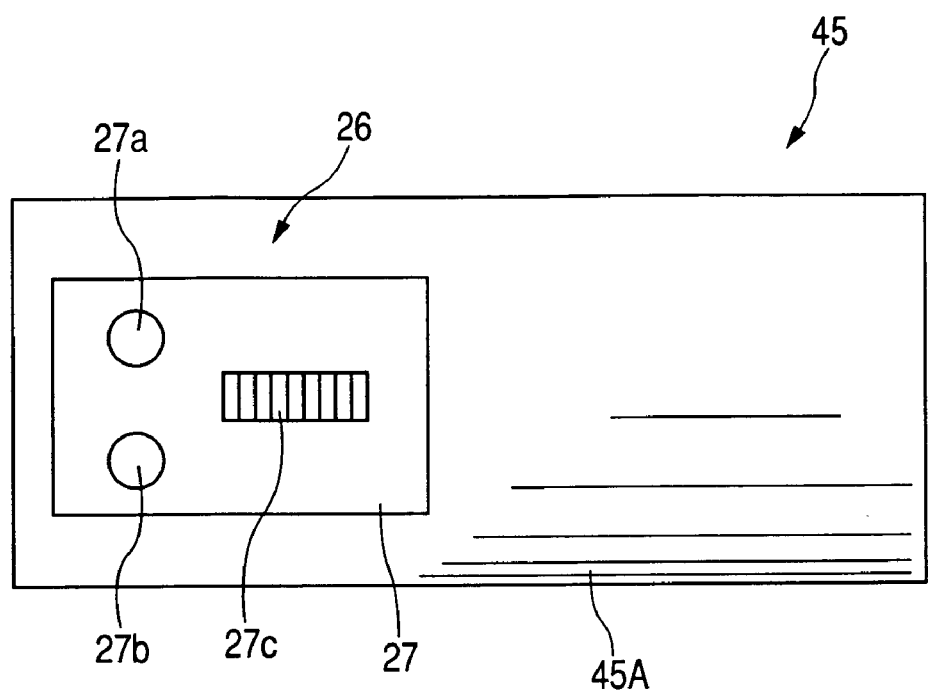
FIG. 21 is a plan view showing a manipulating unit employed in the fifth embodiment.
Figure 22:
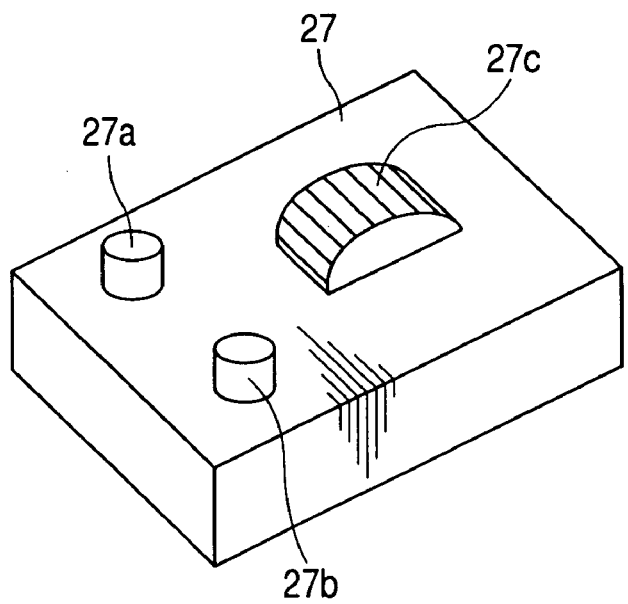
FIG. 22 is a perspective view of the manipulating unit.

Referring to FIGS. 20-22, a fifth embodiment of the endoscope system according to the present invention will now be described.

As shown in FIG. 20, the endoscope system IC of the present embodiment is provided with an endoscope 10, controller 20, and a manipulating unit 45 serving as an apparatus for assisting the endoscopic operations. In the endoscope system 1C, a therapeutic instrument 50A for applying high-frequency therapy to lesions in a body cavity, such as high-frequency surgical snare, hot biopsy forceps, and cautery knife, can be used. In the following, as the therapeutic instrument 50A, the hot biopsy forceps is exemplified.

The therapeutic instrument 50A, which is a hot biopsy forceps, is inserted through the therapeutic-instrument channel 11CH from the instrument inserting portion 12d of the endoscope 10, like the first embodiment. The therapeutic instrument 50A is equipped with a handle 53 arranged at the base end of a finger-engaging ring 54, a slider 55, and a therapeutic member 51A. The slider 55 moves forward and backward along the axis of the handle 53, thereby pulling and relaxing the operating wire 52a in the sheath 52. The therapeutic member 51A, which is arranged at the distal end of the sheath 52, is formed into an alligator-grip member that can be opened and closed in pulling and relaxing the operating wire 52a.

A high-frequency electric code 21a is connected to the metal-made operating wire 52a in the sheath 52 via the slider 55, thus realizing an electrical connection with the therapeutic member 51A. From the slider 55, the high-frequency electric code 21a extends to a high-frequency power supply 21 for supplying high-frequency power.

The high-frequency power supply 21 is electrically connected to the high-frequency power supply 21 via the cord 21a to supply high-frequency power thereto and also electrically connected to the manipulating unit 45 to receive command signals therefrom.

The manipulating unit 45 is provided, like the foregoing embodiments, an external loading tube 45A externally loaded to the insertion tube 11 and an input device 26 serving as a high-frequency output switch arranged on the tube 45A on a distal-end side thereof.

As shown in FIGS. 21 and 22, this input device 26 comprises a device body 27 and a coagulation switch 27a, a cutting-out switch 27b, and an output setting switch 27c which are arranged in the device body 27.

The coagulation switch 27a is used to heat and coagulate a lesion in a body cavity by the use of the therapeutic member 51A. The cutting-out switch 27b is for heating and cutting out a lesion in a body cavity using the therapeutic member 51A. Further, the output setting dial 27c is a tool to be operated for adjusting a high-frequency output from the high-frequency power supply 21.

As can be understood from the above, in the present endoscope system 1C, an operator can grip the manipulating unit 45 together with the insertion tube 11 and use them. In such use, commands the power supply 21 to supply the high-frequency power to the therapeutic member 50A can be generate by handing the manipulating unit 45 in one hand.

In this way, the present endoscope system 1C provides not merely the almost identical advantages to those obtained in the foregoing embodiments but also an advantage that the therapeutic instrument 50A on the high-frequency power, such as hot biopsy forceps, can be used by the present system 1C. Of course, the therapeutic instrument 50A is not limited to the hot biopsy forceps, but may adopt other tools such as high-frequency surgical snare and cautery knife.

In addition, an operator can make full use of both hands in such a manner that, for example, the input device 46 is handled by the right hand and the input device 26 and the various buttons and switches (for bending, air supply, water supply, and others) of the endoscope 10 are handled by the left hand. This is because the operations to convey the sheath 52 and open/close the therapeutic member 51A is relatively frequently needed, but cutting-out operations on the high-frequency power supply to the therapeutic member 51A is relatively lower in frequency of use. Of course, the operational setting to both hands may be opposite to each other.

Modifications

Various modifications concerning with the manipulating unit 45 will now be explained, which are still applicable to the foregoing various embodiments.

(First Modification)

Referring to FIGS. 23-26, a first modification of the manipulating unit will now be described.

Figure 23:
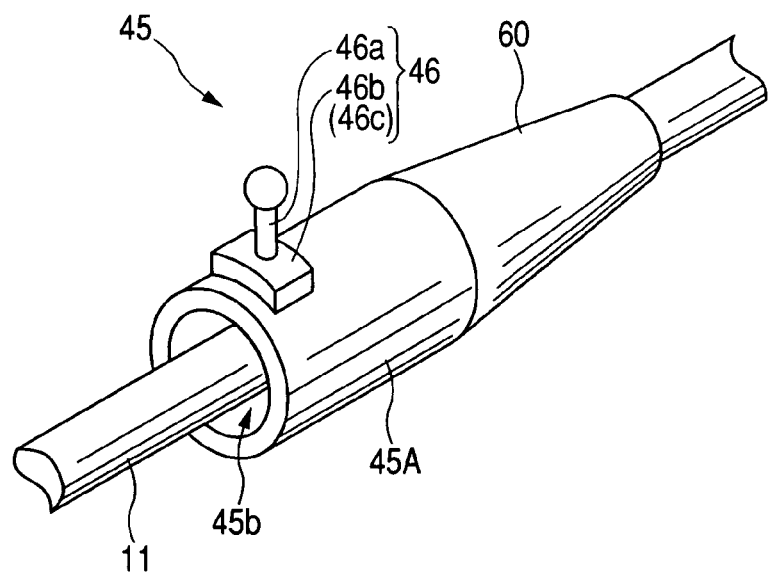
FIG. 23 is a perspective view showing a manipulating unit according to a first modification of the present invention, the manipulating unit being loaded to an insertion tube of an endoscope.

As shown in FIG. 23, a manipulating unit 45 is equipped with an external loading tube 45A and a soft cylindrical grip 60, which is made of elastic materials having high frictional resistance, such as rubber (including silicon and urethane) or synthetic resin (including various types of elastomer). The grip 60 is loaded to the base end of the tube 45A. That is, the input device 46 is also arranged to the external loading tube 45A at a distal-end side position on the tube 45A.

The grip 60 is a longitudinal through-hole of which diameter is larger than the outer diameter of the insertion tube 11, resulting in that the insertion tube 11 is inserted freely through the grip 60.

Figure 24:
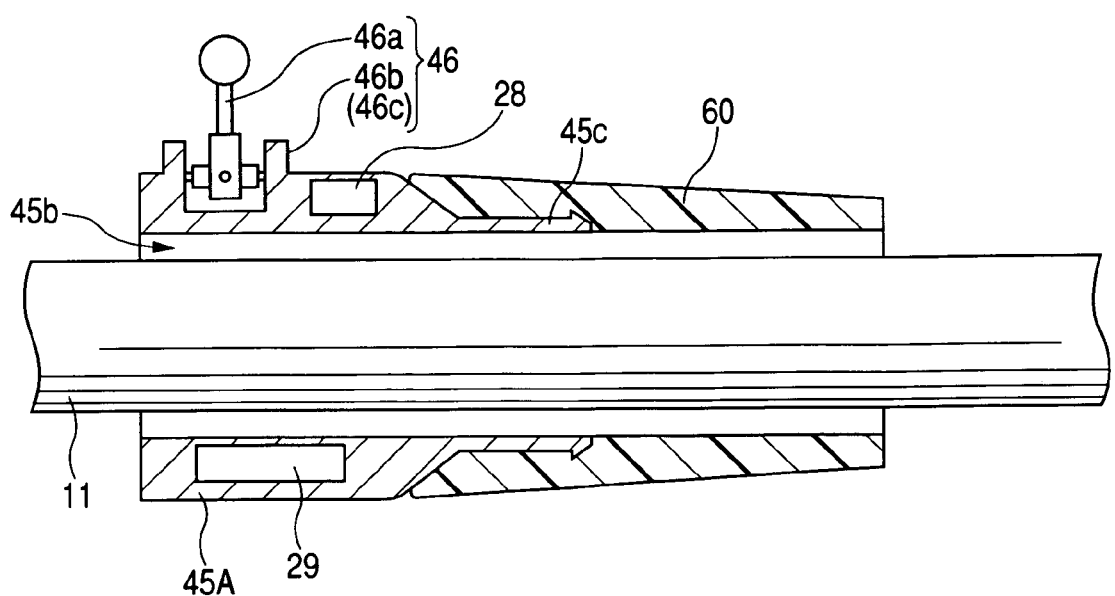
FIG. 24 is a longitudinal sectional view showing the manipulating unit loaded to the insertion tube.

The external loading tube 45A has a two-staged outer surface of which diameter on the base end side is smaller than that on the distal end side. Part of the smaller-outer diameter portion on the base end side is formed as a grip loaded portion 45c having a protrusion, as shown in FIG. 24. This grip loaded portion 45c is inserted into a distal end portion of the grip 60 to be hooked therein thanks to an elastic deformation of the distal end portion, thereby establishing a linkage between the tube 45A and the grip 60. In this linked state, the protrusion of the grip loaded portion 45c is cut into the inner wall of the grip 60, whereby the grip 60 is avoided from dropping off from the tube 45A.

The manipulating unit 45 is also provided with a transmitter 28 and a battery 29, both of which are embedded in the external loading tube 45A. The transmitter 28 contains a detecting circuit (not shown) to output a command signal responding to detection of operations at the operation lever 46a and is powered by the battery. In response to manual operations at the operation lever 46a, the transmitter 28 transmits a command signal to the controller 20 (refer to FIG. 1) by wireless. In this configuration, though not shown, the controller 20 has an antenna and a receiver for receiving the command signal from the transmitter 28.

In the present modified configuration, when an operator grips the manipulating unit 45 with a hand, the grip 60 is elastically deformed so that its inner surface comes into tight contact with the outer surface of the insertion tube 11. The friction force exerted between the grip 60 and the insertion tube 11 due to the tight contact therebetween avoids a shift between the manipulating unit 45 and the insertion tube 11, providing a easy-to-grip means therefor.

Since the manipulating unit 45 is operable by wireless, an electric cable to the controller 20 is unnecessary, thus facilitating the slide operation of the manipulating unit 45 to the insertion tube 11.

Figure 25:
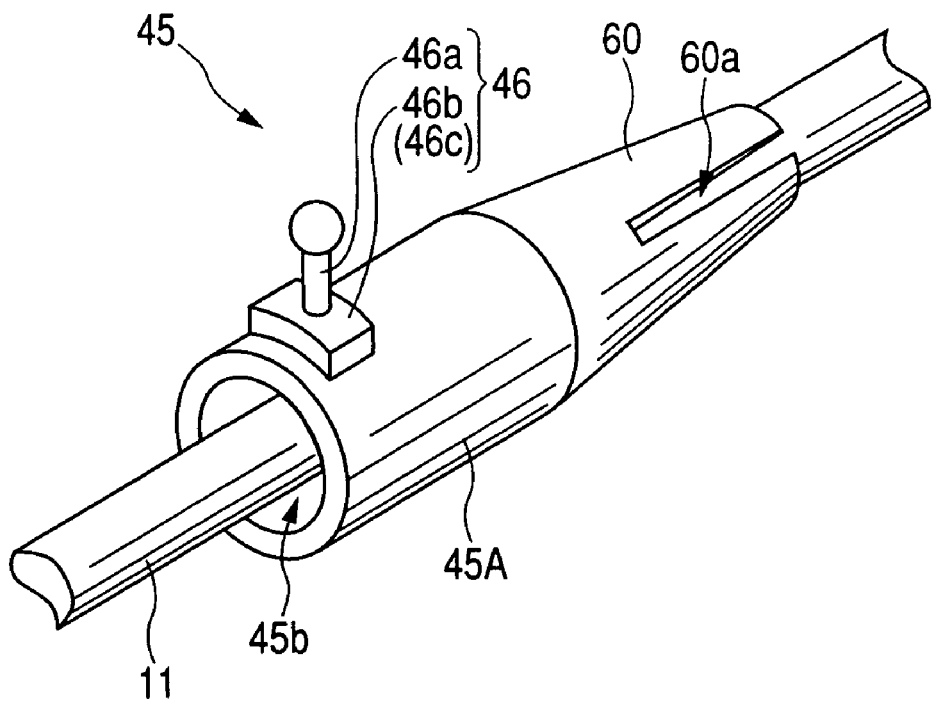
FIG. 25 is a perspective view showing a modified manipulating unit which can be loaded to the insertion tube.
Figure 26:
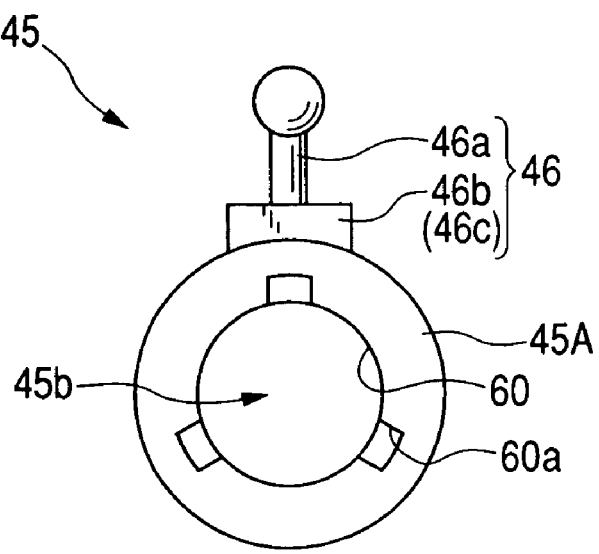
FIG. 26 is a rear view of the manipulating unit shown in FIG. 25, which is seen from the base end side of the insertion tube.

The grip 60, which is made of soft material, may have one or plural slits 60a, as shown in FIGS. 25 and 26. By way of example, three slits 60a are formed from the base end of the grip 60 to a middle point thereof along its longitudinal direction. As shown in FIG. 26, the three slits 60a are formed at angular intervals.

Forming such slits 60a along the grip 60 facilitates a tight contact between the grip 60 and the insertion tube 11, increasing the gripping force helping the operator's grip. The number of slits 60a may be set to any number.

(Second Modification)

Referring to FIGS. 27-30, a second modification of the manipulating unit will now be described.

Figure 27:
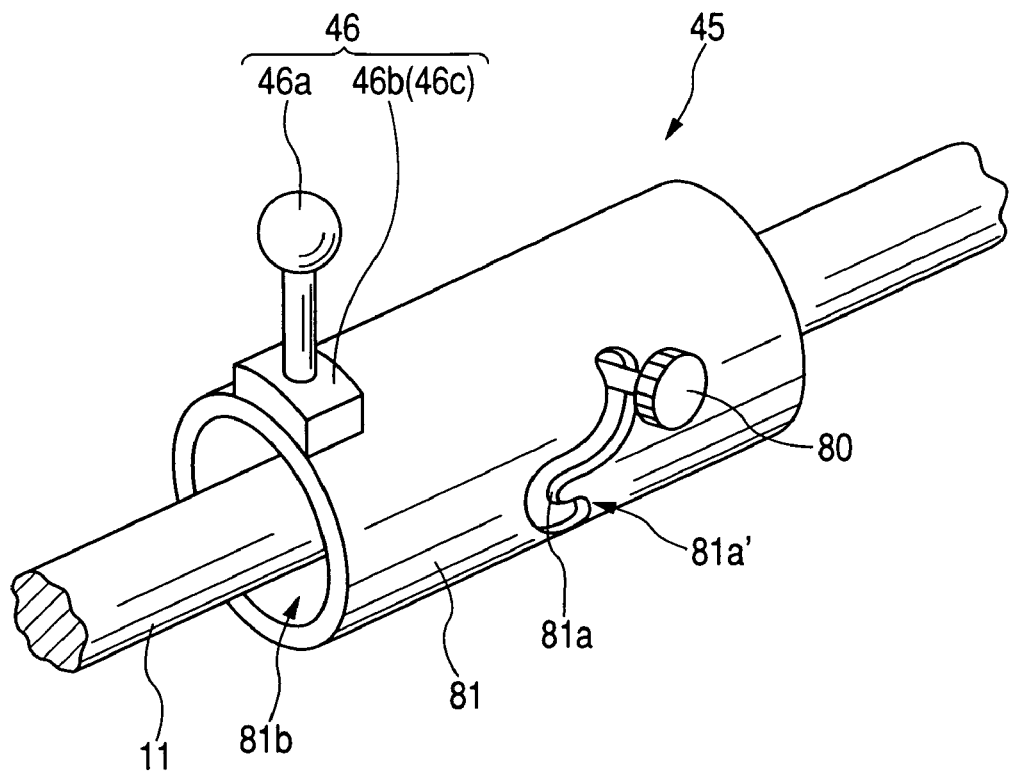
FIG. 27 is a perspective view showing a manipulating unit according to a second modification of the present invention, the manipulating unit being loaded to an insertion tube of an endoscope.

As shown in FIG. 27, a manipulating unit 45 is equipped with a cylinder 81 serving as a cam frame on which an input device 46 is formed. A cam slot 81a is formed in the cylinder 81 so as to run almost in its axial direction with depicting an S-letter shape. This cam slog 81a has a continuously formed return slot portion 81a' at its end on the distal end side of the cam slot. A cam screw 80 with a screw head is inserted through the cam slot 81a.

Figure 28:
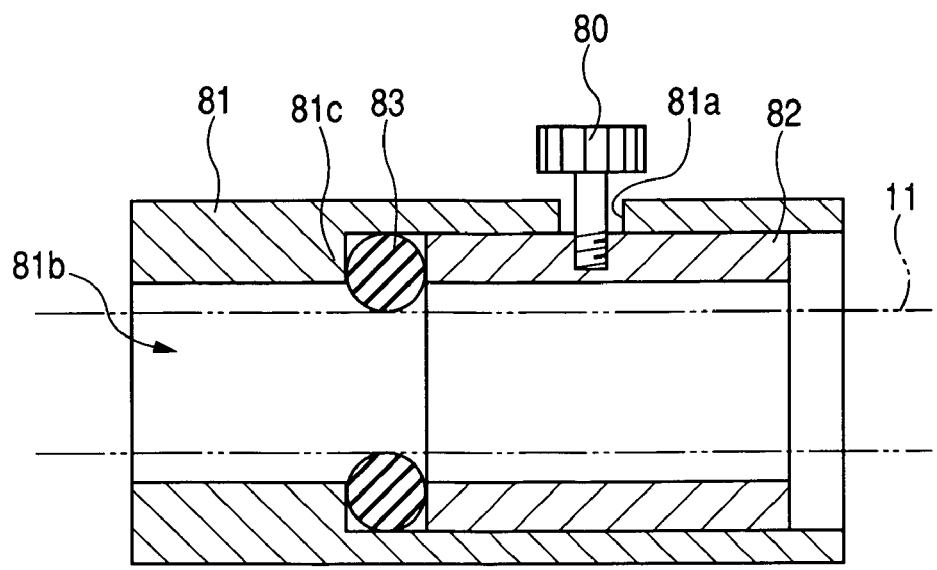
FIG. 28 is a longitudinal sectional view showing the manipulating unit loaded to the insertion tube.

Further, as shown in FIG. 28, in the cylinder 81, there is provided a movable ring 82 slidable in the axial direction. The cam 1o screw 80 is screwed into the outer portion of the ring 82. Inside the cylinder 81, there is formed a step-wise wall portion 81c connecting to a small-diameter portion formed on the distal end side. Between the step-wise wall portion 81c and the head of the movable ring 82, a rubber ring 83 is placed, which has a bore diameter almost equal to or slightly larger than the outer diameter of the insertion tube 11.

Hence, in the manipulating unit 45 thus constructed, with the insertion tube 11 inserted through a through-hole 81b of the cylinder 81, the cam screw 80 is slid along the cam slop 81a from the base end side to the distal end side, causing the movable ring 82 in the cylinder 81 to slide forward with rotations, thus causing the front end of the ring 82 to press the rubber ring 83.

Figure 29:
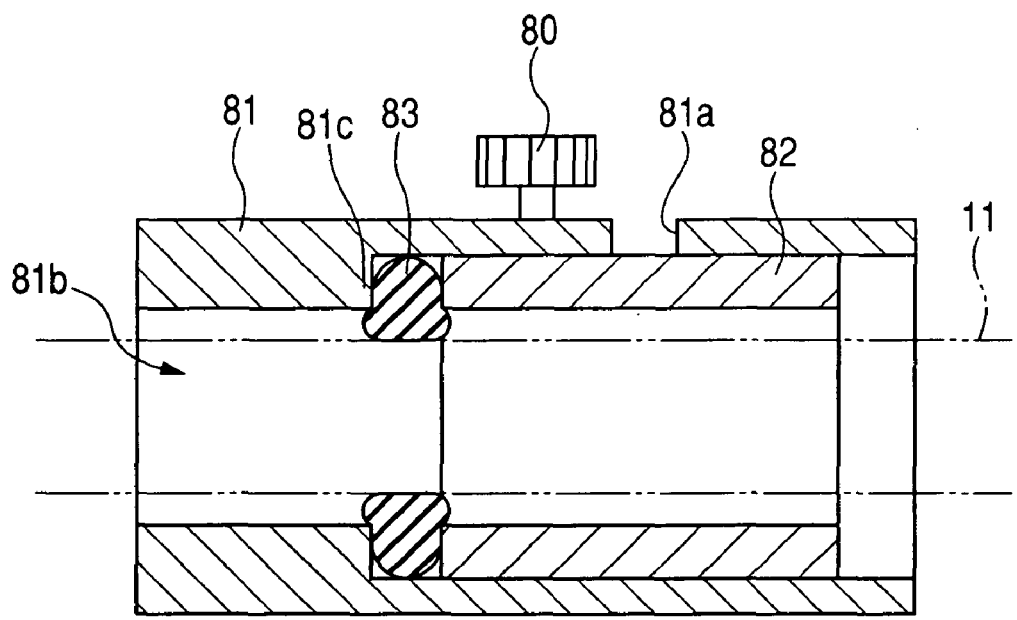
FIG. 29 explains how a rubber-made ring works the manipulating unit.

Thus, as shown in FIG. 29, the rubber ring 83 is pressed between the step-wise wall portion 81c and the movable ring 82. This pressing generates an elastic deformation of the rubber ring 83, which allows the rubber ring 83 to extend inward in the cylinder 81 so that the rubber ring 83 tightly touches the outer surface of the insertion tube 11. Hence the insertion tube of the endoscope 10 is pressed and held by the rubber ring 83. In the present modification, the mechanism involving the movable ring 82, rubber ring 83, cam screw 80, cam slot 81a, and cylinder 81 composes securing means.

As a result, an operator moves the cam screw 80 along the cam slot 81a, resulting in that the manipulating unit 45 can easily be secured to the insertion tube 11 of the endoscope 10. Namely, even when the operator abandons to grip the manipulating unit 45, the manipulating unit 45 can still be secured to the insertion tube 11, because the cam screw 80 forcibly returns back by the elasticity of the rubber ring 83 and hooked in the return slot portion 81a'.

In the present embodiment, the cam slot 81a i located at an almost axially central portion of the external loading tube 45A, which can be reached by the thumb of an operator who grips the manipulating unit 45, and is formed through the right-side wall portion when viewed from the front of the tube 45A. However, the position of the cam slot 81 is not limited to this example. For example, the cam slot 81 may be formed through an upper wall portion or left-side wall portion.

Figure 30:
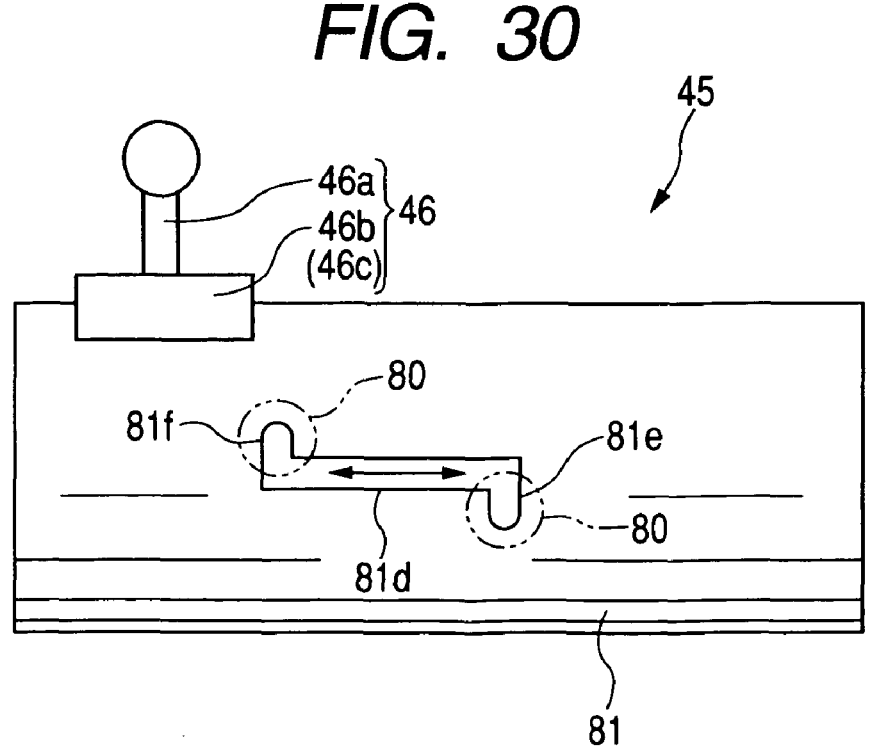
FIG. 30 is a side view according to a modified manipulating unit.

Moreover, the shape of the cam slot 81a may also be modified into another structure as shown in FIG. 30, for instance, where a cam slot 81d is formed to run straight in the axial direction. Further, this cam slot 81d may have a crank shape so that the straight cam slot 81d is connected to perpendicularly bent slot portions 81e and 81f at both axial ends thereof. These bent slot portions 81e and 81f function as stop slots to limit motions of the cam screw 80.

When the cam screw 80 is moved into the bent slot portions 81e or 81f, the cam screw 80 is locked and not permitted to move back and forth any more, securely holding the movable ring 82 in the cylinder 81. Specifically, when the cam screw 80 is in the bent slot potion 81e, the manipulating unit 45 gives no pressing force to the inserted insertion tube 11 via the rubber ring 83, so that the manipulating unit 45 can be slid freely along the insertion tube 11. When the cam screw 80 is in the remaining bent slot potion 81f, the manipulating unit 45 works to always press the insertion tube 11 using the rubber ring 83, thereby securing the manipulating unit 45 to the insertion tube 11.

(Third Modification)

Referring to FIGS. 31-34, a third modification of the manipulating unit will now be described.

Figure 31:
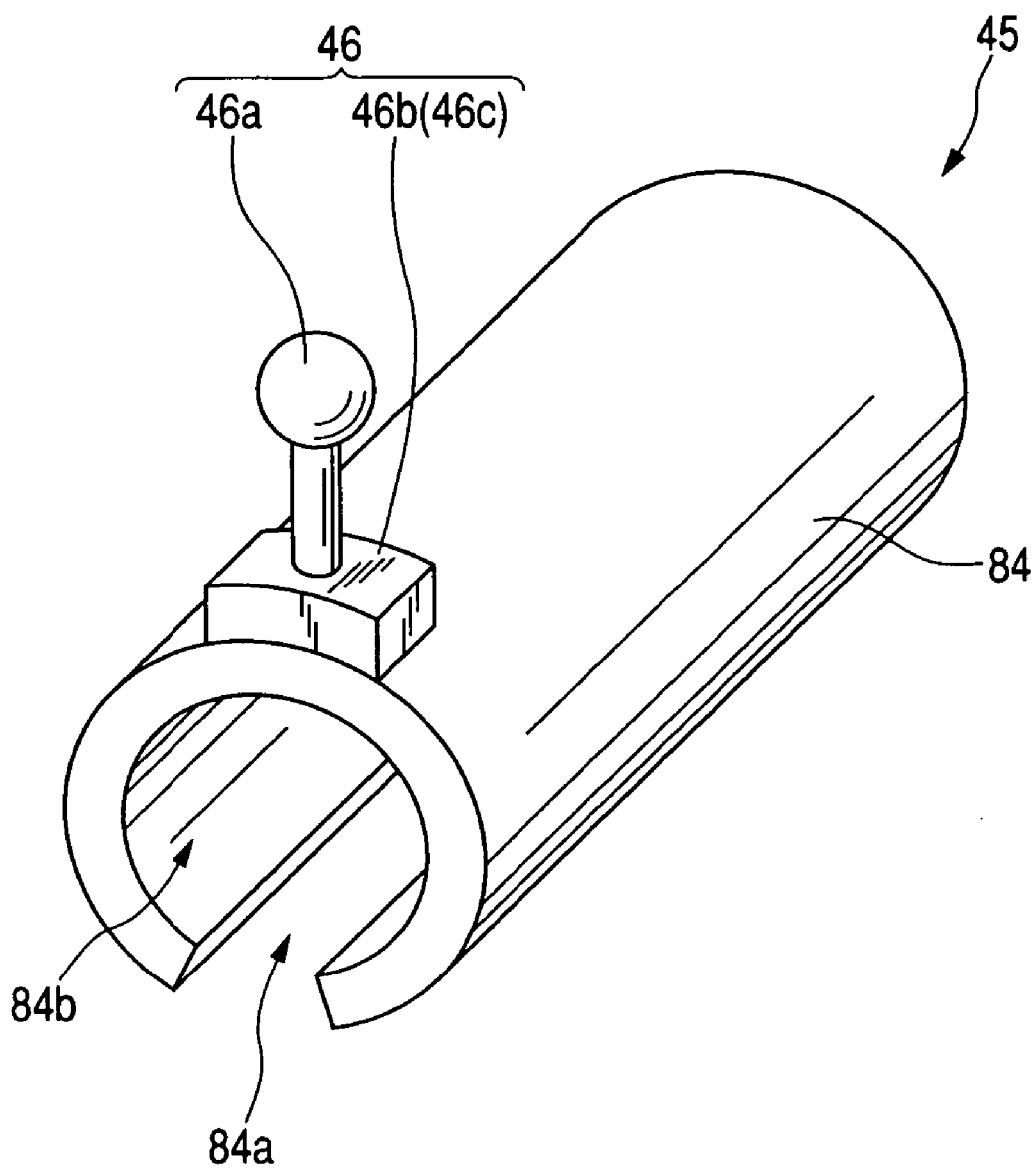
FIG. 31 is a perspective view showing a manipulating unit according to a third modification of the present invention.

As shown in FIG. 31, a manipulating unit 45 comprises an input device 46 and an external loading tube 84 of which section perpendicular to an axial direction thereof is an almost C-letter shape. The input device 46 is arranged at a distal-side position on the outer surface of the external loading tube 84. This external loading tube 84, made of elastic material, has a predetermined-width slit 84a running through the tube 84 in the axial direction so that the tube 84 has both wing portions and an inserting through-hole 84b through which the insertion tube 11 passes. The positions of the input device 46 and slit 84 are opposite to each other with the inserting through-hole 84b therebetween.

Figure 32:
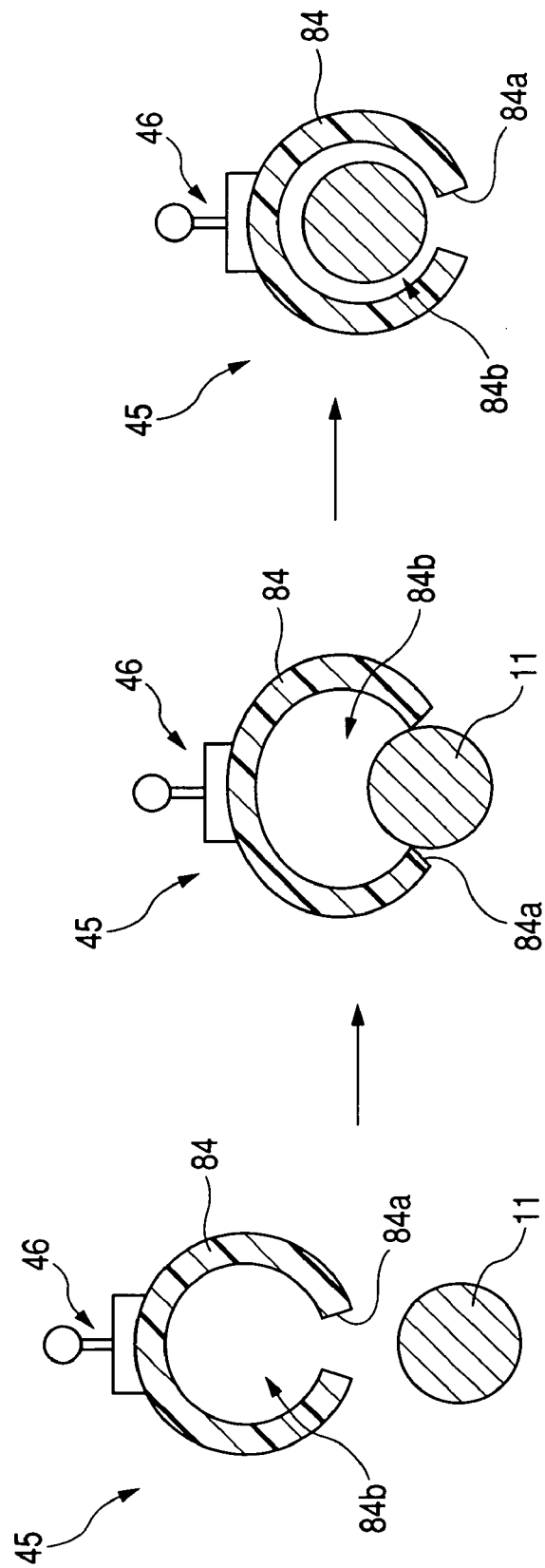
FIG. 32 explains how to load the manipulating unit shown in FIG. 31 to an insertion tube of an endoscope.

As shown FIG. 32, both wing portions of the external loading tube 84 are forcibly elastic-deformed to be widened outside respectively. This action allows the slit 81a to be winded as well to accommodate the insertion tube 11 in the inserting through-hole 84b. After the accommodation, both wings of the loading tube 84 are returned to their initial positions, so that the insertion tube 11 is retained in the inserting through-hole 84b.

Accordingly, in the present embodiment, the manipulating unit 45 can be detachably attached to the insertion tube 11 which is already inserted in a body cavity of an object being examined. Thus there is no need to attach the manipulating unit 45 to the insertion tube 11, in cases where the insertion tube 11 is inserted into or pulled back from a body cavity. Thus, in operating the insertion tube 11, the manipulating unit 45 does not become an obstacle to the work, facilitating the inserting and pulling-back operations.

Moreover, the external loading tube 84 is made of elastic material, thus permitting an operator to grip the manipulating unit 45 together with the insertion tube 11. In this grip, the external loading tube 84 is made to tightly touch the insertion tube 11, with the result that a force gripping the insertion tube 11 is increased.

Figure 33:
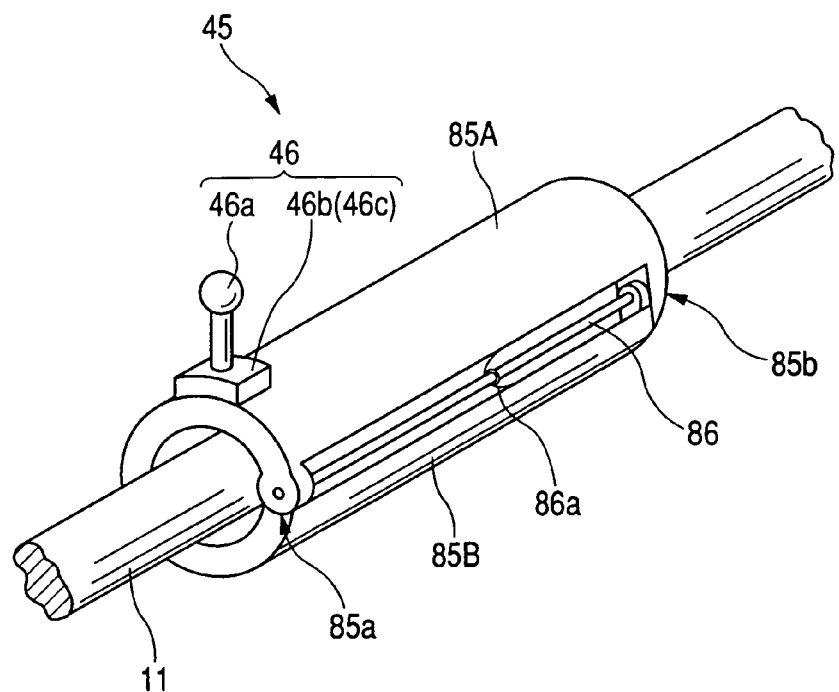
FIG. 33 is a perspective view showing a modified manipulating unit loaded to the insertion tube.

The structure shown in FIG. 33 is another modified example of the present modification, wherein the manipulating unit 45 can be attached detachably to the insertion tube which is already inserted into a body cavity.

To be specific, the manipulating unit 45 has a cylinder which is almost axially bisections into a first loading member 85A and a second loading member 85B. At a distal-side position on the outer surface of the first loading member 85A, an input device 46 is disposed. These loading members 85A and 85B form a substantially cylindrical member which provides a cylindrical through-hole having an axial direction and can be combined with a slit formed therebetween. The slit works an axis about which the loading members 85A and 85B are rotated respectively. Each member 85A (85B) is formed into a C shape when viewed in the axial direction.

Both loading members 85A and 85B are mutually linked by hinge 85a and 85b attached at both ends of the slit between the members 85A and 85B. Thus both loading members 85A and 85B can be rotated into mutually opposite directions around the hinges 85a and 85b, thereby providing a substantially cylindrical shape (but openable) to the manicuring unit 45.

A shaft 86 is arranged between the hinges 85a and 85b so as to rotatably hold the first and second loading members 85A and 85B. At the axial center of the shaft 86, a torsion spring 86a is arranged, which presses the first and second loading members 85A and 85B in a closing direction of the members 85A and 85B.

Figure 34:
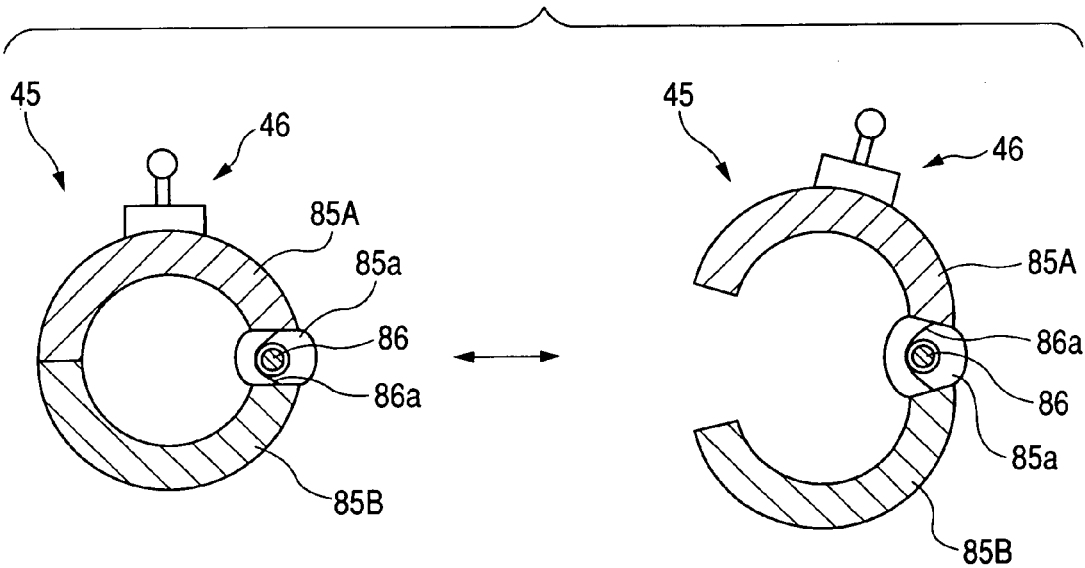
FIG. 34 explains how the manipulating unit in FIG. 33 works for being loaded to the insertion tube.

According to the foregoing structure, as shown in FIG. 34, the first and second loading members 85A and 85B can be rotated about their common shaft 86 for the open and close motions. It is therefore possible to attach the manipulating unit 45 detachably to the insertion tube 11 even after insertion of the insertion tube 11 into a body cavity, (Fourth Modification)

Figure 35:
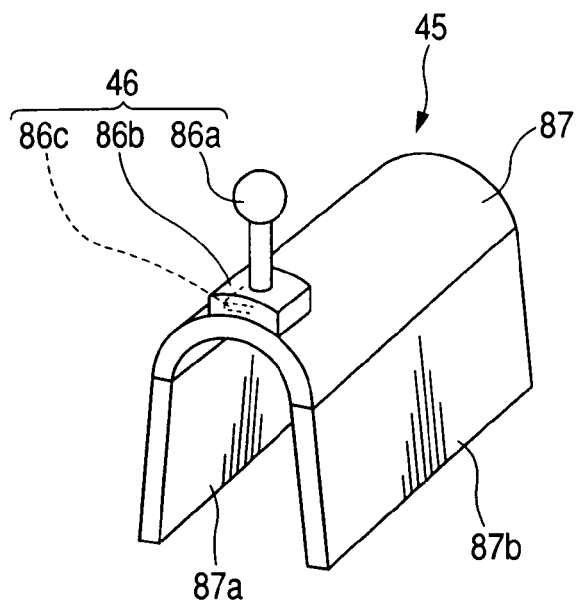
FIG. 35 is a perspective view showing a manipulating unit according to a fourth modification of the present invention.
Figure 36:
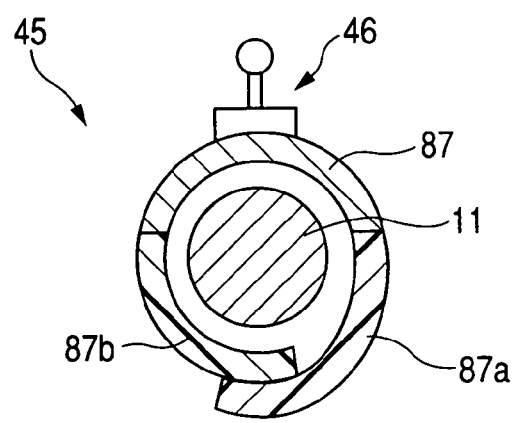
FIGS. 36 and 37 are sectional views each showing a state where the manipulating unit is loaded to the insertion tube.
Figure 37:
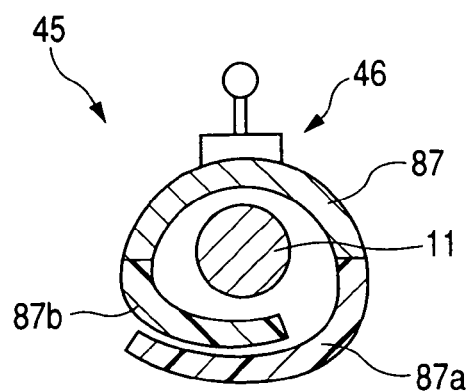

Referring to FIGS. 35-37, a fourth modification of the manipulating unit will now be described.

As shown in FIG. 35, a manipulating unit 45 of the present modification is equipped with an input device 46, a cover member 87 having an axial direction and a substantially U-shaped section in a plane perpendicular to the axial direction, and two strip-like surface fasteners 87a and 87b. Of these, the cover member 87 has an outer surface on which the input device 46 is disposed at a distal-side position thereon. The two surface fasteners 87a and 87b are respectively securely fastened to both axial edges of the cover member 87. The surface fasteners 87a and 87b are for example hook-andloop fasteners. Thus, the cover member 87 has a U-shaped-section groove, in which the insertion tube 11 of the endoscope 10 can be accommodated. The accommodated insertion tube 11 is wrapped around by the surface fasteners 87a and 87b, providing a state in which the insertion tube 11 is inserted through the manipulating unit 45. That is, the manipulating unit 45 is externally loaded to the insertion tube 11.

Accordingly, even the insertion tube 11 has a small diameter as shown in FIG. 36 or a large diameter as shown in FIG. 37, the manipulating unit 45 can be loaded to those insertion tubes 11 by using the surface fasteners 87a and 87b. A clearance between the manipulating unit 45 and the insertion tube 11 can be adjusted freely, so that the manipulating unit 45 can be gripped together with the insertion tube 11. Further, the surface fasteners 87a and 87b can be adhered to each other or detached from each other, whereby the manipulating unit 45 can easily be attached to or detached from the insertion tube 11.

(Fifth Modification)

Figure 38:
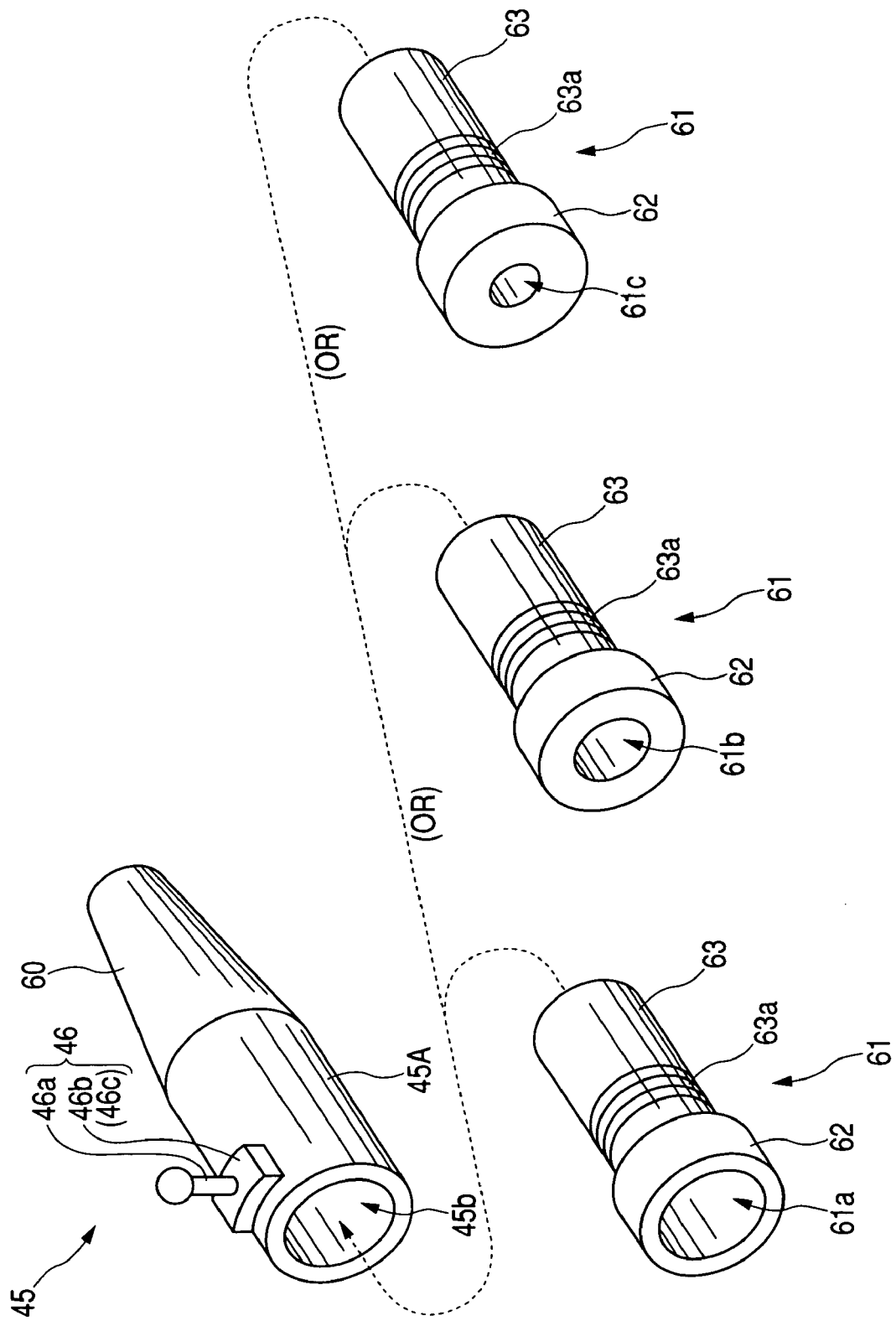
FIG. 38 is a perspective view showing a manipulating unit and a plurality of types of spacers which can be loaded to the manipulating unit in a fifth medication of the present invention.
Figure 39:
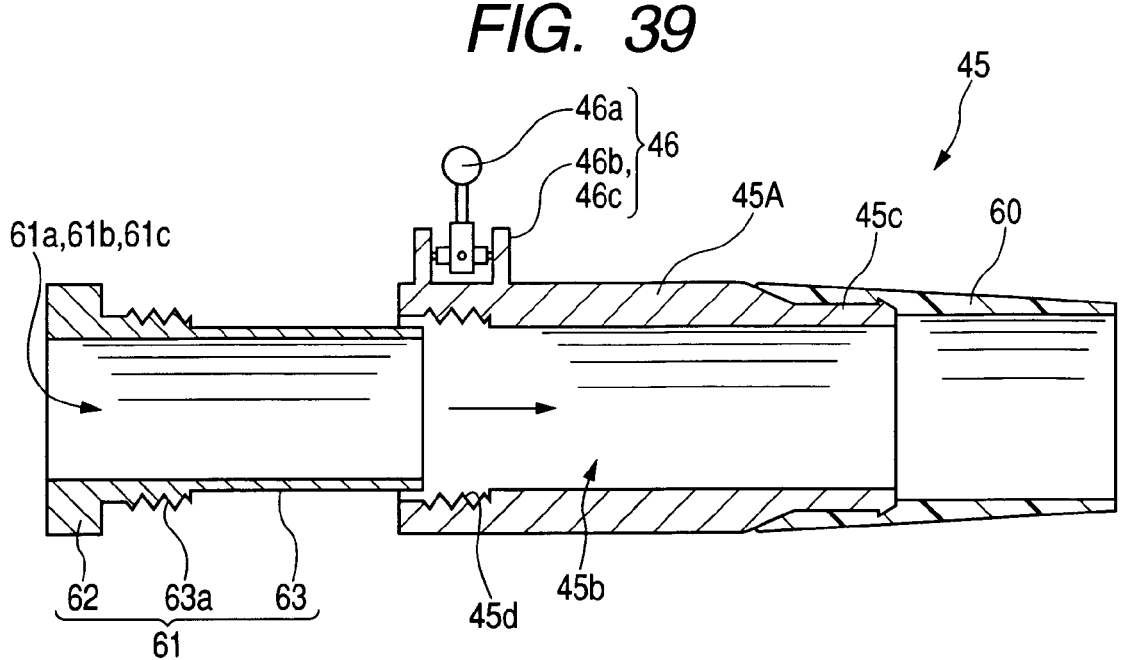
FIGS. 39 and 40 are longitudinal cross sectional views explaining how to load one spacer to the manipulating unit.
Figure 40:
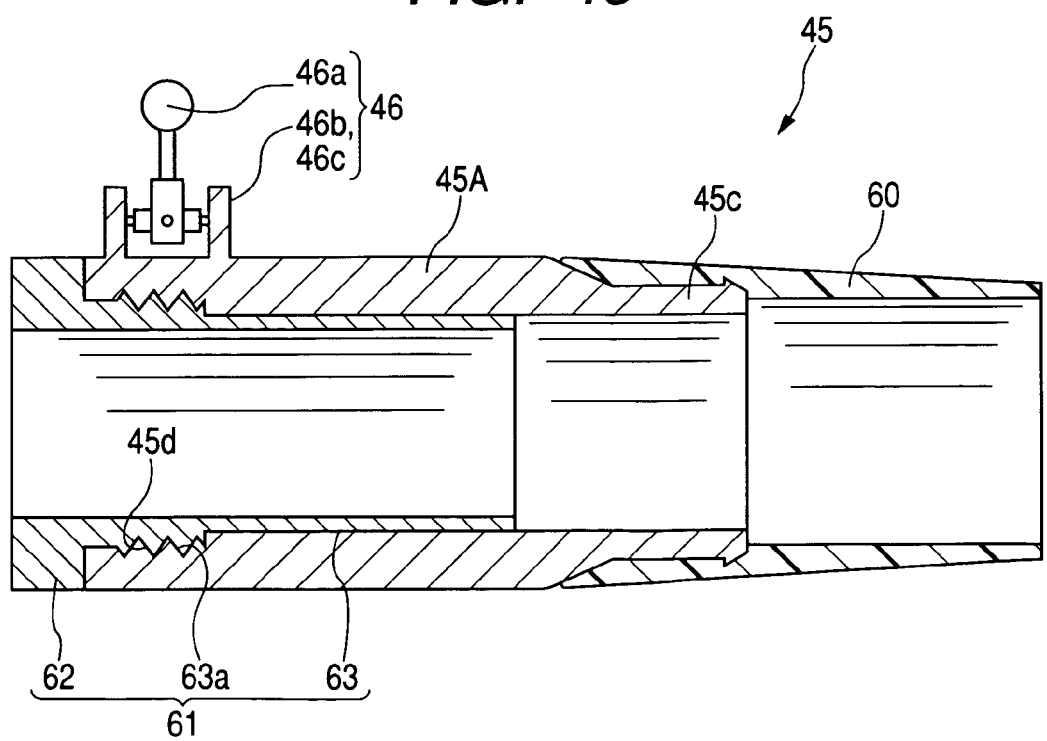

Referring to FIGS. 38-40, a fifth modification of the manipulating unit will now be described.

As shown in FIG. 38, a manipulating unit 45 according to the present modification selectively adopts a plurality of spacers 61, which can be attached to the inserting through-hole 45b of the external loading tube 45A. The number of spacers 61 is three, for example, as in the present modification.

Each of these spacers 61 has a substantially cylindrical form and comprises a distal cylinder portion 62 having an outer diameter approximately equal to that of the external loading tube 45A and a connecting cylinder portion 63 rigidly secured to the base of the distal cylinder portion 62 and formed to have an outer diameter roughly equal to the inner diameter of the inserting through-hole 45b. On the outer surface of the connecting cylinder portion 33 is provided a thread groove 63a which is permitted to be engaged with a thread groove 45d formed on the inner surface of the external loading tube 45A (refer to FIG. 39).

The three spacers 61 have axial through-holes 61a to 61c whose diameters are mutually different, respectively. Such different diameters are set depending on mutually different outer diameters of a plurality of types of insertion tubes 11 which can be employed by the endoscope 10.

As shown in FIGS. 39 and 40, each spacer 61 is applied to the external loading tube 45A in such a manner that the connecting cylinder portion 63 is inserted into the inserting through-hole 45b from the head thereof so as to the distal cylinder portion 62 reaches the front surface of the external loading tube 45A. After this insertion, the thread groove 63a is made to engage with the thread groove 45d, thus establishing a linkage between the spacer 61 and the manipulating unit 45. In this way, the spacer 61, which is selected to be best adaptive to the outer diameter of the insertion tube 11 to be used, can be loaded to the manipulating unit 45.

Thus, selective using the spacers 61 having different-diameter through-holes 61a, 61b, and 61c makes it possible to give an appropriate-size clearance between the outer diameter of the insertion tube 11 and the inner surface of the manipulating unit 45. The manipulating unit 45 can be slid smoothly and stably along the insertion tube 11. The one manipulating unit 45 can cope with an endoscope to which different-diameter insertion tubes can be applied.

(Sixth Modification)

Referring to FIGS. 41-45, a sixth modification of the manipulating unit will now be described.

Figure 41:
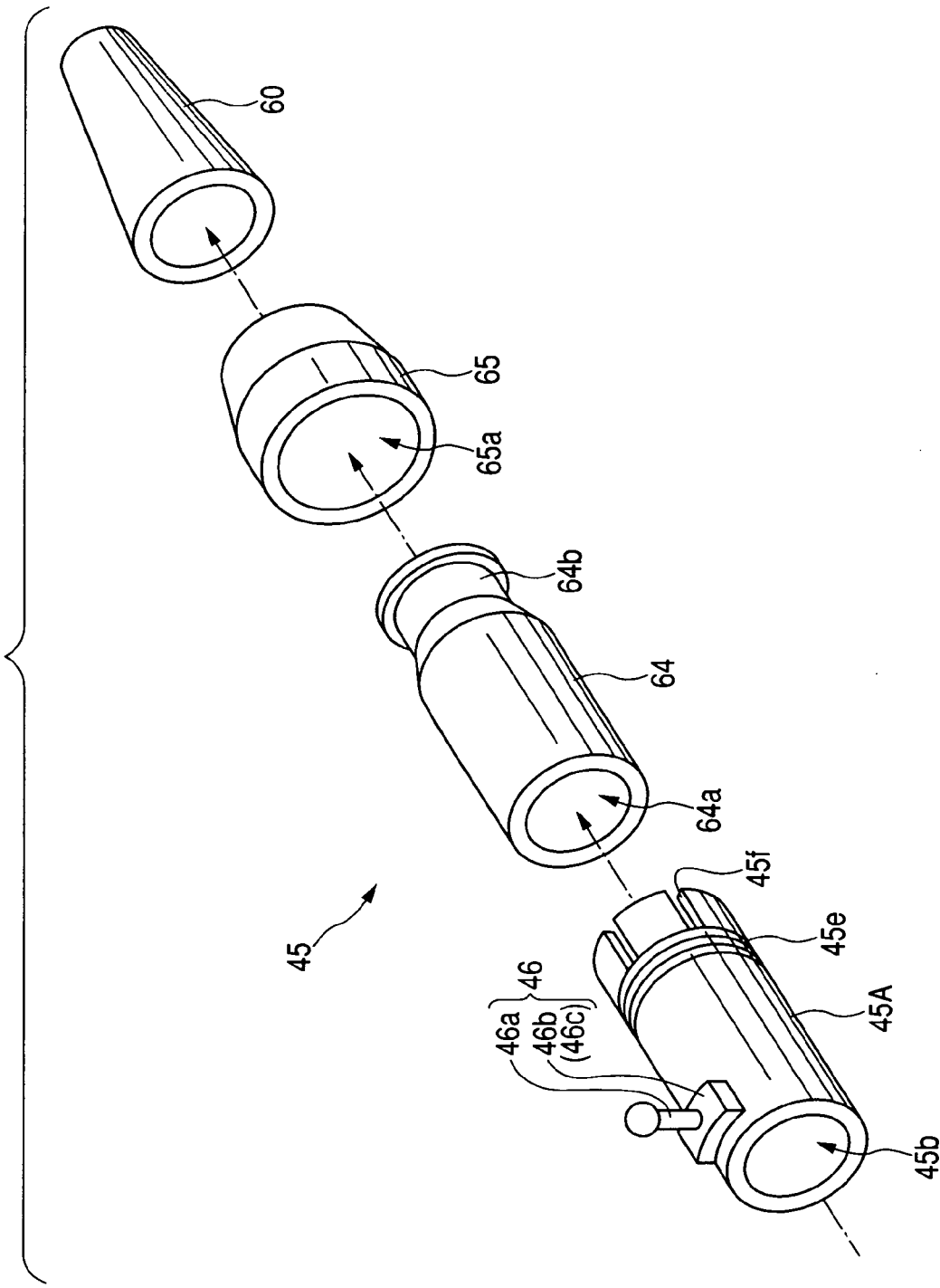
FIG. 41 is a disassembled perspective view of a manipulating unit according to a sixth modification of the present invention.

As shown in FIG. 41, a manipulating unit 45 of the present modification comprises an external loading tube 45A on which an input device 46 is mounted, a substantially cylindrical slide tube 64, a substantially toric fixing ring 65, and a soft grip 60.

Of these components, the external loading tube 45A is formed to have an inserting through-hole 45b, a thread groove 45e formed halfway on the outer surface in a direction perpendicular to its axial direction, and a plurality of axial slits 45f formed at a base end portion.

The slide tube 64 has an outer diameter substantially equal to the diameter of the inserting through-hole 45b, and is formed to have a through-hole 64a through which the insertion tube 11 can pass and a grip loading portion 64b formed to have a toric protrusion at a base end thereof. Meanwhile the fixing ring 65 is formed to have a through-hole 65a of a diameter substantially equal to the outer diameter of the external loading tube 45A and, on an inner surface thereof, as shown in FIG. 42, there are formed a thread groove 65b and a tapered surface 65c of which diameter decreases gradually toward the base end thereof.

Figure 42:
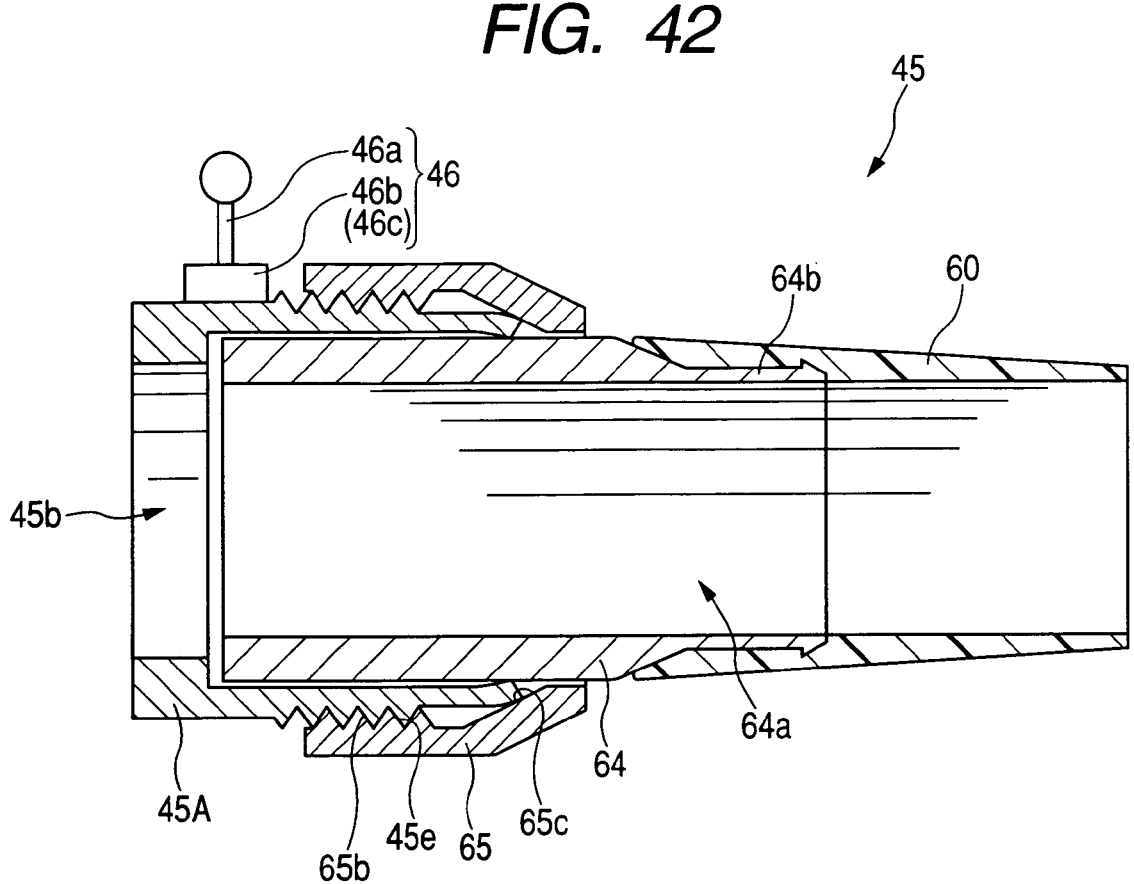
FIG. 42 is a longitudinal sectional view of the manipulating unit.
Figure 44:
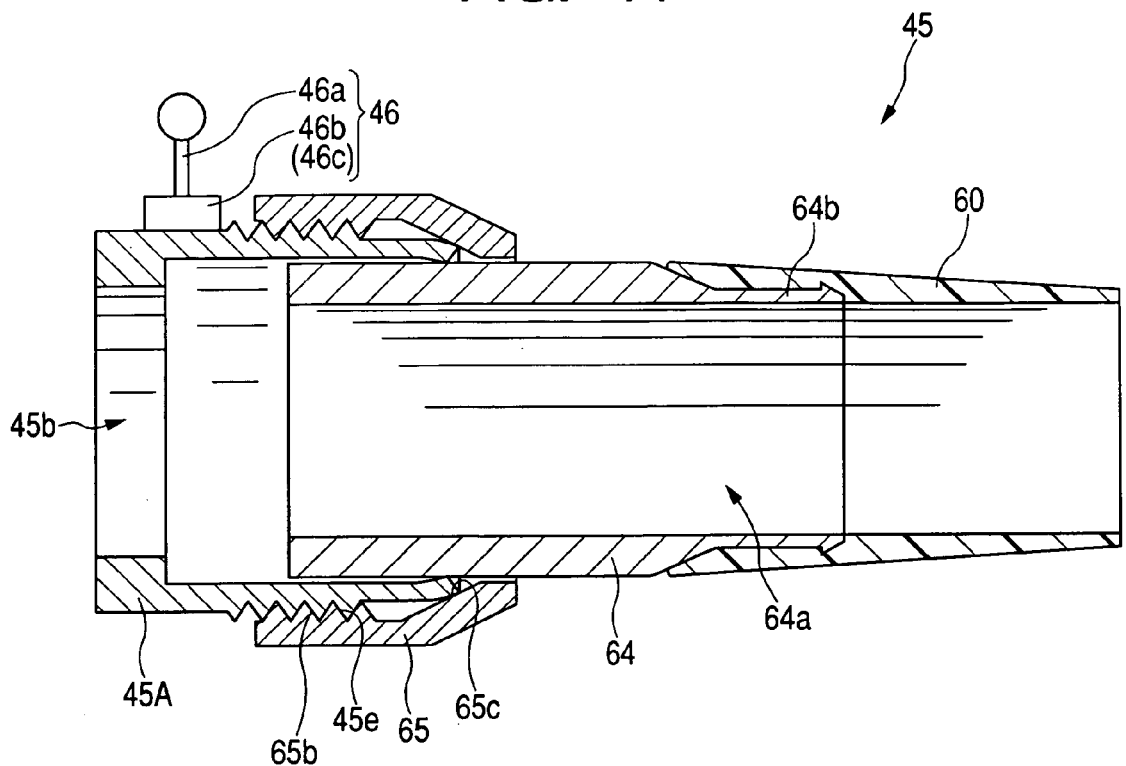
FIG. 44 is a longitudinal sectional view of a further modified manipulating unit.

As shown in FIGS. 42 and 44, the manipulating unit 45 is assembled such that the soft grip 60 is externally loaded to the grip loading portion 64b of the slide tube 64, and this slide tube is inserted in the external loading tube 45A. And the fixing ring 65 is externally loaded to the external loading tube 45A. In this case, the fixing ring 65 is securely fastened to the tube 45A by making its thread groove 65b with the thread groove 45e on the tube 45A.

Further, the base end of the external loading tube 45A is made to touch the tapered surface 65c of the fixing ring 65, so that the plurality of slits 45f are forcibly reduced in their widths, fixedly pressing the outer surface of the slide tube 64.

Figure 43:
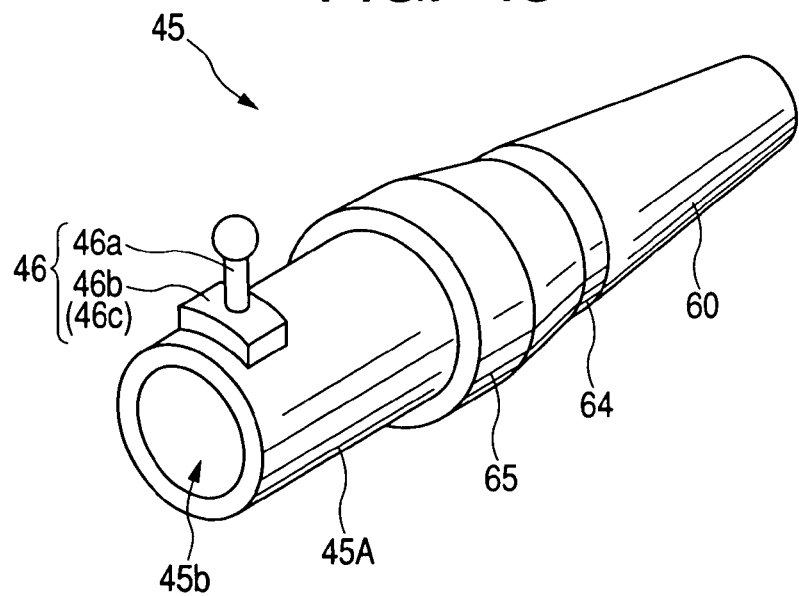
FIG. 43 is a perspective view of the manipulating unit.
Figure 45:
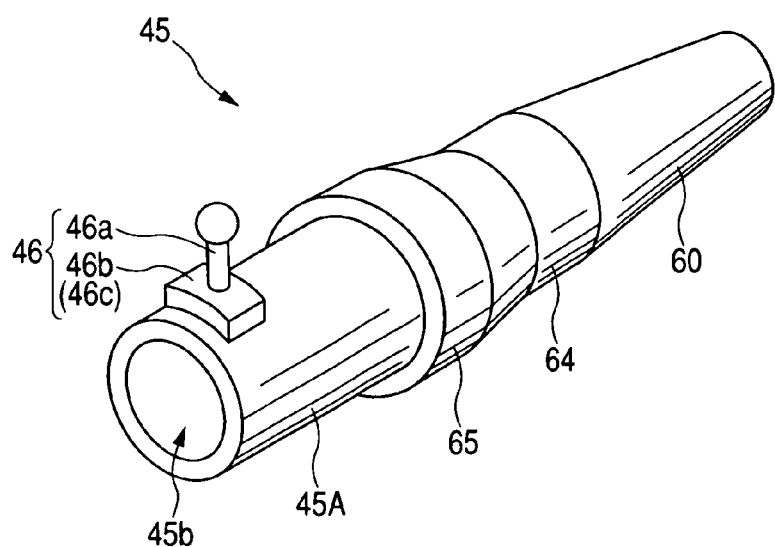
FIG. 45 is a perspective view of the manipulating unit.

As shown in FIGS. 42 and 43, the manipulating unit 45 assembled in this way functions such that, if the fixing ring 65 is engaged with the external loading tube 45A in a condition where the slide tube 64 is largely inserted in the tube 45A, the whole axial length of the unit 45 is made shorter. In contrast, as shown in FIGS. 44 and 45, if the fixing ring 65 is engaged with the external loading tube 45A in a condition where the slide tube 64 is less inserted in the tube 45A, the whole axial length of the unit 45 is made longer. To be short, an operator can adjust the whole length of the manipulating unit 45 by a length corresponding to an axial range of the slide tube 64 except for its grip loading portion 64b.

Hence in the present modification, depending on the size of an operator's hand, the axial length of the manipulating unit 45 can be adjusted to have a gripping portion adapting to easier gripping operations. Moreover, this manipulating unit 45 can be disassembled, thus being subjected easily to the cleaning and disinfecting process.

(Seventh Modification)

Figure 46:
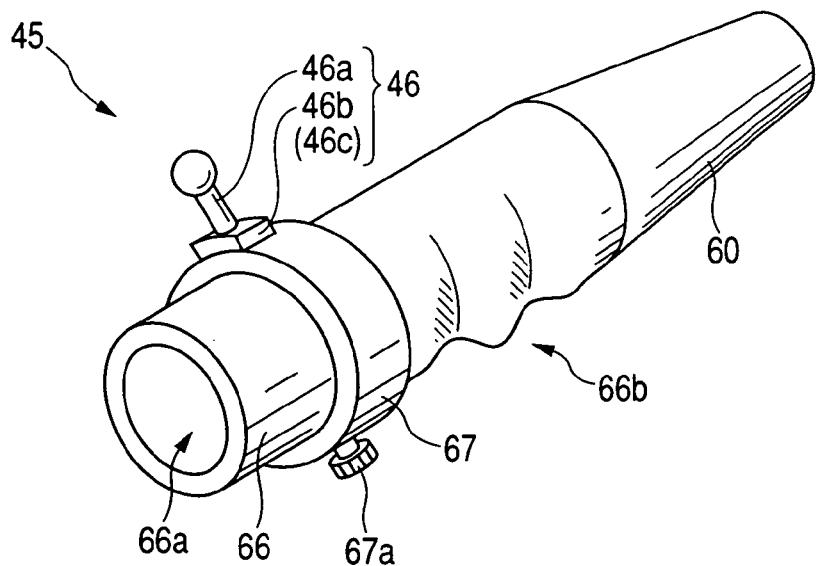
FIG. 46 is a perspective view of a manipulating unit according to a seventh modification of the present invention.
Figure 47:
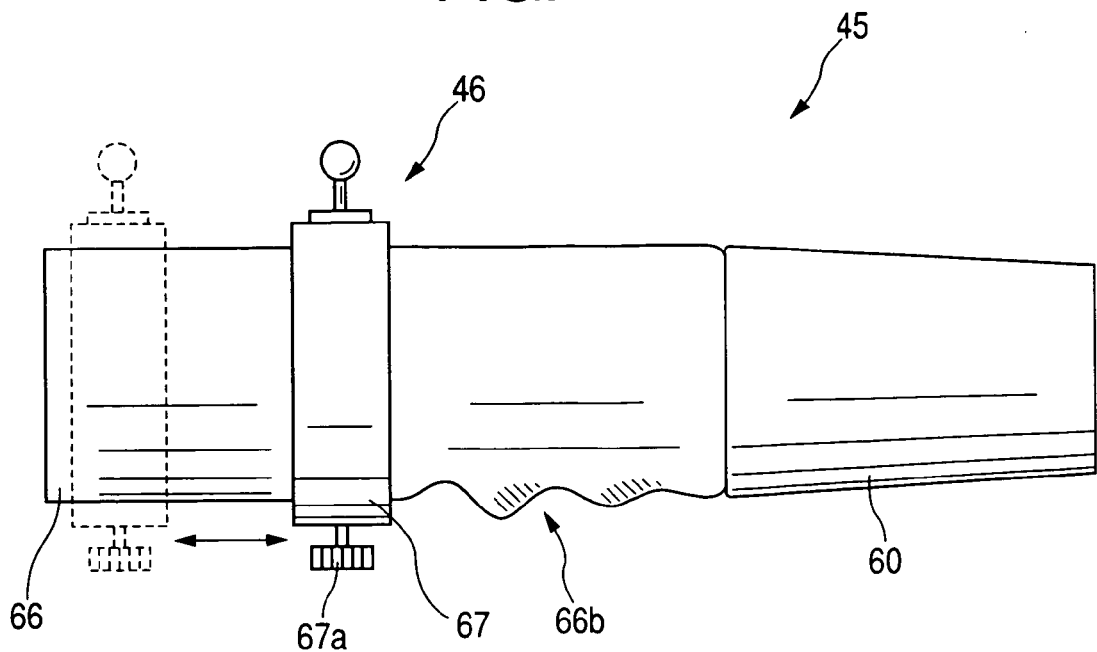
FIG. 47 is a side view of the manipulating unit.

Referring to FIGS. 46-47, a seventh modification of the manipulating unit will now be described.

As shown in FIG. 46, in the present modification, a manipulating unit comprises a substantially cylindrical external loading tube 66 and an input device 46. On the outer surface of this external loading tube 66, an approximately toric attaching ring 67 is attached in a detachable manner. And a soft grip 60 is linked to the base end of this tube 66.

The external loading tube 66 has an inserting through-hole 66a through which the insertion tube 11 is inserted and a gripping portion 66b formed on a base-end side of this tube 66. This gripping portion has a wavy outer surface. The soft grip 60 is structured in the same manner as the foregoing one.

The attaching ring 67 is subjected to penetration of a setscrew 67a serving as a fixing screw to the outer surface of the tube 66. The setscrew 67a is positioned to be opposed to the input device 46 also mounted to the ring 67. Depending on how much the setscrew 67a engages with the attaching ring 67, the setscrew 67a presses the outer surface of the external loading tube 66, fixing the attaching ring 67 to the tube 66.

It is therefore possible that, as shown in FIG. 47, the attaching ring 67 can be slid and rotated along and around the external loading tube 66. Further, fastening the setscrew 67a makes it possible to fixedly set the attaching ring 67 at an operator's desired axial position along the tube 66.

Accordingly, the attaching ring 67 can be fixed at an axial position which allows an operator to handle the input device 46 easily. Independently of operator's hand sizes, the manipulating unit 45 can be improved in operational performance and made easier in gripping together with the insertion tube 11.

(Eighth Modification)

Figure 48:
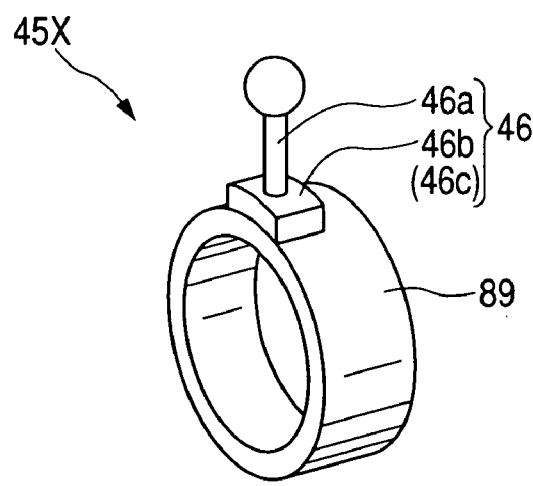
FIG. 48 is a perspective view of a manipulating unit according to an eighth modification of the present invention.
Figure 49:
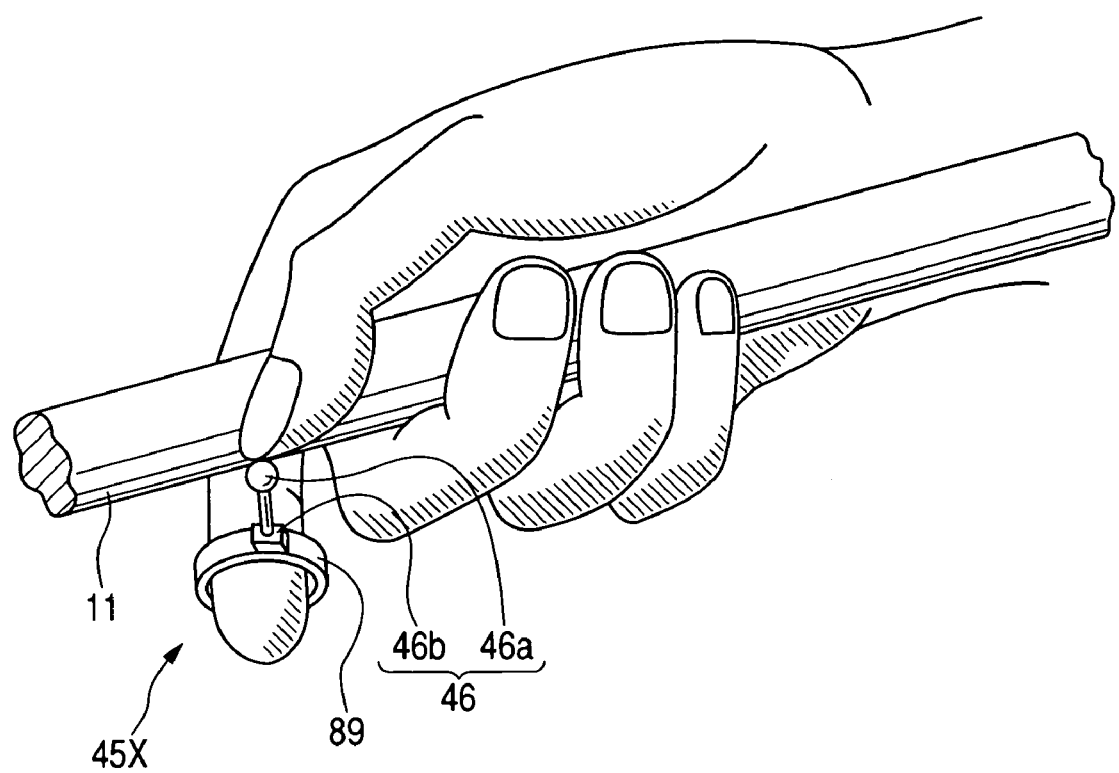
FIG. 49 is a perspective view illustrating how to load the manipulating unit to an operator's finger and how to grip an insertion tube of an endoscope.

Referring to FIGS. 48-49, an eighth modification of the manipulating unit will now be described.

In this modification, as shown in FIG. 48, a manipulating unit 45X has a toric finger ring 89 and an input device 46 mounted on the toric finger ring 89. As shown in FIG. 49, this manipulating unit 45X is, for example, loaded to an operator's first finger, while still allowing the thumb to handle the input device 46.

Therefore, the whole palm of an operator's hand can be used to grip the insertion tube 11, whereby it makes easier to grip the insertion tube 11 again. In other words, by using this modified manipulating unit 45X, it is easier for operators to perform sensitive insertion operations such as re-approach of the insertion tube 11 into a body cavity. (Ninth Modification)

Referring to FIGS. 50-53, a ninth modification of the manipulating unit will now be described.

Figure 50:
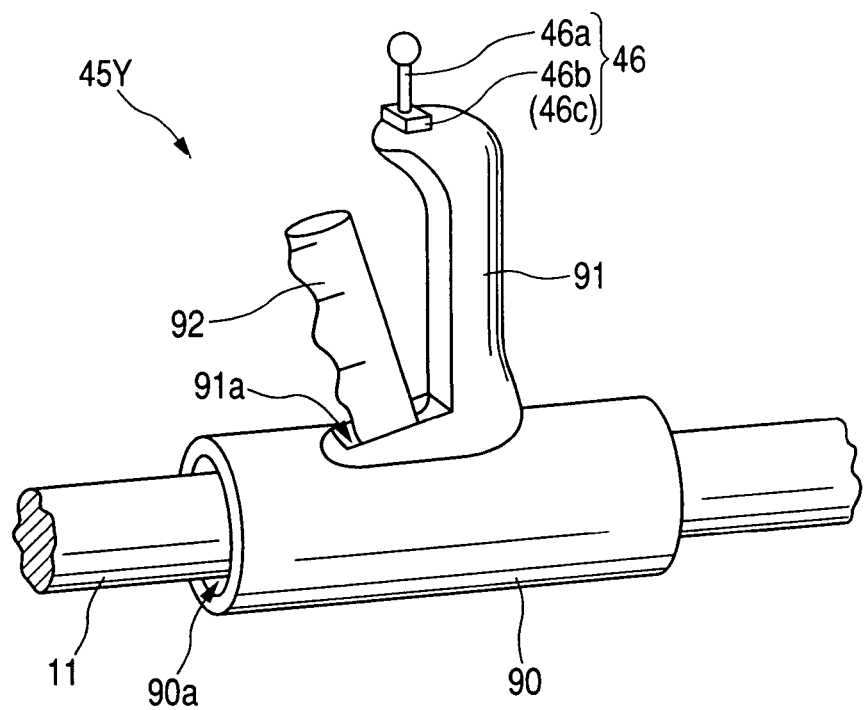
FIG. 50 is a perspective view of a manipulating unit according to a ninth modification of the present invention, the manipulating unit being loaded to the outer surface of an insertion tube of an endoscope.

As shown in FIG. 50, there is provided a further modified manipulating unit 45Y comprising an external loading tube 90 approximately formed into a cylinder, a grip 91 protruding from the outer surface of the tube 90 at an axial midway position thereof, and a fixing lever 92 mounted to the grip 91. The external loading tube 90 has an inserting through-hole 90a through which the insertion tube 11 is inserted. An input device 46 is mounted at the top of the grip 91. The grip 91 has a hole 91a at the base and the fixing lever 92 is rotatably placed in the hole 91a.

Figure 51:
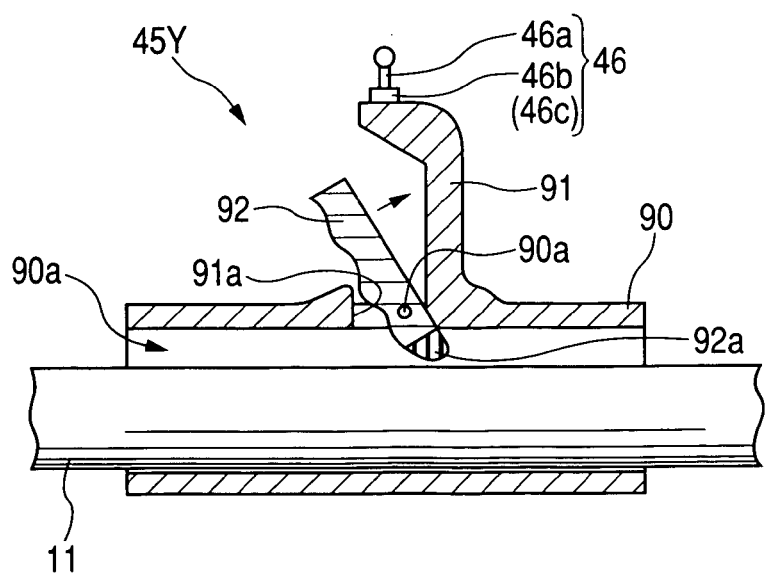
FIG. 51 is a longitudinal sectional view of the manipulating unit.

As shown in FIG. 51, the grip 91 is extended almost perpendicularly from the external loading tube 90 and has a top portion bent forward to form a reversed-L-letter shape in an axial section. As described, the input device 46 is mounted on this top portion. The hole 91a is located in front of the base of the grip 91.

In the hole 91a, there is placed a fixing lever 92 rotatably held by a rotation shaft 90a. This fixing lever 92 has a stopper 92a at an end thereof so as to reside in the inserting through-hole 90a of the external loading tube 90. The stopper 92a is made of elastic material. A spring member may be arranged between the fixing lever 92 and the grip 91 in order to force the fixing lever 92 forward.

Figure 52:
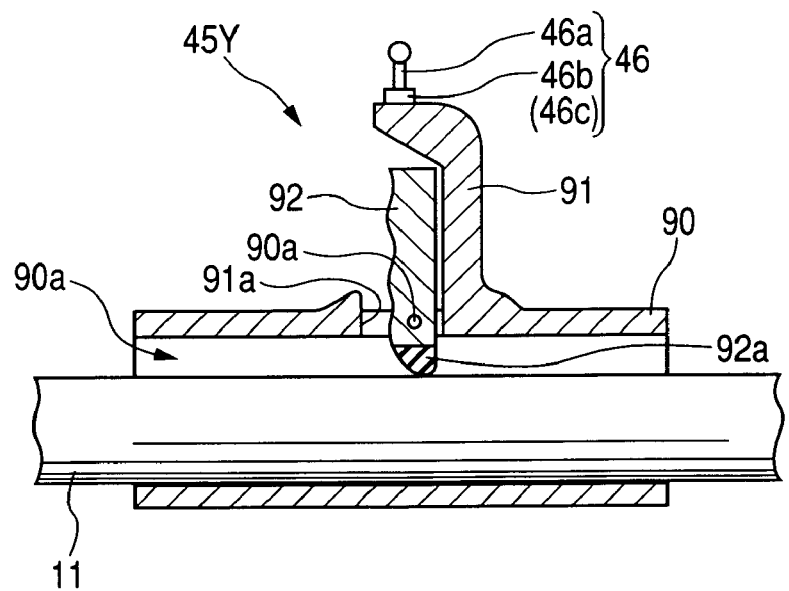
FIGS. 52 and 53 are illustrations each explaining operations of the manipulating unit.

In the present manipulating unit 45Y, as shown by a transition from FIG. 51 to 52, the fixing lever 92 is rotated toward the grip 91. On completion of the rotation, the stopper 92a of the fixing lever 92 presses the outer surface of the insertion tube inserted in the through-hole 90a of the external loading tube 90. That is, the insertion tube 11 is pinched between the inner surface of the external loading tube 90 and the stopper 92a, thus being fixedly held there.

Figure 53:
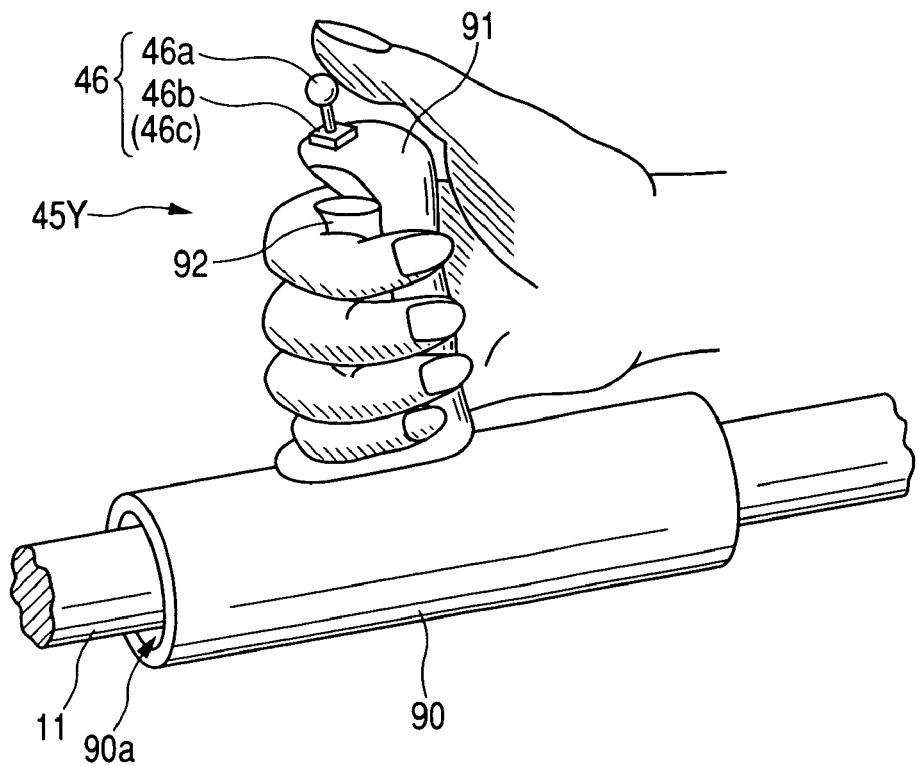

As shown in FIG. 53, when rotating the fixing lever 92, an operator grips the fixing lever together with the grip 91, facilitating the rotation of the fixing lever 92. In this gripping state, the input device 46 can be handled by for example the thumb. Therefore, the manipulating unit 45Y provides the input device 46 with an improved operational performance and the insertion tube 11 with a sure holding function.

Although the description above contains many specificities, these should not be construed as limiting the scope of the invention but as merely providing Illustrations of some of the presently preferred embodiments of the present invention. Thus the scope of the present invention should be determined by the appended claims.

What is claimed is:

1. An endoscope system comprising:
   an endoscope equipped with an elongated and flexible insertion tube being insertable into an object being examined and formed to be used in combination with a therapeutic instrument, the insertion tube having a distal section accommodating therein at least an optical system for imaging and presenting a longitudinal direction;
   a manipulating unit manually manipulated for commanding operations of at least the therapeutic instrument and formed to be loaded to the insertion tube and slidable along the insertion tube in the longitudinal direction thereof; and
   a controlling apparatus adapted to control at least the therapeutic instrument based on a command from the manipulating unit, wherein
   the manipulating unit comprises a substantially cylindrical tube member detachably loaded to the insertion tube of the endoscope and presenting an axial direction,
   the manipulating unit comprises an input device at which the operations are demanded, the input device being movably fixed to the tube member,
   the manipulating unit comprises a substantially toric ring member having an inner diameter larger than an outer diameter of the tube member, and being slidable in both the axial direction of the tube member and a circumferential direction of the tube member, the input device being mounted on the ring member, and
   the ring member comprises a fixing means adapted for fixing the ring member at any position of the tube member.

2. The endoscope system of claim 1, wherein the insertion tube comprises
   a therapeutic-instrument channel through which the therapeutic instrument passes;
   the therapeutic instrument comprises a tubular portion including a therapeutic member arranged at a distal end of the tubular portion, both the tubular portion and the therapeutic member being allowed to pass through the therapeutic-instrument channel;
   the manipulating unit comprises a first input device manually handled to issue, as the command, a first command for conveying the tubular portion and for operating the therapeutic member; and
   the controlling apparatus comprises a first drive unit driving the tubular portion of the therapeutic instrument so as to convey the tubular portion through the therapeutic-instrument channel in response to the first command, and a second drive unit driving a handle of the therapeutic instrument so as to operate the therapeutic member in response to the first command from the first input device.

3. The endoscope system of claim 2, wherein
   the manipulating unit comprises a second input device manually handled to issue, as the command, a second command for rotating the therapeutic member about a longitudinal axis of the tubular portion for rotating the therapeutic member and the second drive unit comprises a rotating mechanism for rotating the therapeutic member in response to the is second command from the second input device.

4. The endoscope system of claim 2, wherein the first input device is located on a distal-end side of the manipulating unit.

5. The endoscope system of claim 2, wherein the manipulating unit comprises a grip presenting an axial direction and allowing an operator to grip the manipulating unit, wherein the grip and the first input device are aligned in an axial direction of the grip.

6. The endoscope system of claim 5, wherein the grip composes a base portion of the manipulating unit in the axial direction.

7. The endoscope system of claim 5, wherein the grip is elastically deformed.

8. The endoscope system of claim 5, wherein the grip is formed to have a substantial cylindrical shape.

9. The endoscope system of claim 1, wherein the manipulating unit comprises a grip being linked to the tube member and a mechanism for adjusting a length of the grip in the axial direction.

10. An apparatus comprising:
a manipulating unit manually manipulated for commanding operations of at least a therapeutic instrument slidably loaded to an insertion tube of an endoscope and conveyed along a therapeutic-instrument channel formed through the insertion tube along a longitudinal direction thereof and
a controlling apparatus controlling at least the therapeutic instrument based on a command from the manipulating unit, wherein
the manipulating unit comprises a substantially cylindrical tube member detachably loaded to the insertion tube of the endoscope and presenting an axial direction,
the manipulating unit comprises an input device at which the operations are demanded, the input device being movably fixed to the tube member,
the manipulating unit comprises a substantially toric ring member having an inner diameter larger than an outer diameter of the tube member, and being slidable in both the axial direction of the tube member and a circumferential direction of the tube member, the input device being mounted on the ring member, and
the ring member comprises a fixing means adapted for fixing the ring member at any position of the tube member.

11. The apparatus of claim 10, wherein the insertion tube comprises a therapeutic-instrument channel through which the therapeutic instrument passes; the therapeutic instrument comprises a tubular portion 2o including a therapeutic member arranged at a distal end of the tubular portion, both the tubular portion and the therapeutic member being allowed to pass through the therapeutic-instrument channel; the manipulating unit comprises a first input device manually handled to issue, as the command, a first command for conveying the tubular portion and for operating the therapeutic member; and the controlling apparatus comprises a first drive unit driving the tubular portion of the therapeutic instrument so as to convey the tubular portion through the therapeutic-instrument channel in response to the first command, and a second drive unit driving a handle of the therapeutic instrument so as to operate the therapeutic member in response to the first command from the first input device.

12. The apparatus of claim 11, wherein the manipulating unit comprises a second input device manually handled to issue, as the command, a second command for rotating the therapeutic member about a longitudinal axis of the tubular portion for rotating the therapeutic member and a rotating mechanism for rotating the therapeutic member in response to the second command from the second input device.

* * * * *